US011708411B2

(12) United States Patent
Haas et al.

(10) Patent No.: US 11,708,411 B2
(45) Date of Patent: Jul. 25, 2023

(54) METHODS AND COMPOSITIONS FOR INCREASING PROTECTIVE ANTIBODY LEVELS INDUCED BY PNEUMOCOCCAL POLYSACCHARIDE VACCINES

(71) Applicant: Wake Forest University Health Sciences, Winston-Salem, NC (US)

(72) Inventors: Karen Haas, Clemmons, NC (US); Jerome Mckay, Mebane, NC (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 101 days.

(21) Appl. No.: 15/106,071

(22) PCT Filed: Dec. 22, 2014

(86) PCT No.: PCT/US2014/071901
§ 371 (c)(1),
(2) Date: Jun. 17, 2016

(87) PCT Pub. No.: WO2015/095868
PCT Pub. Date: Jun. 25, 2015

(65) Prior Publication Data
US 2016/0311904 A1 Oct. 27, 2016

Related U.S. Application Data

(60) Provisional application No. 61/919,360, filed on Dec. 20, 2013.

(51) Int. Cl.
*A61K 39/00* (2006.01)
*A61K 39/116* (2006.01)
*A61K 39/09* (2006.01)
*A61K 39/395* (2006.01)
*C07K 16/28* (2006.01)

(52) U.S. Cl.
CPC ........ *C07K 16/2827* (2013.01); *A61K 39/092* (2013.01); *A61K 39/116* (2013.01); *A61K 39/3955* (2013.01); *A61K 2039/505* (2013.01); *A61K 2039/6087* (2013.01); *A61K 2039/70* (2013.01); *C07K 2317/76* (2013.01)

(58) Field of Classification Search
None
See application file for complete search history.

(56) References Cited

U.S. PATENT DOCUMENTS

| | | |
|---|---|---|
| 4,365,170 A | 12/1982 | Okuhara |
| 4,474,893 A | 10/1984 | Reading |
| 4,522,811 A | 6/1985 | Eppstein et al. |
| 4,673,574 A | 6/1987 | Anderson |
| 4,709,017 A | 11/1987 | Collier et al. |
| 4,816,567 A | 3/1989 | Cabilly et al. |
| 4,902,506 A | 2/1990 | Anderson et al. |
| 4,912,094 A | 3/1990 | Myers et al. |
| 4,950,740 A | 8/1990 | Greenfield et al. |
| 5,057,540 A | 10/1991 | Kensil et al. |
| 5,116,964 A | 5/1992 | Capon et al. |
| 5,223,409 A | 6/1993 | Ladner et al. |
| 5,225,539 A | 7/1993 | Winter |
| 5,328,470 A | 7/1994 | Nabel et al. |
| 5,565,332 A | 10/1996 | Hoogenboom et al. |
| 5,580,756 A | 12/1996 | Linsley et al. |
| 5,614,382 A | 3/1997 | Metcalf |
| 5,698,520 A | 12/1997 | Honjo et al. |
| 5,733,743 A | 3/1998 | Johnson et al. |
| 5,798,229 A | 8/1998 | Strittmatter et al. |
| 5,843,711 A | 12/1998 | Collier et al. |
| 5,844,095 A | 12/1998 | Linsley et al. |
| 5,847,112 A | 12/1998 | Kniskern et al. |
| 5,871,907 A | 2/1999 | Winter et al. |
| 5,917,017 A | 6/1999 | Collier et al. |
| 5,959,084 A | 9/1999 | Ring et al. |
| 6,113,918 A | 9/2000 | Johnson et al. |
| 6,146,902 A | 11/2000 | Mcmaster |
| 6,207,646 B1 | 3/2001 | Krieg et al. |
| 6,455,673 B1 | 9/2002 | Collier |
| 2003/0147922 A1 | 8/2003 | Capiau et al. |
| 2008/0286838 A1 | 11/2008 | Yuan et al. |

(Continued)

FOREIGN PATENT DOCUMENTS

| | | |
|---|---|---|
| EP | 0173494 A2 | 3/1986 |
| EP | 0125023 B1 | 6/1991 |
| EP | 9171496 B1 | 5/1993 |

(Continued)

OTHER PUBLICATIONS

Haas KM. J. Immunology 183: 3661-3671, pp. 1-10, 2009.*
Rodig et al. Eur. J. Immunol. 33: 3117-3126, 2003.*
Illustrated Stedman's Medical Dictionary, 24th Edition, Williams and Wilkins, London, p. 707, 1982.*
"Programmed cell death 1 [*Homo sapiens*]"; NSBI, GenBank accession No. AAH74740.1; dated Jul. 15, 2006.
"Programmed cell death 1 ligand 2 [*Homo sapiens*]"; NSBI, GenBank accession No. CA15984.1; dated Jan. 13, 2009.
"Programmed death ligand 1 variant [*Homo sapiens*]"; NSBI, GenBank accession No. AAP42144.1; dated Apr. 26, 2004.
Haas, K. M., Programmed cell death 1 suppresses B-1b cell expansion and long-lived IgG production in response to T cell-independent type 2 antigens:, The Journal of Immunology; vol. 187, No. 10, dated Nov. 15, 2011; pp. 5183-5195.

(Continued)

*Primary Examiner* — S. Devi
(74) *Attorney, Agent, or Firm* — Myers Bigel, P.A.

(57) ABSTRACT

The presently disclosed subject matter provides therapeutic methods and compositions for the treatment of bacterial infections caused by *Streptococcus pneumoniae*. In particular, methods are provided for increasing protective antibody levels induced by pneumococcal polysaccharide vaccines in a subject in need thereof comprising administering to the subject an effective amount of an agent that inhibits the interaction between a PD-1 ligand and a PD-1 polypeptide. Immunogenic compositions are also provided comprising one or more pneumococcal polysaccharide antigens and an agent that inhibits the interaction between a PD-1 ligand and a PD-1 polypeptide.

14 Claims, 17 Drawing Sheets

Specification includes a Sequence Listing.

(56) References Cited

U.S. PATENT DOCUMENTS

| | | | |
|---|---|---|---|
| 2010/0209450 A1 | 8/2010 | Biemans et al. | |
| 2013/0266609 A1* | 10/2013 | Boutriau | A61K 39/095 424/197.11 |

FOREIGN PATENT DOCUMENTS

| | | |
|---|---|---|
| EP | 9378881 B1 | 6/1993 |
| EP | 0427347 B1 | 2/1995 |
| EP | 0471177 B1 | 10/1995 |
| EP | 0497524 B1 | 7/1998 |
| EP | 0497525 B1 | 8/1998 |
| EP | 0594610 B1 | 9/1998 |
| WO | 8601533 A1 | 3/1986 |
| WO | 8702671 A1 | 5/1987 |
| WO | 9101146 A1 | 2/1991 |
| WO | 9117271 A1 | 11/1991 |
| WO | 9201047 A1 | 1/1992 |
| WO | 9209690 A2 | 6/1992 |
| WO | 9215679 A1 | 9/1992 |
| WO | 9218619 A1 | 10/1992 |
| WO | 9220791 A1 | 11/1992 |
| WO | 9301288 A1 | 1/1993 |
| WO | 9315760 A1 | 8/1993 |
| WO | 9317712 A2 | 9/1993 |
| WO | 9402610 A1 | 2/1994 |
| WO | 9403208 A1 | 2/1994 |
| WO | 9503832 A1 | 2/1995 |
| WO | 9508348 A1 | 3/1995 |
| WO | 9629094 A1 | 9/1996 |
| WO | 9728267 A1 | 8/1997 |
| WO | 9842721 A1 | 10/1998 |
| WO | 9858668 A2 | 12/1998 |
| WO | 0061761 A2 | 10/2000 |
| WO | 0172337 A1 | 10/2001 |
| WO | 0198334 A2 | 12/2001 |
| WO | 02053761 A2 | 7/2002 |
| WO | 02083855 A2 | 10/2002 |
| WO | 02091998 A2 | 11/2002 |
| WO | 03054007 A2 | 7/2003 |
| WO | 2004081515 A2 | 9/2004 |
| WO | 2004083251 A2 | 9/2004 |

OTHER PUBLICATIONS

International Search Report and Written Opinion dated Apr. 17, 2015 for related International Application No. PCT/US2014/071901.

Baraldo et al. "N19 Polyepitope as a Carrier for Enhanced Immunogenicity and Protective Efficacy of Meningococcal Conjugate Vaccines" Infection and Immunity, 72(8):4884-4887 (2004).

Barber et al. "CD4 T Cells Promote Rather than Control Tuberculosis in the Absence of PD-1-Mediated Inhibition" Journal of Immunology, 186(3):1598-1607 (2011).

Ben-Yedidia et al. "Effect of pre-existing carrier immunity on the efficacy of synthetic influenza vaccine" Immunology Letters, 64(1):9-15 (1998) (Abstract only).

Briles et al. "Strong Association between Capsular Type and Virulence for Mice among Human Isolates of *Streptococcus pneumoniae*" Infection and Immunity, 60(1):111-116 (1992).

Briles et al. "Mouse IgG3 antibodies are highly protective against infection with *Streptococcus pneumoniae*" Nature, 294:88-90 (1981) (Abstract only).

Brown et al. "Role of PD-1 in regulating acute infections" Current Opinion in Immunology, 22(3):397-401 (2010).

Chu et al. "Further Studies on the Immunogenicity of Haemophilus influenzae Type b and Pneumococcal Type 6A Polysaccharide-Protein Conjugates" Infection and Immunity, 40(1):245-256 (1983).

Deenick et al. "Switching to IgG3, IgG2b, and IgA Is Division Linked and Independent, Revealing a Stochastic Framework for Describing Differentiation" The Journal of Immunology, 163:4707-4714 (1999).

Falugi et al. "Rationally designed strings of promiscuous CD4(+) T cell epitopes provide help to Haemophilus influenzae type b oligosaccharide: a model for new conjugate vaccines" European Journal of Immunology, 31 (12):3816-3824 (2001).

Gonzalez-Fernandez et al. "Immune responses to polysaccharides: lessons from humans and mice" Vaccine, 26:292-300 (2008).

Good-Jacobson et al. "PD-1 regulates germinal center B cell survival and the formation and affinity of long-lived plasma cells" Nature Immunology, 11(6):535-542 (2010).

Haas et al. "Aging Promotes B-1b Cell Responses to Native, but Not Protein-Conjugated, Pneumococcal Polysaccharides: Implications for Vaccine Protection in Older Adults" The Journal of Infectious Diseases, 209(1):87-97 (2014).

Haas et al. "B-1a and B-1b cells exhibit distinct developmental requirements and have unique functional roles in innate and adaptive immunity to S. pneumoniae" Immunity, 23(1):7-18 (2005).

Haas et al. "CD22 Ligand Binding Regulates Normal and Malignant B Lymphocyte Survival In Vivo" Journal of Immunology, 177(5):3063-3073 (2006).

Huang et al. "PD-1 expression by macrophages plays a pathologic role in altering microbial clearance and the innate inflammatory response to sepsis" Proceedings of the National Academy of Sciences USA, 106(15):6303-6308 (2009).

Kadioglu et al. "The role of *Streptococcus pneumoniae* virulence factors in host respiratory colonization and disease" Nature Reviews Microbiology, 6:288-301 (2008).

Kalka-Moll et al. "Zwitterionic Polysaccharides Stimulate T Cells by MHC Class II-Dependent Interactions" Journal of Immunology, 169(11):6149-6153 (2002).

Kawamoto et al. "The Inhibitory Receptor PD-1 Regulates IgA Selection and Bacterial Composition in the Gut" Science, 336(6080):485-489 (2012).

Keir et al. "PD-1 and Its Ligands in Tolerance and Immunity" Annual Review of Immunology, 26:677-704 (2008).

Kuo et al. "Characterization of a Recombinant Pneumolysin and Its Use as a Protein Carrier for Pneumococcal Type 18C Conjugate Vaccines" Infection and Immunity, 63(7):2706-2713 (1995).

Latchman et al. "PD-L2 is a second ligand for PD-1 and inhibits T cell activation" Nature Immunology, 2(3):261-268 (2001).

Lazar-Molnar et al. "Programmed death-1 (PD-1)-deficient mice are extraordinarily sensitive to tuberculosis" Proceedings of the National Academy of Sciences USA, 107(30):13402-13407 (2010).

Maruya et al. "Impaired selection of IgA and intestinal dysbiosis associated with PD-1-deficiency" Gut Microbes, 4 (2):165-171 (2013).

Mclay et al. "γ3 Gene-Disrupted Mice Selectively Deficient in the Dominant IgG Subclass Made to Bacterial Polysaccharides" J. Immunology, 168:3437-3443 (2002).

NCBI Reference Sequence: NP_001254635.1 "programmed cell death 1 ligand 1 isoform b precursor [*Homo sapiens*]" www.ncbi.nlm.nih.gov (3 pages) (Sep. 12, 2021).

NCBI Reference Sequence: NP_005009.2 "programmed cell death protein 1 precursor [*Homo sapiens*]" www.ncbi.nlm.nih.gov (4 pages) (Sep. 12, 2021).

NCBI Reference Sequence: NP_079515.2 "programmed cell death 1 ligand 2 precursor [*Homo sapiens*]" www.ncbi.nlm.nih.gov (3 pages) (Aug. 2, 2021).

Nishimura et al. "Immunological studies on PD-1 deficient mice: implication of PD-1 as a negative regulator for B cell responses" International Immunology, 10(10):1563-1572 (1998).

Okazaki et al. "A rheostat for immune responses: the unique properties of PD-1 and their advantages for clinical application" Nature Immunology, 14(12):1212-1218 (2013).

Romero-Steiner et al. "Use of Opsonophagocytosis for Serological Evaluation of Pneumococcal Vaccines" Clinical and Vaccine Immunology, 13(2):165-169 (2006).

Rush et al. "Expression of activation-induced cytidine deaminase is regulated by cell division, providing a mechanistic basis for division-linked class switch recombination" Proceedings of the National Academy of Sciences USA, 102 (37):13242-13247 (2005).

(56) References Cited

OTHER PUBLICATIONS

Tian et al. "Efficacy of Opsonic and Nonopsonic Serotype 3 Pneumococcal Capsular Polysaccharide-Specific Monoclonal Antibodies against Intranasal Challenge with *Streptococcus pneumoniae* in Mice" Infection and Immunity, 77(4):1502-1513 (2009).

Titanji et al. "Acute depletion of activated memory B cells involves the PD-1 pathway in rapidly progressing SIV-infected macaques" The Journal of Clinical Investigation, 120(11):3878-3890 (2010).

Uchida et al. "Diphtheria Toxin and Related Proteins" The Journal of Biological Chemistry, 248(11):3838-3844 (1973).

Wang et al. "Immunobiology of Cancer Therapies Targeting CD137 and B7-H1/PD-1 Cosignal Pathways" Current Topics in Microbiology and Immunology, 344:245-267 (2011).

Weber et al. "A Serotype 3 Pneumococcal Capsular Polysaccharide-Specific Monoclonal Antibody Requires Fc gamma Receptor III and Macrophages to Mediate Protection against Pneumococcal Pneumonia in Mice" Infection and Immunity, 80(4):1314-1322 (2012).

Yammani et al. "Primate B-1 Cells Generate Antigen-Specific B Cell Responses to T Cell-Independent Type 2 Antigens" Journal of Immunology, 190:3100-3108 (2013).

Yao et al. "PD-1 on dendritic cells impedes innate immunity against bacterial infection" Blood, 113:5811-5818 (2009).

Yin et al. "Effect of various adjuvants on the antibody response of mice to pneumococcal polysaccharides" Journal of Biological Response Modifiers, 8:190-205 (1989) (Abstract only).

Zhong et al. "Suppression of expression and function of negative immune regulator PD-1 by certain pattern recognition and cytokine receptor signals associated with immune system danger" International Immunology, 16 (8):1181-1188 (2004).

Haas et al. "Complement Receptors CD21/35 Link Innate and Protective Immunity during *Streptococcus pneumoniae* Infection by Regulating IgG3 Antibody Responses" Immunity, 17:713-723 (2002).

Mckay et al. "PD-1 Suppresses Protective Immunity to *Streptococcus pneumoniae* through a B Cell-Intrinsic Mechanism" The Journal of Immunology, 194:2289-2299 (2015).

\* cited by examiner

SEQUENCE LISTING

```
<160> NUMBER OF SEQ ID NOS: 3

<210> SEQ ID NO 1
<211> LENGTH: 288
<212> TYPE: PRT
<213> ORGANISM: Homo sapiens

<400> SEQUENCE: 1

Met Gln Ile Pro Gln Ala Pro Trp Pro Val Val Trp Ala Val Leu Gln
 1               5                  10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
```

```
            50                  55                  60
Leu Asn Trp Tyr Arg Met Ser Pro Ser Asn Gln Thr Asp Lys Leu Ala
 65                  70                  75                  80

Ala Phe Pro Glu Asp Arg Ser Gln Pro Gly Gln Asp Cys Arg Phe Arg
                 85                  90                  95

Val Thr Gln Leu Pro Asn Gly Arg Asp Phe His Met Ser Val Val Arg
             100                 105                 110

Ala Arg Arg Asn Asp Ser Gly Thr Tyr Leu Cys Gly Ala Ile Ser Leu
             115                 120                 125

Ala Pro Lys Ala Gln Ile Lys Glu Ser Leu Arg Ala Glu Leu Arg Val
         130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                 165                 170                 175

Leu Leu Gly Ser Leu Val Leu Leu Val Trp Val Leu Ala Val Ile Cys
             180                 185                 190

Ser Arg Ala Ala Arg Gly Thr Ile Gly Ala Arg Arg Thr Gly Gln Pro
         195                 200                 205

Leu Lys Glu Asp Pro Ser Ala Val Pro Val Phe Ser Val Asp Tyr Gly
210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                 245                 250                 255

Met Gly Thr Ser Ser Pro Ala Arg Arg Gly Ser Ala Asp Gly Pro Arg
             260                 265                 270

Ser Ala Gln Pro Leu Arg Pro Glu Asp Gly His Cys Ser Trp Pro Leu
         275                 280                 285
```

<210> SEQ ID NO 2
<211> LENGTH: 176
<212> TYPE: PRT
<213> ORGANISM: Homo sapiens

<400> SEQUENCE: 2

```
Met Arg Ile Phe Ala Val Phe Ile Phe Met Thr Tyr Trp His Leu Leu
 1               5                  10                  15

Asn Ala Pro Tyr Asn Lys Ile Asn Gln Arg Ile Leu Val Val Asp Pro
                 20                  25                  30

Val Thr Ser Glu His Glu Leu Thr Cys Gln Ala Glu Gly Tyr Pro Lys
             35                  40                  45

Ala Glu Val Ile Trp Thr Ser Ser Asp His Gln Val Leu Ser Gly Lys
         50                  55                  60

Thr Thr Thr Thr Asn Ser Lys Arg Glu Glu Lys Leu Phe Asn Val Thr
 65                  70                  75                  80

Ser Thr Leu Arg Ile Asn Thr Thr Thr Asn Glu Ile Phe Tyr Cys Thr
                 85                  90                  95

Phe Arg Arg Leu Asp Pro Glu Glu Asn His Thr Ala Glu Leu Val Ile
             100                 105                 110

Pro Glu Leu Pro Leu Ala His Pro Pro Asn Glu Arg Thr His Leu Val
         115                 120                 125

Ile Leu Gly Ala Ile Leu Leu Cys Leu Gly Val Ala Leu Thr Phe Ile
     130                 135                 140
```

```
Phe Arg Leu Arg Lys Gly Arg Met Met Asp Val Lys Lys Cys Gly Ile
145                 150                 155                 160

Gln Asp Thr Asn Ser Lys Lys Gln Ser Asp Thr His Leu Glu Glu Thr
                165                 170                 175

<210> SEQ ID NO 3
<211> LENGTH: 273
<212> TYPE: PRT
<213> ORGANISM: Homo sapiens

<400> SEQUENCE: 3

Met Ile Phe Leu Leu Leu Met Leu Ser Leu Glu Leu Gln Leu His Gln
1               5                   10                  15

Ile Ala Ala Leu Phe Thr Val Thr Val Pro Lys Glu Leu Tyr Ile Ile
                20                  25                  30

Glu His Gly Ser Asn Val Thr Leu Glu Cys Asn Phe Asp Thr Gly Ser
            35                  40                  45

His Val Asn Leu Gly Ala Ile Thr Ala Ser Leu Gln Lys Val Glu Asn
        50                  55                  60

Asp Thr Ser Pro His Arg Glu Arg Ala Thr Leu Leu Glu Glu Gln Leu
65                  70                  75                  80

Pro Leu Gly Lys Ala Ser Phe His Ile Pro Gln Val Gln Val Arg Asp
                85                  90                  95

Glu Gly Gln Tyr Gln Cys Ile Ile Ile Tyr Gly Val Ala Trp Asp Tyr
            100                 105                 110

Lys Tyr Leu Thr Leu Lys Val Lys Ala Ser Tyr Arg Lys Ile Asn Thr
        115                 120                 125

His Ile Leu Lys Val Pro Glu Thr Asp Glu Val Glu Leu Thr Cys Gln
    130                 135                 140

Ala Thr Gly Tyr Pro Leu Ala Glu Val Ser Trp Pro Asn Val Ser Val
145                 150                 155                 160

Pro Ala Asn Thr Ser His Ser Arg Thr Pro Glu Gly Leu Tyr Gln Val
                165                 170                 175

Thr Ser Val Leu Arg Leu Lys Pro Pro Pro Gly Arg Asn Phe Ser Cys
            180                 185                 190

Val Phe Trp Asn Thr His Val Arg Glu Leu Thr Leu Ala Ser Ile Asp
        195                 200                 205

Leu Gln Ser Gln Met Glu Pro Arg Thr His Pro Thr Trp Leu Leu His
    210                 215                 220

Ile Phe Ile Pro Phe Cys Ile Ile Ala Phe Ile Phe Ile Ala Thr Val
225                 230                 235                 240

Ile Ala Leu Arg Lys Gln Leu Cys Gln Lys Leu Tyr Ser Ser Lys Asp
                245                 250                 255

Thr Thr Lys Arg Pro Val Thr Thr Thr Lys Arg Glu Val Asn Ser Ala
            260                 265                 270

Ile
```

METHODS AND COMPOSITIONS FOR INCREASING PROTECTIVE ANTIBODY LEVELS INDUCED BY PNEUMOCOCCAL POLYSACCHARIDE VACCINES

CROSS REFERENCE TO RELATED APPLICATIONS

This application claims the benefit of International Application No. PCT/US2014/071901, filed Dec. 22, 2014, which claims the benefit of U.S. Provisional Application No. 61/919,360, filed Dec. 20, 2013, all of the contents of which are hereby incorporated by reference herein in their entireties.

FEDERALLY SPONSORED RESEARCH OR DEVELOPMENT

This presently disclosed subject matter was made with United States government support under R21AI095800 and AI007401 awarded by the National Institutes of Health (NIH) and P30CA012197 awarded by the National Cancer Institute (NCI). The U.S. government has certain rights in the presently disclosed subject matter.

INCORPORATION-BY-REFERENCE OF MATERIAL SUBMITTED ELECTRONICALLY

This application contains a sequence listing. It has been submitted electronically via EFS-Web as an ASCII text file entitled "131198-00008_ST25.txt". The sequence listing is 6,778 bytes in size, and was created on Dec. 19, 2014. It is hereby incorporated by reference in its entirety.

FIELD OF PRESENTLY DISCLOSED SUBJECT MATTER

The presently disclosed subject matter relates to the fields of pharmacology and medicine, and provides therapeutic methods and compositions for the prevention and treatment of bacterial infections caused by *Streptococcus pneumoniae*.

BACKGROUND

*Streptococcus pneumoniae* is a leading source of morbidity and mortality globally, causing life-threatening diseases including pneumonia, meningitis, and sepsis (Kadioglu et al. (2008) *Nat. Rev. Microbiol.* 6:288-301). Antibodies (Ab) directed against the capsular polysaccharide of the pneumococcus (PPS) play a major role in promoting clearance (Tian et al. (2009) *Infect. Immun.* 77:1502-1513; Weber et al. (2012) *Infect. Immun.* 80:1314-1322). The Pneumovax 23 (PPV23)(Px23) vaccine consisting of 23 native PPS from the most common disease-causing serotypes elicits rapid, persistent pneumococcal polysaccharide (PPS) specific antibody production but induces sub-optimal levels of IgG in humans, even when PPS are conjugated to a carrier protein (Gonzalez-Fernandez et al. (2008) *Vaccine* 26:292-300). Abs of the IgG isotype confer superior protection over IgM and IgA isotypes against pneumococcal infection in mouse studies (Briles et al. (1981) *Nature* 294:88-90; McLay et al. (2002) *J. Immunol.* 168:3437-3443) and thus, eliciting increased PPS-specific IgG levels is a major goal of pneumococcal vaccination in humans (Romero-Steiner et al. (2006) *Clin. Vaccine Immunol.* 13:165-169).

PD-1 is a B7/CD28 superfamily receptor expressed on activated lymphoid and myeloid cells (Keir et al. (2008) *Ann. Rev. Immunol.* 26:677-704; Okazaki et al. (2013) *Nature Immunol.* 14:1212-1218). Upon engagement of its ligands (PDL), B7-H1 (PD-L1) and B7-DC (PD-L2), PD-1 negatively regulates critical signaling events. Recent interest in exploiting the PD-1:PDL regulatory axis for treatment of chronic viral infections, cancer, and autoimmunity is supported by numerous mouse, non-human primate and human studies (Brown et al. (2010) *Curr. Opin. Immunol.* 22:397-401; Keir et al. (2008) *Ann. Rev. Immunol.* 26:677-704; Okazaki et al. (2013) *Nature Immunol.* 14:1212-1218; Wang and Chen (2011) *Curr. Top. Microbiol. Immunol.* 344:245-267). Nonetheless, remarkably little is known about how this immunoregulatory pathway influences the immune response to bacterial infections. Studies with two distinct intracellular bacteria yielded divergent results, with PD-1 suppressing protective responses to *Listeria monocytogenes* via dendritic cell regulation (Yao et al. (2009) *Blood* 113:5811-5818) but promoting survival in response to *Mycobacterium tuberculosis* infection via suppression of excessive inflammation (Barber et al. (2011) *J. Immunol.* 186:1598-1607; Lazar-Molnar et al. (2010) *Proc. Nat. Acad. Sci. U.S.A.* 107:13402-13407). To date, the sole investigation of PD-1 effects on acute extracellular bacteria infection employed a cecal ligation puncture model, wherein PD-1 expression on macrophages was found to promote macrophage dysfunction and lethality due to sepsis (Huang et al. (2009) *Proc. Nat. Acad. Sci. U.S.A.* 106:6303-6308). The potential for PD-1 to regulate immune responses against common bacterial respiratory infections caused by extracellular bacteria has not been explored.

Studies examining PD-1 regulation of T cells have been a major driving force in the development of therapies aimed at treating chronic viral infections, cancer, and autoimmunity. However, relatively little is known regarding how interfering with PD-1:PD-1 ligand interactions influences non-T cells in vivo. In particular, studies examining the role of PD-1 in regulating B cell activity are limited. Antigen-receptor activated B cells express PD-1 (Haas (2011) *J. Immunol.* 187:5183-5195), and in vitro studies support a role for PD-1 in diminishing BCR-induced activation and proliferation (Haas (2011) *J. Immunol.* 187:5183-5195; Nishimura et al. (1998) *Int. Immunol.* 10:1563-1572; Zhong et al. (2004) *Int. Immunol.* 16:1181-1188). In vivo studies support a role for PD-1 expressed by T follicular helper cells, as opposed to B cells in promoting optimal T cell dependent (TD) Ab responses to haptenated chicken gamma globulin. (Good-Jacobson et al. (2010) *Nature Immunol.* 11:535-542). However, PD-1 plays a suppressive role during Ab responses to haptenated Ficoll (Haas (2011) *J. Immunol.* 187:5183-5195; Nishimura et al. (1998) *Int. Immunol.* 10:1563-1572), although it is unclear as to what PD-1-expressing population(s) regulates these responses. To date, no physiological role for B-cell specific PD-1 expression in vivo has been experimentally confirmed, although several in vivo findings suggest PD-1 expression on B cells may be important in determining immune response outcomes (Haas (2011)*J. Immunol.* 187:5183-5195; Titanji et al. (2010) *J. Clin. Invest.* 120:3878-3890).

SUMMARY

The presently disclosed subject matter provides methods and compositions for increasing protective antibody levels induced by pneumococcal polysaccharide vaccines.

In one aspect, the presently disclosed subject matter is directed to a method for increasing protective antibody levels and/or enhancing a protective immune response induced by one or more pneumococcal polysaccharide antigens in a subject in need thereof, the method comprising administering to the subject an effective amount of an agent that inhibits the interaction between a PD-1 ligand and a PD-1 polypeptide. In some aspects, the one or more pneumococcal polysaccharide antigens are capsular polysaccharides from one or more different serotypes of *Streptococcus pneumoniae*, particularly wherein the one or more different serotypes of *Streptococcus pneumoniae* are selected from the group consisting of serotypes 1, 2, 3, 4, 5, 6A, 6B, 7F, 8, 9N, 9V, 10A, 11A, 12F, 14, 15B, 17F, 18C, 19A, 19F, 20, 22F, 23F, and 33F. As described in more detail below, in some aspects the PD-1 polypeptide comprises the amino acid sequence of SEQ ID NO:1 or a functional variant thereof, particularly wherein the functional variant comprises an amino acid sequence at least 90% identical to the amino acid sequence of SEQ ID NO:1. In other aspects, the PD-1 ligand is a PDL1 polypeptide or a functional variant thereof, particularly wherein the functional variant comprises an amino acid sequence at least 90% identical to the amino acid sequence of SEQ ID NO:2. In further aspects, the PD-1 ligand is a PDL2 polypeptide or a functional variant thereof, particularly wherein the functional variant comprises an amino acid sequence at least 90% identical to the amino acid sequence of SEQ ID NO:3. In further aspects, the agent is selected from the group consisting of an anti-PD-1 ligand antibody, a small molecule, a peptide, and a fusion protein.

In a further aspect, the presently disclosed subject matter is directed to a method of treating a bacterial infection caused by *Streptococcus pneumoniae* in a subject in need thereof, the method comprising increasing protective antibody levels induced by one or more pneumococcal polysaccharide antigens in the subject, wherein protective antibody levels are increased by administering to the subject an effective amount of an agent that inhibits the interaction between a PD-1 ligand and a PD-1 polypeptide. In some aspects, the bacterial infection caused by *Streptococcus pneumoniae* is selected from the group consisting of pneumonia, acute sinusitis, otitis media, meningitis, bacteremia, sepsis, osteomyelitis, septic arthritis, endocarditis, peritonitis, pericarditis, cellulitis, and brain abscess. In other aspects, the subject in need thereof is 2 years old or younger, particularly wherein the bacterial infection caused by *Streptococcus pneumoniae* is otitis media. In other aspects, the subject in need thereof is 50 years old or older and/or is immunocompromised, particularly wherein the bacterial infection caused by *Streptococcus pneumoniae* is pneumonia. In some aspects, the one or more pneumococcal polysaccharide antigens are capsular polysaccharides from one or more different serotypes of *Streptococcus pneumoniae*, particularly wherein the one or more different serotypes of *Streptococcus pneumoniae* are selected from the group consisting of serotypes 1, 2, 3, 4, 5, 6A, 6B, 7F, 8, 9N, 9V, 10A, 11A, 12F, 14, 15B, 17F, 18C, 19A, 19F, 20, 22F, 23F, and 33F. As described in more detail below, in some aspects the PD-1 polypeptide comprises the amino acid sequence of SEQ ID NO:1 or a functional variant thereof, particularly wherein the functional variant comprises an amino acid sequence at least 90% identical to the amino acid sequence of SEQ ID NO:1. In other aspects, the PD-1 ligand is a PDL1 polypeptide or a functional variant thereof, particularly wherein the functional variant comprises an amino acid sequence at least 90% identical to the amino acid sequence of SEQ ID NO:2. In further aspects, the PD-1 ligand is a PDL2 polypeptide or a functional variant thereof, particularly wherein the functional variant comprises an amino acid sequence at least 90% identical to the amino acid sequence of SEQ ID NO:3. In further aspects, the agent is selected from the group consisting of an anti-PD-1 ligand antibody, a small molecule, a peptide, and a fusion protein.

In some aspects, the presently disclosed subject matter is directed to an immunogenic composition comprising: a) one or more pneumococcal polysaccharide antigens; b) an effective amount of an agent that inhibits the interaction between a PD-1 ligand and a PD-1 polypeptide; and c) a pharmaceutically acceptable carrier. In some aspects, the one or more pneumococcal polysaccharide antigens are capsular polysaccharides from one or more different serotypes of *Streptococcus pneumoniae*, particularly wherein the one or more different serotypes of *Streptococcus pneumoniae* are selected from the group consisting of serotypes 1, 2, 3, 4, 5, 6A, 6B, 7F, 8, 9N, 9V, 10A, 11A, 12F, 14, 15B, 17F, 18C, 19A, 19F, 20, 22F, 23F, and 33F. In some aspects the PD-1 polypeptide comprises the amino acid sequence of SEQ ID NO:1 or a functional variant thereof, particularly wherein the functional variant comprises an amino acid sequence at least 90% identical to the amino acid sequence of SEQ ID NO:1. In other aspects, the PD-1 ligand is a PDL1 polypeptide or a functional variant thereof, particularly wherein the functional variant comprises an amino acid sequence at least 90% identical to the amino acid sequence of SEQ ID NO:2. In further aspects, the PD-1 ligand is a PDL2 polypeptide or a functional variant thereof, particularly wherein the functional variant comprises an amino acid sequence at least 90% identical to the amino acid sequence of SEQ ID NO:3. In further aspects, the agent is selected from the group consisting of an anti-PD-1 ligand antibody, a small molecule, a peptide, and a fusion protein. In further aspects, the one or more pneumococcal polysaccharide antigens are conjugated to a carrier protein. In a still further aspect, the immunogenic composition further comprises an adjuvant.

In other aspects, the presently disclosed subject matter is directed to a kit for increasing protective antibody levels induced by one or more pneumococcal polysaccharide antigens in a subject in need thereof, the kit comprising: a) a pneumococcal polysaccharide vaccine comprising one or more pneumococcal polysaccharide antigens; b) an agent that inhibits the interaction between a PD-1 ligand and a PD-1 polypeptide; and c) instructions for administration of the pneumococcal polysaccharide vaccine and the agent to the subject. A kit for treating a bacterial infection caused by *Streptococcus pneumoniae* in a subject in need thereof is also provided, the kit comprising: a) a pneumococcal polysaccharide vaccine comprising one or more pneumococcal polysaccharide antigens; b) an agent that inhibits the interaction between a PD-1 ligand and a PD-1 polypeptide; and c) instructions for administration of the pneumococcal polysaccharide vaccine and the agent to the subject.

Certain aspects of the presently disclosed subject matter having been stated herein above, which are addressed in whole or in part by the presently disclosed subject matter, other aspects will become evident as the description proceeds when taken in connection with the accompanying Examples and Figures as best described herein below.

BRIEF DESCRIPTION OF THE FIGURES

Figure 1:
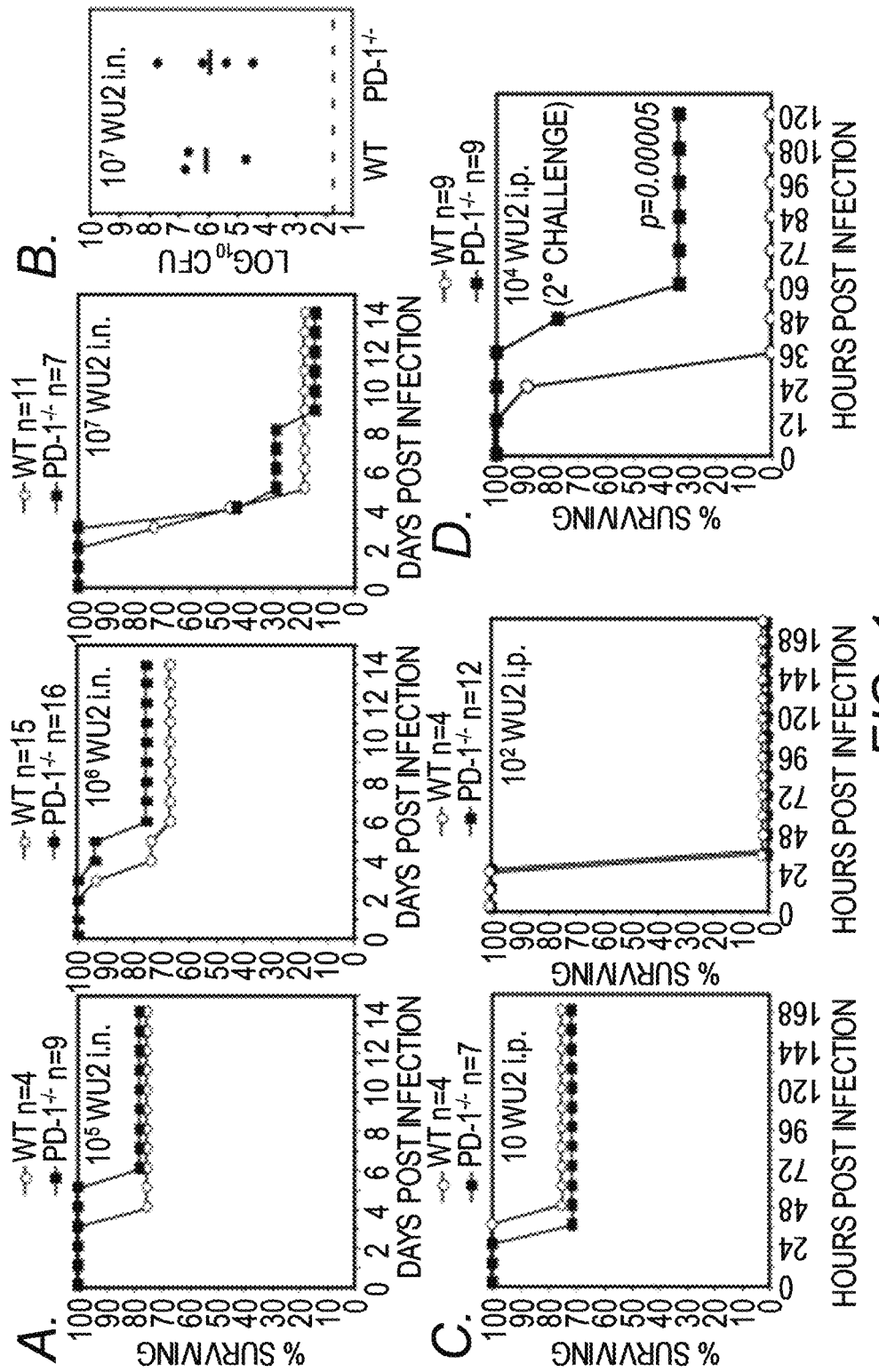
Figure 1:
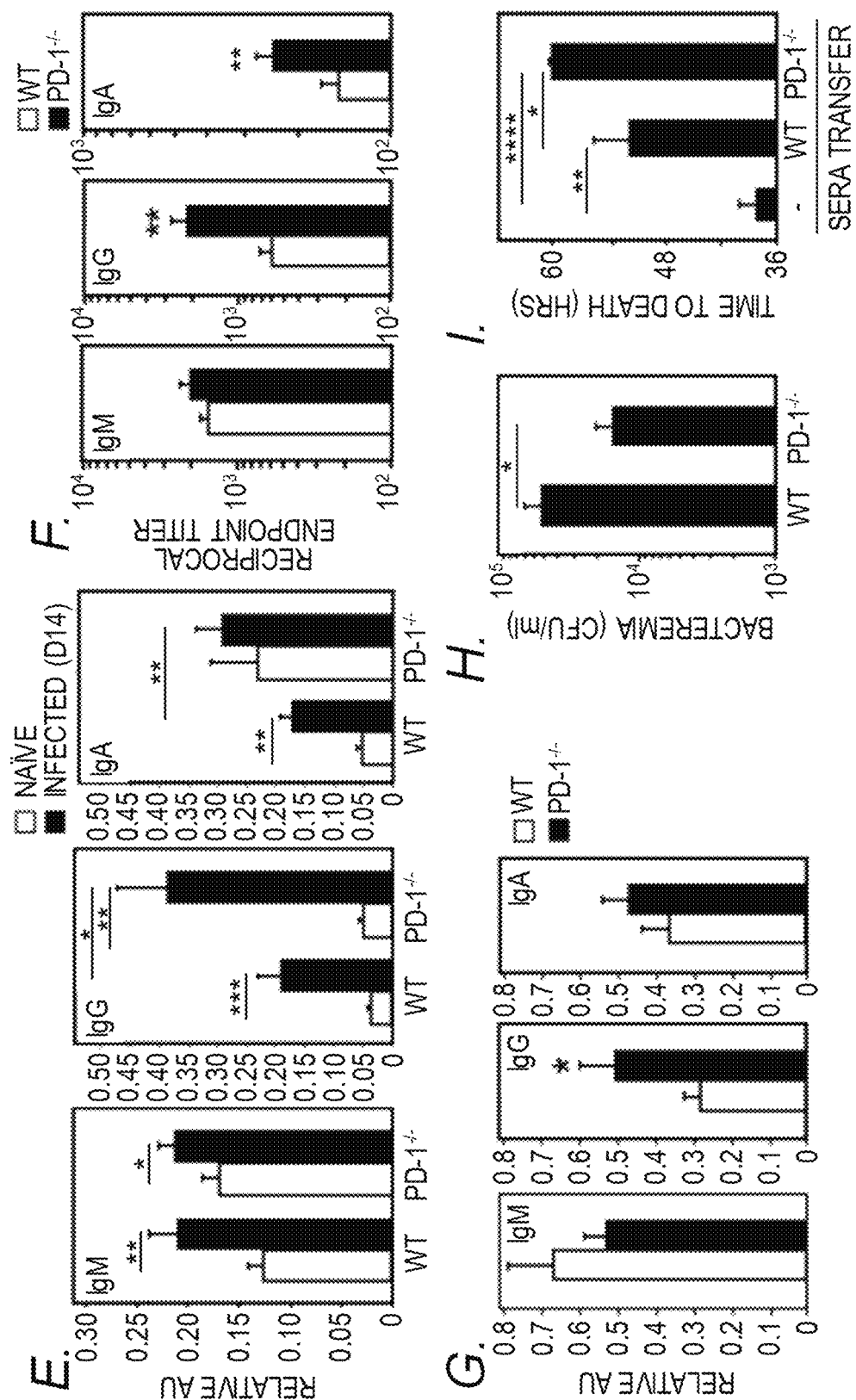
Figure 3:
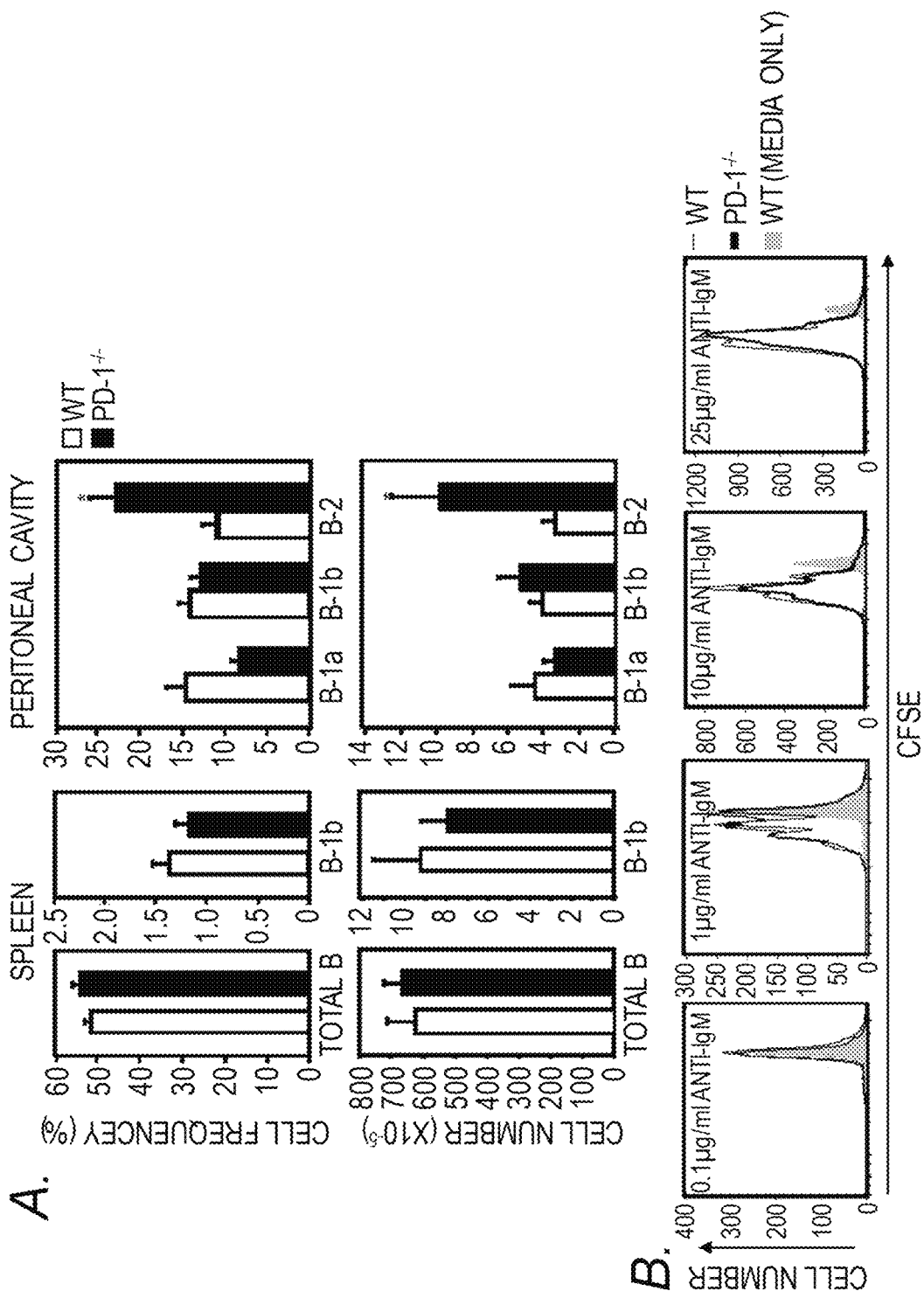

Having thus described the presently disclosed subject matter in general terms, reference will now be made to the accompanying Figures, which are not necessarily drawn to scale, and wherein:

FIGS. 1A-1I show that 1) naïve PD-1$^{-/-}$ mice generate increased capsule-specific IgG following *S. pneumoniae* respiratory infection and are protected against secondary lethal systemic infection and 2) that serum from convalescent PD-1$^{-/-}$ mice provides increased protection against lethal systemic infection in Ab-deficient mice. relative to serum from wild type mice. Wild type (WT) or PD-1$^{-/-}$ mice were infected i.n. (A-B) or i.p. (C) with WU2 and monitored for signs of morbidity requiring euthanasia: A) Kaplan-Meier survival curves for naïve mice infected i.n. with $10^5$, $10^6$, or $10^7$ CFU WU2; B) lung bacterial burdens in WT and PD-1$^{-/-}$ mice 3 days post i.n. infection with $10^7$ CFU WU2; C) Kaplan-Meier survival curves for naïve mice infected i.p. with 10 or $10^2$ CFU WU2; D) survival following secondary systemic pneumococcal infection. Three weeks following primary i.n. infection ($10^6$ CFU WU2), survivors were infected with $10^4$ CFU WU2 i.p., with differences in survival curves assessed by Log-rank analysis (p=0.00005). The experiment was performed 3 times using $10^3$ to $10^4$ CFU WU2 (n=19 wild type mice and n=14 PD-1$^{-/-}$ mice), with differences in survival curves (Log-rank analysis, p=0.002) similar to those shown in (D); E-F) mean (±SEM) PPS3-specific serum IgM, IgG, and IgA levels (arbitrary unit (AU) values in E and reciprocal endpoint titers in F) 14 days post i.n. infection with $10^6$ CFU WU2 (n≥10 mice/group). Results representative of those obtained in 3 separate experiments; (G) Mean (±SEM) PPS3-specific IgM, IgG, and IgA levels in perfused lung homogenates 14 days post i.n. infection with $10^6$ CFU WU2 (n≥11 mice/group); and (H-I) pooled sera from PD-1$^{-/-}$ (n=10) and WT (n=11) mice 14 d post i.n. WU2 infection was administered to μMT mice i.p. concurrently with 200 CFU WU2 i.p. (H) Mean blood bacteria CFU/mL (±SEM) in recipient μMT mice 48 hr post infection. (I) Mean time to death in naïve and recipient μMT mice following i.p. infection (n=6-10 mice/group). Results representative of 2 independent experiments. In E-H, asterisks (*) indicate significant differences in values (p≤0.05, *; p≤0.01, ; p≤0.001, *; p≤0.0001, ****; unpaired Student's t test);

FIGS. 2A-2I show that PD-1 suppresses IgG production against the native, but not protein-conjugated, PPS vaccine: A-C) PPS3-specific serum IgM, IgG, and IgG3 levels in WT and PD-1$^{-/-}$ mice post immunization with: 0.1 μg purified PPS3 (A), an equivalent dose of 1 μg PPS3 contained in the PPV23 vaccine given i.p. (B) or s.c (C); D) PPV23-specific serum IgM (d7) and IgG (d14) levels after immunization with PPV23 containing 0.1 μg or 1 μg of each PPS. In C and D, d14 endpoint dilution titers are also shown; E) PPS3-specific serum IgM and IgG levels in WT and PD-1$^{-/-}$ mice following immunization with an equivalent dose of 0.1 μg PPS3 (CRM$_{197}$-conjugated) contained within Prevnar-13; F) PPS-1, -6A, and -23F-specific serum IgM (d7) and IgG (d14) levels in WT and PD-1$^{-/-}$ mice following immunization with PPV23 containing 0.1 μg or 1 μg each PPS; and G-I) PPS3-specific serum IgM and IgG levels on d0-14 (G), d14 endpoint dilution titers (H), and spleen and bone marrow PPS3-specific Ab-secreting cell frequencies (I; d40) in WT mice that received either PD-1 blocking mAb (RMP1-14) or control rat IgG mAb on d1, 3, and 5 post immunization with purified PPS3. In panels G and I, mice were immunized with 0.1 μg purified PPS3 and in panel H, with 1 μg purified PPS3. (A-I) Mean (±SEM) values are shown (n≥4 mice/group). Asterisks (*) indicate significant differences in values (p≤0.05, *; p≤0.01, ; p≤0.001, *; unpaired Student's t test) between PD-1$^{-/-}$ and WT mice (A-F) or between WT mice receiving PD-1 versus control mAb (G-I);

FIGS. 3A-3B show B cell phenotypes in PD-1$^{-/-}$ mice: A) mean (±SEM) peritoneal and spleen B cell frequencies and numbers in wild type and PD-1$^{-/-}$ mice (n=6 mice/group). B cells were defined as CD19$^+$, B-1a cells as CD19$^+$CD11b$^+$CD5$^+$, B-1b cells as CD19$^+$CD11b$^+$CD5$^-$, and B-2 cells as CD19$^+$CD11b$^-$CD5$^-$. Results are representative of four independent staining experiments obtained for 10-11 mice per genotype; and B) splenic B cell proliferation in response to BCR crosslinking. Purified splenic B cells were CFSE-labeled and stimulated 72 hours with F(ab')2 goat anti-mouse IgM (Jackson Immunoresearch). Cells were stained with 7AAD and 50,000 total events were collected, with 7AAD$^{neg}$ cells analyzed for CFSE loss. Results are representative of those obtained with 3 mice per genotype;

FIGS. 4A-4G show that PD-1 is induced on activated PPS3-specific B cells and PD-1$^{-/-}$ mice have significantly increased PPS3-specific B cell proliferation, IgG switching, and ASC generation. (A-G) Flow cytometric analysis and enumeration of PPS3-binding (Ag-specific) spleen cells from naïve and immune PD-1$^{-/-}$ and WT mice immunized with 0.1 μg purified PPS3: (A) representative flow cytometric analysis of PPS3-specific splenic CD19$^+$ B cells in naïve (left plots) and immune (d3; right plots) mice. Frequencies of gated cells are indicated; (B) mean (±SEM) frequencies and cell numbers of splenic PPS3-specific splenic CD19$^+$ B cells in naïve and d3 immune mice; (C) representative intracellular Ki-67 expression by PPS3-specific splenic CD19$^+$ B cells in d3 immune mice (solid line, left panel). Mean frequencies and numbers (±SEM) of PPS3-specific Ki-67$^+$ cells splenic B cells are graphed; D) BrdU incorporation in PPS3-specific splenic CD19$^+$ B cells 5 days post-immunization following a 5-day BrdU pulse (solid line, left panel). Mean frequencies and numbers (±SEM) of PPS3-specific BrdU$^+$ splenic B cells are indicated; E) representative PPS3-specific splenic CD19$^+$CD138$^+$ B cell staining in d5 immune mice (solid line, left panel). Mean frequencies and numbers (±SEM) of PPS3-specific CD138$^+$ cells splenic B cells are graphed; F) representative IgG3 staining of PPS3-specific splenic CD19$^+$ B cells in immune mice (solid line, left panel). Graphs indicate total mean (±SEM) frequencies and cell numbers of PPS3-specific splenic IgG3$^+$CD19$^+$ B cells; and (G) CD11b expression by PPS3-specific splenic IgG3$^+$CD19$^+$ B cells in immune PD-1$^{-/-}$ mice (solid line). In C, D, F, and G, the dashed histogram indicates mAb isotype control staining (intracellular staining in C and D or extracellular staining in F and G) for PPS3-specific B cells from immune mice. Asterisks (*) in B-F indicate significant differences between WT and PD-1$^{-/-}$ values (p≤0.05, *; p≤0.01, ; p≤0.001, *; n≥3 mice/group). Student's t test was used in B-E. In F, Welch's t-test was used due to unequal variance between groups as determined by F-test.

FIGS. 5A-5I show that B-cell specific PD-1 expression suppresses PPS3-specific IgG responses: A) PD-1 expression on naïve (gray shading) and PPS3-immune (thick solid line) PPS3-specific CD19$^+$ splenic B cells from WT and PD-1$^{-/-}$ mice. The dashed histogram indicates mAb isotype control staining for PPS3-specific B cells from immune mice; B) CD11b expression on PPS3-specific CD19$^+$ (PD-1$^+$ and PD-1$^-$) B cells from WT mice 5 days post immunization (0.1 μg PPS3); C) PD-1 expression levels (mean MFI (±SEM)) on PPS3-specific resting (FSC$^{lo}$TD86$^-$) and activated (FSC$^{hi}$CD86$^+$) splenic B cells in immune (d5) and naïve mice (n=3 mice/group); D) PD-1 staining on PPS3-specific CD19$^+$ FSC$^{hi}$CD86$^+$ splenic B cells from WT and PD-1$^{-/-}$ mice 5 d post immunization. The dashed histogram indicates mAb isotype control staining of PPS3-specific CD19$^+$ FSC$^{hi}$CD86$^+$ splenic B cells from WT mice; E) mean frequency (±SEM) of PPS3-specific resting (FSC$^{lo}$TD86$^-$) and activated (FSC$^{lo}$TD86$^+$) splenic B cells in immune (d5)

and naïve mice expressing PD-1 (n=3 mice/group); F) FSC and CD86 expression by naïve PPS3-specific CD19$^+$ B cells (gray shading), and PD-1$^{neg}$ (thin line) and PD-1$^+$ (thick line) PPS3-specific CD19$^+$ B cells in immune (d5) mice. The dashed histogram indicates mAb isotype control staining; G) mean (±SEM) PPV23-specific serum IgM and IgG levels in µEMT mice that were reconstituted with 4×10$^7$ splenic B cells (i.p. transfer) from WT or PD-1$^{-/-}$ mice and immunized with PPV23 containing 0.1 µg each PPS two days post adoptive transfer (n=6 mice/group; pooled results from 2 experiments). Pre-immune (d2 post transfer) and d7 immune (d9 post transfer) values are shown; H) total serum IgM and IgG concentrations in µEMT mice 9 days post reconstitution; and I) mean (±SEM) spleen B cell and peritoneal cavity total B cell and B-1b cell frequencies in µEMT mice 2 weeks post reconstitution. Asterisks (*) indicate significant differences between values (p≤0.05, *; p≤0.01, **; unpaired Student's t test, n≥3 mice/group);

FIGS. 6A-6D show that PD-1 regulates Ag-specific B-1b cell proliferation in vivo via B cell-intrinsic expression. Allotype-marked (CD45.1$^+$) peritoneal B-1b cells from B1-8$^{hi}$ IgH knock-in mice were CFSE-labeled and transferred into the peritoneal cavities of CD45.2$^+$ PD-1$^{-/-}$ mice (5×10$^5$/mouse). The next day, mice (4-5/group) were immunized i.p. with 0.1 mg NP-Ficoll (d0). On d1, mice received 200 µg PD-1 blocking mAb (RMP1-14) or isotype control mAb i.p. NP-specific ($\lambda^+$CD45.1$^+$) CD19$^+$ B cells were analyzed by flow cytometry at d3 post-immunization: A) expression of CD11b and PD-1 by dividing ($\lambda^+$) and non-dividing ($\lambda^-$) CD45.1+CD19$^+$ cells and IgG3$^+$ cells (for CD11b) recovered from the peritoneal cavities of recipient mice. Gray shaded histograms indicate isotype control staining for the dividing ($\lambda$+) population; B-C) increased IgG3$^+$ $\lambda^+$CD45.1$^+$ peritoneal B-1b cell frequencies are found in mice treated with PD-1 blockade (B) and these IgG3$^+$ cells show increased CFSE loss relative to mice treated with control mAb (C); and D) division in the adoptively transferred CD45.1$^+$ B cell pool is increased in the spleens of mice treated with PD-1 blockade as evidenced by increased CFSE loss (left panel) and increased proliferation indices (middle panel). Significantly increased CFSE loss is also observed among high affinity 2, 1$^+$ NP-specific B cells (right panel);

FIGS. 7A-7D show that naïve B7-H1$^{-/-}$ and B7-DC$^{-/-}$ mice exhibit normal survival kinetics and similar PPS3-specific Ig levels following *S. pneumoniae* respiratory infection. C57BL/6 WT, B7-H1$^{-/-}$, and B7-DC$^{-/-}$ mice were challenged i.n. with 10$^5$, 10$^6$, or 10$^7$ CFU WU2 and monitored for signs of morbidity requiring euthanasia: A) Kaplan-Meier survival curves are shown. No significant differences were found based on Log-rank analysis; B) lung bacterial burdens 3 days post challenge with 10$^7$ CFU WU2; and C-D) PPS3-specific serum IgM, IgG, and IgA levels in (C) B7-H1$^{-/-}$ and (D) B7-DC$^{-/-}$ mice 14 days post infection with 10$^6$ CFU WU2 (n≥5 mice/group);

FIGS. 8A-8I show that B7-H1 and B7-DC are both required for suppression of PPS-specific IgG responses: A-B) PPS3-specific serum IgM and IgG levels in B7-H1$^{-/-}$ (A) and B7-DC (B) mice 0, 7, and 14 days post PPV23 immunization (~0.1 µg PPS3) relative to WT mice; C-D) PPS3-specific serum IgM and IgG levels in B7-H1$^{-/-}$ (C) and B7-DC$^{-/-}$ (D) mice following immunization with Prevnar-13 (~0.1 µg PPS3); E-F) TNP-specific serum IgM and IgG levels in WT, PD-1$^{-/-}$, B7-H1$^{-/-}$, and B7-DC$^{-/-}$ mice following TNP-Ficoll immunization; G) TNP-specific serum IgM, IgG, and IgG3 levels in WT mice administered blocking mAbs against B7-H1, B7-DC, PD-1 or rat IgG control mAbs following TNP-Ficoll immunization; and H-I) PPS3-specific IgM and IgG levels in WT mice administered single blocking mAbs against B7-H1 or B7-DC (H) or blocking mAbs against both B7-H1 and B7-DC (I) following PPV23 immunization. A-I) Mean values (±SEM; n≥4 mice/group) are shown. Asterisks (*) indicate significant differences in values between knockout mice and WT mice (A and E) or WT mice receiving control mAbs and functional PD-1/PDL blocking mAbs (G and I) (p≤0.05, *; p≤0.01, ; p≤0.001, *; unpaired Student's t test); and FIGS. 9A-9G show that PPS immunization in the context of PD-1 deficiency or blockade significantly increases survival against lethal respiratory *S. pneumoniae* infection and is dependent on B cell-intrinsic PD-1 expression: A-C) purified PPS3-immunized WT, PD-1$^{-/-}$, B7-H1$^{-/-}$, and B7-DC$^{-/-}$ mice were challenged with a lethal i.n. dose (1×10$^7$ CFU) of WU2 28 days following immunization. A-B) Survival analysis shows a significant difference between PD-1$^{-/-}$ and WT mice (p=0.05; Fisher's Exact test). B-C) Total lung (B and C) and blood (per mL; B only) CFU 8 days post challenge. Asterisks (*) indicate significant differences in CFU between WT and PD-1$^{-/-}$ mice (p≤0.05, *; p≤0.01, **; Student's t test); D) survival in Prevnar-13-immunized WT and PD-1$^{-/-}$ mice challenged i.n. with 10$^7$ CFU WU2 28 days following immunization; E) survival in WT mice given PD-1 blocking or control mAbs at the time of purified PPS3 immunization (as described in FIG. 8 legend) and challenged i.n. with 1×10$^7$ CFU WU2 28 days following immunization (n=8-9 mice/group). Survival curves were significantly different as determined by Log-rank analysis (p=0.03); and F-G) reconstitution of µMT mice with B cells from PD-1$^{-/-}$ mice yields significantly increased PPS-specific IgG responses and significantly increases protection against infection. Control µMT mice (n=10), and µMT mice reconstituted with 2×10$^7$ wild type (n=11) or PD-1$^{-/-}$ (n=6) spleen B cells, were immunized on d1 as in FIG. 5; F) PPV23-specific IgM and IgG reciprocal endpoint dilution titers were determined for d7 sera and were defined as the dilution yielding an OD$_{405nm}$ value 3-fold higher than values for non-reconstituted µMT mice. (*p=0.04, unpaired Student's t test); and G) Mice were infected i.p. with 200 CFU WU2 on d8, with differences in overall survival assessed by Fisher's Exact test.

DETAILED DESCRIPTION

The presently disclosed subject matter now will be described more fully hereinafter with reference to the accompanying Figures, in which some, but not all embodiments of the presently disclosed subject matter are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

The presently disclosed subject matter is directed to methods and compositions for increasing protective antibody levels induced by pneumococcal polysaccharide vaccines. As described more fully below, the presently disclosed subject matter relates to the finding that inhibiting the interaction of PD-1 with its ligands significantly increases IgG levels to polysaccharide antigens. Specifically, inhibiting the interaction of PD-1 with its ligands, particularly PDL1 and PDL2, significantly increased the levels of protective IgG antibodies produced against the polysaccharide antigens in a multivalent pneumococcal polysaccharide vaccine. Not only were IgG levels significantly increased against the total multivalent pneumococcal polysaccharide vaccine (the Pneumovax®23 vaccine), but IgG levels were significantly increased against individual capsular polysaccharide serotypes found in the multivalent pneumococcal polysaccharide vaccine (e.g., serotypes 1, 3, 6A, and 23F). Although a prior study showed that blocking PD-1 from interacting with its ligands significantly increased IgG levels against a hapten 2,4,6-trinitrophenol (TNP) that was attached to the polysaccharide Ficoll (Haas (2011) *J. Immunol.* 187:5183-95), in that study Ficoll simply functioned as a backbone for display of the small hapten molecule as opposed to being an antigenic target itself.

Surprisingly, PD-1 deficiency has the opposite effect on IgG responses to protein antigens (i.e., in mice lacking PD-1, IgG responses to protein antigens are significantly decreased; Good-Jacobson, K. L., et al, 2010, *Nat. Immunol.* 6:535-542). Without being bound by theory, this is thought to be due to the involvement of PD-1-expressing T cells (T follicular helper cells) which support B cell antibody production in response to protein, but not polysaccharide antigens.

I. Methods of Treatment

*Streptococcus pneumoniae*, or pneumococcus, is gram-positive, lancet-shaped cocci, alpha-hemolytic, bile soluble aerotolerant anaerobe and a member of the genus *Streptococcus*. *Streptococcus pneumoniae* is known in medical microbiology as *Pneumococcus*, referring to its morphology and its consistent involvement in pneumococcal pneumonia. *Streptococcus pneumoniae* is a fastidious bacterium, growing best in 5% carbon dioxide and complex medium. Nearly 20% of fresh clinical isolates require fully anaerobic conditions. In almost all cases, growth requires a source of catalase (e.g. blood) to neutralize the large amount of hydrogen peroxide produced by the bacteria. In complex media containing blood, at 37° C., the bacterium has a doubling time of 20-30 minutes.

*Streptococcus pneumoniae* are common inhabitants of the respiratory tract, and have been isolated from the nasopharynx of 5% to 70% of normal adults. Rates of asymptomatic carriage vary with age, environment, and the presence of upper respiratory infections, with identified carrier rates of only 5%-10% in adults without children, 27% to 58% of students and residents in schools and orphanages, and as many as 50% to 60% of service personnel on military installations. The duration of carriage varies and is generally longer in children than adults (reviewed in Epidemiology and Prevention of Vaccine-Preventable Diseases, 12th Edition-Second Printing, The Pink Book: Course Textbook, Centers for Disease Control and Prevention (May 2012)).

As with many natural flora, *Streptococcus pneumoniae* can become pathogenic under the right conditions (e.g., if the immune system of the host is suppressed). *Streptococcus pneumoniae* is currently the leading cause of invasive bacterial disease in children and the elderly. In spite of its name, *Streptococcus pneumoniae* causes many types of pneumococcal infections other than pneumonia, including acute sinusitis, otitis media, meningitis, bacteremia, sepsis, osteomyelitis, septic arthritis, endocarditis, peritonitis, pericarditis, cellulitis, and brain abscess.

Antibiotics are the treatment of choice for *Streptococcus pneumoniae* infection, with ventilation (oxygen supplement) as supportive therapy of bacterial pneumonia. The antibiotic choice depends on the microorganisms most commonly causing pneumonia in the geographical region, as well as the nature of the specific organism, the immune status and underlying health of the individual, the severity of infection, and prior treatment history. In the United Kingdom, amoxicillin is used as first-line therapy in the vast majority of patients who acquire pneumonia in the community, sometimes with added clarithromycin. In North America, where the "atypical" forms of community-acquired pneumonia are becoming more common, clarithromycin, azithromycin, or fluoroquinolones as single therapy, have displaced the amoxicillin as first-line therapy. In hospitalized individuals or those with immune deficiencies, local guidelines determine the selection of antibiotics. These antibiotics are typically given through an intravenous line. Specifically, *Streptococcus pneumoniae* is treated with amoxicillin (or erythromycin in patients allergic to penicillin), and with cefuroxime and erythromycin in severe cases.

A growing concern in *Streptococcus pneumoniae* therapy is the resistance of strains many to penicillin and other beta-lactams (like amoxicillin), which is increasing worldwide. The major mechanism of resistance involves the introduction of mutations in genes encoding penicillin-binding proteins. This development complicates treatment immensely, and also adds unnecessary cost when therapies fail.

The ability of *Streptococcus pneumoniae* to resist the major mechanism of clearance of the organism from the bloodstream (i.e. opsonophagocytosis) requires expression of the major virulence factor of the organism: a polysaccharide capsule. Pneumococcal capsular polysaccharides are responsible for its anti-phagocytic properties and inhibition of adherence to host cells, which is a critical step in carriage and possibly later aspects in the pathogenesis of disease. Approximately ninety different pneumococci serotypes have been identified, and each serotype corresponds to a different chemical composition of the capsule.

*Streptococcus pneumoniae* capsular polysaccharides are currently used as an antigen in pneumococcal vaccines. Pneumococcal capsular polysaccharide vaccines have been licensed since 1977. Merck's 23-valent unconjugated vaccine PNEUMOVAX® 23) is designed to provide coverage against approximately 90% of the most frequently reported capsular polysaccharide isolates, and comprises serotypes 1, 2, 3, 4, 5, 6B, 7F, 8, 9N, 9V, 10A, 11A, 12F, 14, 15B, 17F, 18C, 19F, 19A, 20, 22F, 23F, and 33F. However, PNEUMOVAX® 23 does not induce immune memory, and therefore is not effective in children below 2 years of age. Advances in conjugation technology have led to conjugation of polysaccharides to carrier proteins leading to a T-cell response, thus enabling polysaccharide conjugate vaccines with efficacy in treating younger children. For example, the 7-valent Prevnar® and 13-valent Prevnar 13° manufactured by Wyeth Pharmaceuticals Inc. and marketed by Pfizer Inc. each comprise, respectively, serotypes 4, 6B, 9V, 14, 18C, 19F, and 23F, and serotypes 1, 3, 4, 5, 6A, 6B, 7F, 9V, 14, 18C, 19A, 19F, and 23F. The 10-valent Synflorix® produced by GlaxoSmithKline, PLC comprises serotypes 1, 4, 5, 6B, 7F, 9V, 14, 18C, 19F, and 23F.

Accordingly, in one embodiment, the presently disclosed subject matter is directed to a method for increasing protective antibody levels and/or enhancing a protective immune response induced by one or more pneumococcal polysaccharide antigens in a subject in need thereof, the method comprising administering to the subject an effective amount of an agent that inhibits the interaction between a PD-1 ligand and a PD-1 polypeptide. In some embodiments, the one or more pneumococcal polysaccharide antigens are capsular polysaccharides from one or more different serotypes of *Streptococcus pneumoniae*, particularly wherein the one or more different serotypes of *Streptococcus pneumoniae* are selected from the group consisting of serotypes 1, 2, 3, 4, 5, 6A, 6B, 7F, 8, 9N, 9V, 10A, 11A, 12F, 14, 15B, 17F, 18C, 19A, 19F, 20, 22F, 23F, and 33F. As described in more detail below, in some embodiments the PD-1 polypeptide comprises the amino acid sequence of SEQ ID NO:1 or a functional variant thereof, particularly wherein the functional variant comprises an amino acid sequence at least 90% identical to the amino acid sequence of SEQ ID NO:1. In other embodiments, the PD-1 ligand is PDL1 or PDL2. In further embodiments, the agent is an anti-PD-1 ligand antibody or a small molecule.

In a further embodiment, the presently disclosed subject matter is directed to a method of treating a bacterial infection caused by *Streptococcus pneumonia* in a subject in need thereof, the method comprising increasing protective antibody levels induced by one or more pneumococcal polysaccharide antigens in the subject, wherein protective antibody levels are increased by administering to the subject an effective amount of an agent that inhibits the interaction between a PD-1 ligand and a PD-1 polypeptide. In some embodiments, the bacterial infection caused by *Streptococcus pneumoniae* is selected from the group consisting of pneumonia, acute sinusitis, otitis media, meningitis, bacteremia, sepsis, osteomyelitis, septic arthritis, endocarditis, peritonitis, pericarditis, cellulitis, and brain abscess. In other embodiments, the subject in need thereof is 2 years old or younger, particularly wherein the bacterial infection caused by *Streptococcus pneumoniae* is Otitis media. In other embodiments, the subject in need thereof is 50 years old or older and/or is immunocompromised, particularly wherein the bacterial infection caused by *Streptococcus pneumonia* is pneumonia. In some embodiments, the one or more pneumococcal polysaccharide antigens are capsular polysaccharides from one or more different serotypes of *Streptococcus pneumoniae*, particularly wherein the one or more different serotypes of *Streptococcus pneumoniae* are selected from the group consisting of serotypes 1, 2, 3, 4, 5, 6A, 6B, 7F, 8, 9N, 9V, 10A, 11A, 12F, 14, 15B, 17F, 18C, 19A, 19F, 20, 22F, 23F, and 33F. As described in more detail below, in some embodiments the PD-1 polypeptide comprises the amino acid sequence of SEQ ID NO:1 or a functional variant thereof, particularly wherein the functional variant comprises an amino acid sequence at least 90% identical to the amino acid sequence of SEQ ID NO:1. In other embodiments, the PD-1 ligand is PDL1 or PDL2. In further embodiments, the agent is an anti-PD-1 ligand antibody or a small molecule.

By "agent" is meant an agent that inhibits the interaction between a PD-1 ligand and a PD-1 polypeptide, as described in more detail below. More generally, the term "therapeutic agent" means a substance that has the potential of affecting the function of an organism. Such an agent may be, for example, a naturally occurring, semi-synthetic, or synthetic agent. For example, the therapeutic agent may be a drug that targets a specific function of an organism. A therapeutic agent may decrease, suppress, attenuate, diminish, arrest, or stabilize the development or progression of disease, disorder, or condition in a host organism.

The term "administering" as used herein refers to contacting at least a cell with an agent and/or polysaccharide antigens as defined herein. This term includes administration of the presently disclosed agents and/or polysaccharide antigens to a subject in which the cell is present, as well as introducing the presently disclosed agents into a medium in which a cell is cultured.

The subject treated by the presently disclosed methods in their many embodiments is desirably a human subject, although it is to be understood that the methods described herein are effective with respect to all vertebrate species, which are intended to be included in the term "subject." Accordingly, a "subject" can include a human subject for medical purposes, such as for the treatment of an existing disease, disorder, condition or the prophylactic treatment for preventing the onset of a disease, disorder, or condition or an animal subject for medical, veterinary purposes, or developmental purposes. Suitable animal subjects include mammals including, but not limited to, primates, e.g., humans, monkeys, apes, gibbons, chimpanzees, orangutans, macaques and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, guinea pigs, and the like. An animal may be a transgenic animal. In some embodiments, the subject is a human including, but not limited to, fetal, neonatal, infant, juvenile, and adult subjects. Further, a "subject" can include a patient afflicted with or suspected of being afflicted with a disease, disorder, or condition. Thus, the terms "subject" and "patient" are used interchangeably herein. Subjects also include animal disease models (e.g., rats or mice used in experiments and the like).

In particular embodiments, the subject is suffering from or susceptible to a disease, disorder, or condition associated with bacterial infection caused by *Streptococcus pneumoniae*.

As used herein, the terms "treat," "treating," "treatment," and the like, are meant to decrease, suppress, attenuate, diminish, arrest, the underlying cause of a disease, disorder, or condition, or to stabilize the development or progression of a disease, disorder, condition, and/or symptoms associated therewith. The terms "treat," "treating," "treatment," and the like, as used herein can refer to curative therapy, prophylactic therapy, and preventative therapy. Treatment according to the presently disclosed methods can result in complete relief or cure from a disease, disorder, or condition, or partial amelioration of one or more symptoms of the disease, disease, or condition, and can be temporary or permanent. The term "treatment" also is intended to encompass prophylaxis, therapy and cure.

As used herein, the terms "prevent," "preventing," "prevention," "prophylactic treatment" and the like refer to reducing the probability of developing a disease, disorder, or condition in a subject, who does not have, but is at risk of or susceptible to developing a disease, disorder, or condition. Thus, in some embodiments, an agent and/or polysaccharide antigen can be administered prophylactically to prevent the onset of a disease, disorder, or condition, or to prevent the recurrence of a disease, disorder, or condition.

The term "effective amount," as in "a therapeutically effective amount," of a therapeutic agent and/or polysaccharide antigen refers to the amount of the agent and/or polysaccharide antigen necessary to elicit the desired biological response. As will be appreciated by those of ordinary skill in this art, the effective amount of an agent and/or polysaccharide antigen may vary depending on such factors as the desired biological endpoint, the agent and/or polysaccharide antigens to be delivered, the composition of the pharmaceutical composition, the target tissue or cell, and the like. More particularly, the term "effective amount" refers to an amount sufficient to produce the desired effect, e.g., to reduce or ameliorate the severity, duration, progression, or onset of a disease, disorder, or condition, or one or more symptoms thereof; prevent the advancement of a disease, disorder, or condition, cause the regression of a disease, disorder, or condition; prevent the recurrence, development, onset or progression of a symptom associated with a disease, disorder, or condition, or enhance or improve the prophylactic or therapeutic effect(s) of another therapy.

In some embodiments, an effective amount of an agent that inhibits the interaction between a PD-1 ligand and a PD-1 polypeptide is an amount that increases protective antibody levels and/or enhances a protective immune response induced by administration of one or more pneumococcal polysaccharide antigens in a subject in need thereof. In any of the above-described methods, administration of one or more agents described herein that inhibit the interaction between a PD-1 ligand and a PD-1 polypeptide results in at least about a 1.1-fold, 1.2-fold, 1.3-fold, 1.4-fold, 1.5-fold, 1.6-fold, 1.7-fold, 1.8-fold, 1.9-fold, 2-fold, 3-fold, 4-fold, 5-fold, 6-fold, 7-fold, 8-fold, 9-fold, 10-fold, 15-fold, 20-fold, 25-fold, 30-fold, 35-fold, 40-fold, 45-fold, 50-fold, 55-fold, 60-fold, 65-fold, 70-fold, 75-fold, 80-fold, 85-fold, 90-fold, 95-fold, or 100-fold increase in protective antibody levels and/or in a protective immune response induced by administration of one or more pneumococcal polysaccharide antigens in a subject in need thereof.

In any of the above-described methods, administration of one or more agents and/or polysaccharide antigens described herein can result in at least about a 10%, 15%, 20%, 25%, 30%, 35%, 40%, 45%, 50%, 55%, 60%, 65%, 70%, 75%, 80%, 85%, 90%, 95%, or even 100% decrease in one or more (e.g., 1, 2, 3, 4, 5, 6, 7, 8, 9, or 10) symptoms of a disease, disorder, or condition associated with bacterial infection caused by *Streptococcus pneumoniae* compared to a subject that is not administered the one or more of the agents and/or polysaccharide antigens described herein.

In any of the above-described methods, administration of one or more agents and/or polysaccharide antigens described herein results in at least about a 10%, 15%, 20%, 25%, 30%, 35%, 40%, 45%, 50%, 55%, 60%, 65%, 70%, 75%, 80%, 85%, 90%, 95%, or even 100% decrease in the likelihood of developing a disease, disorder, or condition associated with bacterial infection caused by *Streptococcus pneumoniae* compared to a control population of subjects that are not administered the one or more of the agents and/or polysaccharide antigens described herein. Alternatively, in any of the above-described methods, administration of one or more agents and/or polysaccharide antigens described herein results in at least about a 1.1-fold, 1.2-fold, 1.3-fold, 1.4-fold, 1.5-fold, 1.6-fold, 1.7-fold, 1.8-fold, 1.9-fold, 2-fold, 3-fold, 4-fold, 5-fold, 6-fold, 7-fold, 8-fold, 9-fold, 10-fold, 15-fold, 20-fold, 25-fold, 30-fold, 35-fold, 40-fold, 45-fold, 50-fold, 55-fold, 60-fold, 65-fold, 70-fold, 75-fold, 80-fold, 85-fold, 90-fold, 95-fold, or 100-fold decrease in the likelihood of developing a disease, disorder, or condition associated with bacterial infection caused by *Streptococcus pneumoniae* compared to a control population of subjects that are not administered the one or more of the agents and/or polysaccharide antigens described herein.

In some embodiments, the presently disclosed agents and/or polysaccharide antigens decrease, suppress, attenuate, diminish, arrest, or stabilize the development or progression of a disease, disorder, or condition, or the activity of a biological pathway, e.g., by at least 10%, 20%, 30%, 40%, 50%, 60%, 70%, 80%, 90%, 95%, 98%, 99%, or even 100% compared to an untreated control subject, cell, or biological pathway. Alternatively, in some embodiments, the presently disclosed agents and/or polysaccharide antigens decrease, suppress, attenuate, diminish, arrest, or stabilize the development or progression of a disease, disorder, or condition, or the activity of a biological pathway, e.g., by at least about a 1.1-fold, 1.2-fold, 1.3-fold, 1.4-fold, 1.5-fold, 1.6-fold, 1.7-fold, 1.8-fold, 1.9-fold, 2-fold, 3-fold, 4-fold, 5-fold, 6-fold, 7-fold, 8-fold, 9-fold, 10-fold, 15-fold, 20-fold, 25-fold, 30-fold, 35-fold, 40-fold, 45-fold, 50-fold, 55-fold, 60-fold, 65-fold, 70-fold, 75-fold, 80-fold, 85-fold, 90-fold, 95-fold, or 100-fold compared to an untreated control subject, cell, or biological pathway. By the term "decrease" is meant to inhibit, suppress, attenuate, diminish, arrest, or stabilize a symptom of a disease, disorder, or condition. It will be appreciated that, although not precluded, treating a disease, disorder or condition does not require that the disease, disorder, condition or symptoms associated therewith be completely eliminated.

As used herein, the term "in combination with" places no limit on the method, mode, form, etc. of the administration. For example, "in combination with" would include, but is not limited to, simultaneous administration of two or more therapeutic agents and/or polysaccharide antigens, alone as single agents and/or polysaccharide antigens, or in a single composition; it would also include sequential administration of two or more therapeutic agents and/or polysaccharide antigens.

In one embodiment of the presently disclosed subject matter, the one or more pneumococcal polysaccharide antigens and the agent that inhibits the interaction between a PD-1 ligand and a PD-1 polypeptide are administered simultaneously to the subject. For example, the one or more pneumococcal polysaccharide antigens and the agent that inhibits the interaction between a PD-1 ligand and a PD-1 polypeptide are delivered in a common dosage form, where the dosage form comprises both the one or more pneumococcal polysaccharide antigens and the agent that inhibits the interaction between a PD-1 ligand and a PD-1 polypeptide. In another example, the one or more pneumococcal polysaccharide antigens and the agent that inhibits the interaction between a PD-1 ligand and a PD-1 polypeptide are delivered in two or more dosage forms that are administered simultaneously, or at approximately the same time (e.g., within less than 30 minutes, or within less than 15 minutes, or within less than 10 minutes, or within less than 5 minutes, or within less than 2 minutes of each other), where at least one dosage form comprises the one or more pneumococcal polysaccharide antigens and another dosage form comprises the agent that inhibits the interaction between a PD-1 ligand and a PD-1 polypeptide.

In further embodiments, the one or more pneumococcal polysaccharide antigens and the agent that inhibits the interaction between a PD-1 ligand and a PD-1 polypeptide are administered sequentially, that is separately in time in a sequential manner, wherein one therapeutic agent is administered first and the other second, or vice versa. Such sequential administration may be close in time or remote in time. For example, the one or more pneumococcal polysaccharide antigens and the agent that inhibits the interaction between a PD-1 ligand and a PD-1 polypeptide can be administered about 30 minutes apart, or about 1 hour apart, or about 2 hours apart, or about 4 hours apart, or about 8 hours apart, or about 12 hours apart, or about 24 hours apart, where the one or more pneumococcal polysaccharide antigens is administered earlier than the agent that inhibits the interaction between a PD-1 ligand and a PD-1 polypeptide, or vice versa, or any period of time during which the agent that inhibits the interaction between a PD-1 ligand and a PD-1 polypeptide remains present in effective amounts in the subject's system to produce an increase in protective antibody levels induced by subsequent administration of the one or more pneumococcal polysaccharide antigens.

In even further embodiments, the methods of the presently disclosed subject matter comprise a "prime/boost" protocol, wherein the priming composition comprises the one or more pneumococcal polysaccharide antigens, and the boosting composition comprises the agent that inhibits the interaction between a PD-1 ligand and a PD-1 polypeptide, wherein the boosting composition is administered to the subject within a period of time following administration of the priming composition to produce an increase in protective antibody levels generated in response to the priming composition. For example, the agent that inhibits the interaction between a PD-1 ligand and a PD-1 polypeptide can be administered up to about 1 day, up to about 2 days, up to about 3 days, up to about 4 days, up to about 5 days, up to about 6 days, up to about 7 days, up to about 2 weeks, up to about 3 weeks, up to about 4 weeks, up to about 5 weeks, up to about 6 weeks, up to about 7 weeks, up to about 8 weeks, up to about 12 weeks, up to about 16 weeks, up to about 20 weeks, up to about 24 weeks, up to about 28 weeks, up to about 32 weeks, up to about 36 weeks, up to about 40 weeks, up to about 44 weeks, up to about 48 weeks, up to about 52 weeks, up to about 2 years, up to about 3 years, up to about 4 years, up to about 5 years, or up to about 6 years after the administration of the one or more pneumococcal polysaccharide antigens.

Dosages of the therapeutic agents used in the presently disclosed subject matter must ultimately be set by an attending physician. Accordingly, the dosage range for administration will be adjusted by the physician as necessary. It will be appreciated that an amount of an agent required for achieving the desired biological response may be different from the amount of agent effective for another purpose. General outlines of the dosages are provided herein below.

Generally, a suitable dose of one or more pneumococcal polysaccharide antigens for administration to a human will be in the range of from about 0.1 µg to about 100 µg per pneumococcal polysaccharide antigen; more particularly from about 0.1 µg to about 10 µg per pneumococcal polysaccharide antigen; alternatively from about 1 µg to about 50 µg per pneumococcal polysaccharide antigen; or from about 1 ng to about 25 µg per pneumococcal polysaccharide antigen; or from about 1 µg to about 15 µg per pneumococcal polysaccharide antigen; or from about 1 µg to about 10 µg per pneumococcal polysaccharide antigen; or from about 1 µg to about 5 µg per pneumococcal polysaccharide antigen. For example, each dose can comprise 100, 150, 200, 250, 300, 400, 500, or 750 µg or 1, 1.5, 2, 3, 4, 5, 6, 7, 7.5, 8, 9, 10, 11, 12, 13, 14, 15, 16, 18, 20, 22, 25, 30, 40, 50, 60, 70, 80, 90, or 100 µg.

Generally, a suitable dose of an agent that inhibits the interaction between a PD-1 ligand and a PD-1 polypeptide, or a pharmaceutically acceptable salt thereof, for administration to a human will be in the range of about 0.1 mg/kg to about 500 mg/kg; alternatively, from about 1 mg to about 400 mg; preferably from about 1 mg to about 300 mg.

Actual dosage levels of the agents described herein can be varied so as to obtain an amount of the agent that is effective to achieve the desired therapeutic response for a particular subject, composition, route of administration, and disease, disorder, or condition without being toxic to the subject. The selected dosage level will depend on a variety of factors including the activity of the particular agent employed, or salt thereof, the route of administration, the time of administration, the rate of excretion of the particular agent being employed, the duration of the treatment, other drugs, agents and/or materials used in combination with the particular agent employed, the age, sex, weight, condition, general health and prior medical history of the patient being treated, and like factors well known in the medical arts.

II. Immunogenic Compositions

In some embodiments, the presently disclosed subject matter is also directed to an immunogenic composition comprising: a) one or more pneumococcal polysaccharide antigens; b) an effective amount of an agent that inhibits the interaction between a PD-1 ligand and a PD-1 polypeptide; and c) a pharmaceutically acceptable carrier. In some embodiments, the one or more pneumococcal polysaccharide antigens are capsular polysaccharides from one or more different serotypes of Streptococcus pneumoniae, particularly wherein the one or more different serotypes of Streptococcus pneumoniae are selected from the group consisting of serotypes 1, 2, 3, 4, 5, 6A, 6B, 7F, 8, 9N, 9V, 10A, 11A, 12F, 14, 15B, 17F, 18C, 19A, 19F, 20, 22F, 23F, and 33F. In some embodiments the PD-1 polypeptide comprises the amino acid sequence of SEQ ID NO:1 or a functional variant thereof, particularly wherein the functional variant comprises an amino acid sequence at least 90% identical to the amino acid sequence of SEQ ID NO:1. In other embodiments, the PD-1 ligand is PDL1 or PDL2. In further embodiments, the agent is an anti-PD-1 ligand antibody or a small molecule. In further embodiments, the one or more pneumococcal polysaccharide antigens are conjugated to a carrier protein. In a still further embodiment, the immunogenic composition further comprises an adjuvant.

A. Pneumococcal Polysaccharide Antigens

In some embodiments, the presently disclosed subject matter is directed to immunogenic compositions comprising one or more pneumococcal polysaccharide antigens. In some embodiments, the one or more pneumococcal polysaccharide antigens are included within a pneumococcal polysaccharide vaccine (i.e., a pneumococcal polysaccharide vaccine comprising one or more pneumococcal polysaccharide antigens).

A vaccine can contain a variety of different antigens. Examples of antigens include whole-killed or attenuated organisms, subfractions of these organisms/tissues, proteins, or, in their most simple form, peptides. Antigens can also be recognized by the immune system in form of glycosylated proteins or peptides and may also be or contain polysaccharides or lipids. Short peptides can also be used. For example, cytotoxic T-cells recognize antigens in the form of short, usually 8-11 amino acid long, peptides in conjunction with major histocompatibility complex (MHC). B-cells can recognize linear epitopes as short as 4-5 amino acids, as well as three-dimensional structures (conformational epitopes). In order to obtain sustained, antigen-specific immune responses, adjuvants need to trigger immune cascades that involve all cells of the immune system. Adjuvants act primarily, but not exclusively, on so-called antigen presenting cells (APCs). These cells usually first encounter the antigen(s), followed by presentation of processed or unmodified antigen to immune effector cells. Intermediate cell types may also be involved. Only effector cells with the appropriate specificity are activated in a productive immune response. An adjuvant may also locally retain antigens and co-injected other factors. In addition, an adjuvant may act as a chemoattractant for other immune cells or may act locally and/or systemically as a stimulating agent for the immune system.

Capsular polysaccharides from *Streptococcus pneumoniae* can be prepared by standard techniques known to those skilled in the art. For example, polysaccharides can be isolated from bacteria and may be sized to some degree by known methods (e.g., European Patent Nos. EP497524 and EP497525) and preferably by microfluidisation. Polysaccharides can be sized in order to reduce viscosity in polysaccharide samples and/or to improve filterability for conjugated products.

In some embodiments, pneumococcal polysaccharide serotypes may be grown in a soy-based medium. The individual polysaccharides are then purified through standard steps including centrifugation, precipitation, and ultra-filtration (e.g., U.S. Patent Application Publication No. 2008/0286838 and U.S. Pat. No. 5,847,112).

Carrier proteins are preferably proteins that are non-toxic and non-reactogenic and obtainable in sufficient amount and purity. A carrier protein can be conjugated or joined with a *Streptococcus pneumoniae* polysaccharide to enhance immunogenicity of the polysaccharide. Carrier proteins should be amenable to standard conjugation procedures. In a particular embodiment, $CRM_{197}$ is used as the carrier protein. In one embodiment, each capsular polysaccharide is conjugated to the same carrier protein (each capsular polysaccharide molecule being conjugated to a single carrier protein). In another embodiment, the capsular polysaccharides are conjugated to two or more carrier proteins (each capsular polysaccharide molecule being conjugated to a single carrier protein). In such an embodiment, each capsular polysaccharide of the same serotype is typically conjugated to the same carrier protein.

$CRM_{197}$ is a non-toxic variant (i.e., toxoid) of diphtheria toxin. In one embodiment, it is isolated from cultures of *Corynebacterium diphtheria* strain C7 (B197) grown in casamino acids and yeast extract-based medium. In another embodiment, $CRM_{197}$ is prepared recombinantly in accordance with the methods described in U.S. Pat. No. 5,614,382. Typically, $CRM_{197}$ is purified through a combination of ultra-filtration, ammonium sulfate precipitation, and ion-exchange chromatography. In some embodiments, $CRM_{197}$ is prepared in *Pseudomonas fluorescens* using Pfenex Expression Technology™ (Pfenex Inc., San Diego, Calif.).

Other suitable carrier proteins include additional inactivated bacterial toxins such as Diphtheria toxoid (DT), tetanus toxoid (TT) or fragment C of TT, pertussis toxoid, cholera toxoid (e.g., as described in PCT Patent App. Pub. No. WO 2004/083251), *E. coli* LT, *E. coli* ST, and exotoxin A from *Pseudomonas aeruginosa*. Bacterial outer membrane proteins such as outer membrane complex c (OMPC), porins, transferrin binding proteins, pneumococcal surface protein A (PspA; PCT Patent App. Publication No. WO 02/091998), pneumococcal adhesin protein (PsaA), C5a peptidase from Group A or Group B *streptococcus*, or *Haemophilus influenzae* protein D, pneumococcal pneumolysin (Kuo et al. (1995) *Infect. Immun.* 63:2706-2713) including ply detoxified in some fashion, such as dPLY-GMBS (e.g., PCT Patent App. Pub. No. WO 04/081515) or dPLY-formol, PhtX, including PhtA, PhtB, PhtD, PhtE and fusions of Pht proteins for example PhtDE fusions, PhtBE fusions (e.g., PCT Patent App. Pub. Nos. WO 01/98334 and WO 03/54007), can also be used. Other proteins, such as ovalbumin, keyhole limpet hemocyanin (KLH), bovine serum albumin (BSA) or purified protein derivative of tuberculin (PPD), PorB (from *N. meningitidis*), PD (*Haemophilus influenzae* protein D; e.g., European Patent No. EP 0 594 610 B), or immunologically functional equivalents thereof, synthetic peptides (e.g. European Patent Nos. EP0378881 and EP0427347), heat shock proteins (e.g. PCT Patent App. Pub. Nos. WO 93/17712 and WO 94/03208), pertussis proteins (e.g., PCT Patent App. Pub. No. WO 98/58668 and European Patent No. EPO471177), cytokines, lymphokines, growth factors or hormones (e.g., PCT Patent App. Pub. No. WO 91/01146), artificial proteins comprising multiple human $CD4^+$ T cell epitopes from various pathogen derived antigens (Falugi et al. (2001) *Eur. J. Immunol.* 31:3816-3824) such as N19 protein (Baraldoi et al. (2004) *Infect. Immun.* 72:4884-7), iron uptake proteins (e.g., PCT Patent App. Pub. No. WO 01/72337), toxin A or B of *C. difficile* (e.g., PCT Patent App. Pub. No. WO 00/61761), and flagellin (Ben-Yedidia et al. (1998) *Immunol. Lett.* 64:9) can also be used as carrier proteins.

Other DT mutants can be used, such as CRM176, CRM228, CRM 45 (Uchida et al. (1973) *J. Biol. Chem.* 218:3838-3844); CRM 9, CRM 45, CRM102, CRM 103 and CRM107 and other mutations; deletion or mutation of Glu-148 to Asp, Gln or Ser and/or Ala 158 to Gly and other mutations (U.S. Pat. No. 4,709,017 or U.S. Pat. No. 4,950,740); mutation of at least one or more residues Lys 516, Lys 526, Phe 530 and/or Lys 534 and other mutations (U.S. Pat. No. 5,917,017 or U.S. Pat. No. 6,455,673; or fragments disclosed in U.S. Pat. No. 5,843,711).

Purified polysaccharides are chemically activated to make the saccharides capable of reacting with a carrier protein. Once activated, each capsular polysaccharide may be separately conjugated to a carrier protein to form a glycoconjugate. The polysaccharide conjugates may be prepared by known coupling techniques.

Chemical activation of polysaccharides and subsequent conjugation to a carrier protein may be achieved by means described in U.S. Pat. Nos. 4,365,170, 4,673,574 and 4,902,506. Briefly, the chemistry described therein entails the activation of pneumococcal polysaccharides by reaction with any oxidizing agent which oxidizes a terminal hydroxyl group to an aldehyde, such as periodate (including sodium periodate, potassium periodate, or periodic acid). The reaction leads to a random oxidative cleavage of vicinal hydroxyl groups of the carbohydrates with the formation of reactive aldehyde groups.

Coupling to a protein carrier (e.g., $CRM_{197}$) can be by reductive amination via direct amination to the lysyl groups of the protein. For example, conjugation is carried out by reacting a mixture of the activated polysaccharide and carrier protein with a reducing agent such as sodium cyanoborohydride. Unreacted aldehydes are then capped with the addition of a strong reducing agent, such as sodium borohydride.

The conjugation method may also rely on activation of the saccharide with 1-cyano-4-dimethylamino pyridinium tetrafluoroborate (CDAP) to form a cyanate ester. The activated saccharide may thus be coupled directly or via a spacer (linker) group to an amino group on the carrier protein. For example, the spacer could be cystamine or cysteamine to give a thiolated polysaccharide which could be coupled to the carrier via a thioether linkage obtained after reaction with a maleimide-activated carrier protein (for example using GMBS) or a haloacetylated carrier protein (e.g. using iodoacetimide such as ethyl iodoacetimide HCl, or N-succinimidyl bromoacetate or SLAB, or SIA, or SBAP). Preferably, the cyanate ester (optionally made by CDAP chemistry) may be coupled with hexane diamine or adipic acid dihydrazide (ADH) and the amino-derivatised saccharide is conjugated to the carrier protein using carbodiimide (e.g. EDAC or EDC) chemistry via a carboxyl group on the protein carrier. Such conjugates are described in PCT Patent App. Pub. Nos. WO 93/15760, WO 95/08348, and WO 96/29094; and Chu et al. (1983) *Infect. Immunity* 40:245-256).

Other suitable techniques use carbodiimides, hydrazides, active esters, norbornane, p-nitrobenzoic acid, N-hydroxysuccinimide, S-NHS, EDC, and TSTU. Many are described in PCT Patent App. Pub. No. WO 98/42721. Conjugation may involve a carbonyl linker which may be formed by reaction of a free hydroxyl group of the saccharide with CDI (Bethell et al. (1979) *J. Biol. Chem.* 254:2572-4; Hearn et al. (1981) *J. Chromatogr.* 218:509-18) followed by reaction to form a carbamate linkage. This may involve reduction of the anomeric terminus to a primary hydroxyl group, optional protection/deprotection of the primary hydroxyl group, reaction of the primary hydroxyl group with CDI to form a CDI carbamate intermediate and coupling the CDI carbamate intermediate with an amino group on a protein.

Prior to formulation, each pneumococcal capsular polysaccharide antigen may be individually purified from *Streptococcus pneumoniae*, activated to form reactive aldehydes, and then covalently conjugated using reductive amination to the carrier protein $CRM_{197}$.

After conjugation of the capsular polysaccharide to the carrier protein, polysaccharide-protein conjugates are purified (enriched with respect to the amount of polysaccharide-protein conjugate) by one or more of a variety of techniques. Examples of these techniques are well known to the skilled artisan and include concentration/diafiltration operations, ultrafiltration, precipitation/elution, column chromatography, and depth filtration (e.g., U.S. Pat. No. 6,146,902).

As defined herein, an "adjuvant" is a substance that serves to enhance the immunogenicity of an immunogenic composition of the presently disclosed subject matter. An immune adjuvant may enhance an immune response to an antigen that is weakly immunogenic when administered alone, e.g., inducing no or weak antibody titers or cell-mediated immune response, increase antibody titers to the antigen, and/or lowers the dose of the antigen effective to achieve an immune response in the individual. Thus, adjuvants are often given to boost the immune response and are well known to the skilled artisan. Suitable adjuvants to enhance effectiveness of the composition include, but are not limited to: (1) aluminum salts (alum), such as aluminum hydroxide, aluminum phosphate, aluminum sulfate, etc.; (2) oil-in-water emulsion formulations (with or without other specific immunostimulating agents such as muramyl peptides (defined below) or bacterial cell wall components), such as, for example, (a) MF59 (PCT Patent App. Pub. No. WO 90/14837), containing 5% Squalene, 0.5% TWEEN 80, and 0.5% SPAN 85 (optionally containing various amounts of MTP-PE) formulated into submicron particles using a microfluidizer such as Model 110Y microfluidizer (Microfluidics, Newton, Mass.), (b) SAF, containing 10% Squalene, 0.4% TWEEN 80, 5% pluronic-blocked polymer L121, and thr-MDP either microfluidized into a submicron emulsion or vortexed to generate a larger particle size emulsion, (c) Ribi™ adjuvant system (RAS), (Corixa, Hamilton, Mont.) containing 2% Squalene, 0.2% TWEEN 80, and one or more bacterial cell wall components from the group consisting of 3-O-deaylated monophosphorylipid A (MPL™) described in U.S. Pat. No. 4,912,094, trehalose dimycolate (TDM), and cell wall skeleton (CWS), preferably MPL+CWS (Detox™); and (d) a Montanide ISA; (3) saponin adjuvants, such as Quil A or STIMULON™ QS-21 (Antigenics, Framingham, Mass.) (e.g., U.S. Pat. No. 5,057,540) may be used or particles generated therefrom such as ISCOM (immunostimulating complexes formed by the combination of cholesterol, saponin, phospholipid, and amphipathic proteins) and Iscomatrix® (having essentially the same structure as an ISCOM but without the protein); (4) bacterial lipopolysaccharides, synthetic lipid A analogs such as aminoalkyl glucosamine phosphate compounds (AGP), or derivatives or analogs thereof, which are available from Corixa, and which are described in U.S. Pat. No. 6,113,918; one such AGP is 2-[(R)-3-tetradecanoyloxytetradecanoylamino]ethyl 2-Deoxy-4-O-phosphono-3-O—[(R)-3-tetradecanoyloxytetradecanoyl]-2-[(R)-3-tetradecanoyloxytetradecanoylamino]-β-D-glucopyranoside, which is also known as 529 (formerly known as RC529), which is formulated as an aqueous form or as a stable emulsion; (5) synthetic polynucleotides such as oligonucleotides containing CpG motif(s) (U.S. Pat. No. 6,207,646); and (6) cytokines, such as interleukins (e.g., IL-1, IL-2, IL-4, IL-5, IL-6, IL-7, IL-12, IL-15, IL-18, etc.), interferons (e.g., gamma interferon), granulocyte macrophage colony stimulating factor (GM-CSF), macrophage colony stimulating factor (M-CSF), tumor necrosis factor (TNF), costimulatory molecules B7-1 and B7-2, etc; and (7) complement, such as a trimer of complement component C3d.

In another embodiment, the adjuvant is a mixture of 2, 3, or more of the above adjuvants, e.g., SBAS2 (an oil-in-water emulsion also containing 3-deacylated monophosphoryl lipid A and QS21). Muramyl peptides include, but are not limited to, N-acetyl-muramyl-L-threonyl-D-isoglutamine (thr-MDP), N-acetyl-normuramyl-L-alanine-2-(1'-2' dipalmitoyl-sn-glycero-3-hydroxyphosphoryloxy)-ethylamine (MTP-PE), and the like.

In certain embodiments, the adjuvant is an aluminum salt. The aluminum salt adjuvant may be an alum-precipitated vaccine or an alum-adsorbed vaccine. Aluminum-salt adjuvants are well known in the art and are described, for example, in Harlow and Lane (1988) Antibodies: A Laboratory Manual Cold Spring Harbor Laboratory; and Nicklas (1992) *Research in Immunology* 143:489-493). The aluminum salt includes, but is not limited to, hydrated alumina, alumina hydrate, alumina trihydrate (ATH), aluminum hydrate, aluminum trihydrate, ALHYDROGEL, SUPERFOS, Amphogel, aluminum (III) hydroxide, aluminum hydroxyphosphate sulfate (Aluminum Phosphate Adjuvant (APA)), amorphous alumina, trihydrated alumina, or trihydroxyaluminum.

APA is an aqueous suspension of aluminum hydroxyphosphate. APA is manufactured by blending aluminum chloride and sodium phosphate in a 1:1 volumetric ratio to precipitate aluminum hydroxyphosphate. After the blending process, the material is size-reduced with a high-shear mixer to achieve a target aggregate particle size in the range of 2-8 μm. The product is then diafiltered against physiological saline and steam sterilized.

In certain embodiments, a commercially available $Al(OH)_3$ (e.g. ALHYDROGELAL or SUPERFOS of Denmark/Accurate Chemical and Scientific Co., Westbury, N.Y.) is used to adsorb proteins in a ratio of 50-200 g protein/mg aluminum hydroxide. Adsorption of protein is dependent, in another embodiment, on the pI (Isoelectric pH) of the protein and the pH of the medium. A protein with a lower pI adsorbs to the positively charged aluminum ion more strongly than a protein with a higher pI. Aluminum salts may establish a depot of Ag that is released slowly over a period of 2-3 weeks, be involved in nonspecific activation of macrophages and complement activation, and/or stimulate innate immune mechanism (possibly through stimulation of uric acid; e.g., Lambrecht et al. (2009) *Curr. Opin. Immunol.* 21:23).

In certain embodiments, the adjuvant is a CpG-containing nucleotide sequence, for example, a CpG-containing oligonucleotide, in particular, a CpG-containing oligodeoxynucleotide (CpG ODN). In another embodiment, the adjuvant is ODN 1826, which may be acquired from Coley Pharmaceutical Group.

"CpG-containing nucleotide," "CpG-containing oligonucleotide," "CpG oligonucleotide," and similar terms refer to a nucleotide molecule of 6-50 nucleotides in length that contains an unmethylated CpG moiety (e.g., Wang et al. (2003) *Vaccine* 21:4297). CpG-containing oligonucleotides include modified oligonucleotides using any synthetic internucleoside linkages, modified base and/or modified sugar. Methods for use of CpG oligonucleotides are well known in the art and are described, e.g., in Sur et al. (1999) *J. Immunol.* 162:6284-93; Verthelyi (2006) *Methods Mol. Med.* 127:139-58; and Yasuda et al. (2006) *Crit. Rev. Ther. Drug Carrier Syst.* 23:89-110).

Administration of vaccine compositions of the presently disclosed subject matter can include one or more of: injection via intramuscular, intraperitoneal, intradermal or subcutaneous routes; or via mucosal administration to the oral/alimentary, respiratory or genitourinary tracts. In one embodiment, intranasal administration is used for the treatment of pneumonia or otitis media (as nasopharyngeal carriage of pneumococci can be more effectively prevented, thus attenuating infection at its earliest stage).

Optimal amounts of components for a particular vaccine can be ascertained by standard studies involving observation of appropriate immune responses in subjects. For example, in another embodiment, the dosage for human vaccination is determined by extrapolation from animal studies to human data. In another embodiment, the dosage is determined empirically.

In one embodiment, the dose of the aluminum salt is 10, 15, 20, 25, 30, 50, 70, 100, 125, 150, 200, 300, 500, or 700 μg, or 1, 1.2, 1.5, 2, 3, 5 mg or more. In yet another embodiment, the dose of alum salt described above is per μg of recombinant protein.

In one embodiment, a vaccine composition of the present presently disclosed subject matter is administered as a single inoculation. In another embodiment, the vaccine is administered twice, three times or four times or more, adequately spaced apart. For example, the composition may be administered at 1, 2, 3, 4, 5, or 6 month intervals or any combination thereof. The immunization schedule can follow that designated for pneumococcal vaccines. For example, the routine schedule for infants and toddlers against invasive disease caused by *Streptococcus pneumoniae* is 2, 4, 6 and 12-15 months of age. Thus, in a preferred embodiment, the composition is administered as a 4-dose series at 2, 4, 6, and 12-15 months of age.

Vaccine compositions may also include one or more proteins from *Streptococcus pneumoniae*. Examples of *Streptococcus pneumoniae* proteins suitable for inclusion include those identified in PCT Patent App. Pub. Nos. WO 02/083855 and WO 02/053761.

Vaccine compositions can be administered to a subject by one or more methods known to a person skilled in the art, such as parenterally, transmucosally, transdermally, intramuscularly, intravenously, intra-dermally, intra-nasally, subcutaneously, intra-peritoneally, and formulated accordingly.

In one embodiment, vaccine compositions are administered via epidermal injection, intramuscular injection, intravenous, intra-arterial, subcutaneous injection, or intra-respiratory mucosal injection of a liquid preparation. Liquid formulations for injection include solutions and the like.

Vaccine compositions can be formulated as single dose vials, multi-dose vials or as pre-filled syringes.

In another embodiment, vaccine compositions can be administered orally, and may thus be formulated in a form suitable for oral administration, i.e., as a solid or a liquid preparation. Solid oral formulations include tablets, capsules, pills, granules, pellets and the like. Liquid oral formulations include solutions, suspensions, dispersions, emulsions, oils and the like.

Pharmaceutically acceptable carriers for liquid formulations are aqueous or non-aqueous solutions, suspensions, emulsions or oils. Examples of nonaqueous solvents are propylene glycol, polyethylene glycol, and injectable organic esters such as ethyl oleate. Aqueous carriers include water, alcoholic/aqueous solutions, emulsions or suspensions, including saline and buffered media. Examples of oils are those of animal, vegetable, or synthetic origin, for example, peanut oil, soybean oil, olive oil, sunflower oil, fish-liver oil, another marine oil, or a lipid from milk or eggs.

Vaccine compositions may be isotonic, hypotonic or hypertonic. However it is often preferred that a vaccine composition for infusion or injection is essentially isotonic when it is administered. Hence, for storage the vaccine composition may preferably be isotonic or hypertonic. If the vaccine composition is hypertonic for storage, it may be diluted to become an isotonic solution prior to administration.

The isotonic agent may be an ionic isotonic agent such as a salt or a non-ionic isotonic agent such as a carbohydrate. Examples of ionic isotonic agents include but are not limited to NaCl, $CaCl_2$, KCl and $MgCl_2$. Examples of non-ionic isotonic agents include but are not limited to mannitol, sorbitol and glycerol.

It is also preferred that at least one pharmaceutically acceptable additive is a buffer. For some purposes, for example, when the vaccine composition is meant for infusion or injection, it is often desirable that the composition comprises a buffer, which is capable of buffering a solution to a pH in the range of 4 to 10, such as 5 to 9, for example 6 to 8.

The buffer may for example be selected from the group consisting of TRIS, acetate, glutamate, lactate, maleate, tartrate, phosphate, citrate, carbonate, glycinate, histidine, glycine, succinate and triethanolamine buffer. The buffer may furthermore for example be selected from USP compatible buffers for parenteral use, in particular, when the pharmaceutical formulation is for parenteral use. For example the buffer may be selected from the group consisting of monobasic acids such as acetic, benzoic, gluconic, glyceric and lactic; dibasic acids such as aconitic, adipic, ascorbic, carbonic, glutamic, malic, succinic and tartaric; polybasic acids such as citric and phosphoric; and bases such as ammonia, diethanolamine, glycine, triethanolamine, and TRIS.

Parenteral vehicles (for subcutaneous, intravenous, intraarterial, or intramuscular injection) include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Examples are sterile liquids such as water and oils, with or without the addition of a surfactant and other pharmaceutically acceptable adjuvants. In general, water, saline, aqueous dextrose and related sugar solutions, glycols such as propylene glycols or polyethylene glycol, and Polysorbate-80 are preferred liquid carriers, particularly for injectable solutions. Examples of oils are those of animal, vegetable, or synthetic origin, for example, peanut oil, soybean oil, olive oil, sunflower oil, fish-liver oil, another marine oil, or a lipid from milk or eggs.

The formulations of the presently disclosed subject matter may also contain a surfactant. Preferred surfactants include, but are not limited to: the polyoxyethylene sorbitan esters surfactants (commonly referred to as the TWEENS), especially polysorbate 20 and polysorbate 80; copolymers of ethylene oxide (EO), propylene oxide (PO), and/or butylene oxide (BO), sold under the DOWFAX™ tradename, such as linear EO/PO block copolymers; octoxynols, which can vary in the number of repeating ethoxy (oxy-1,2-ethanediyl) groups, with octoxynol-9 (TRITON X-100, or t-octylphenoxypolyethoxyethanol) being of particular interest; (octylphenoxy)polyethoxyethanol (IGEPAL CA-630/NP-40); phospholipids such as phosphatidylcholine (lecithin); nonylphenol ethoxylates, such as the Tergitol™ NP series; polyoxyethylene fatty ethers derived from lauryl, cetyl, stearyl and oleyl alcohols (known as Brij surfactants), such as triethyleneglycol monolauryl ether (BRIJ 30); and sorbitan esters (commonly known as the SPANs), such as sorbitan trioleate (SPAN 85) and sorbitan monolaurate. A preferred surfactant for including in the emulsion is TWEEN 80 (polyoxyethylene sorbitan monooleate).

Mixtures of surfactants can be used, e.g. TWEEN 80/SPAN 85 mixtures. A combination of a polyoxyethylene sorbitan ester such as polyoxyethylene sorbitan monooleate (TWEEN 80) and an octoxynol such as t-octylphenoxypolyethoxyethanol (TRITON X-100) is also suitable. Another useful combination comprises laureth 9 plus a polyoxyethylene sorbitan ester and/or an octoxynol.

Preferred amounts of surfactants (% by weight) are: polyoxyethylene sorbitan esters (such as TWEEN 80) 0.01 to 1%, in particular about 0.1%; octyl- or nonylphenoxy polyoxyethanols (such as TRITON X-100, or other detergents in the TRITON series) 0.001 to 0.1%, in particular 0.005 to 0.02%; polyoxyethylene ethers (such as laureth 9) 0.1 to 20%, preferably 0.1 to 10% and in particular 0.1 to 1% or about 0.5%.

In another embodiment, the vaccine composition is delivered in a controlled release system. For example, the vaccine composition can be administered using intravenous infusion, a transdermal patch, liposomes, or other modes of administration. In another embodiment, polymeric materials are used; e.g. in microspheres in or an implant.

B. Agents that Inhibit the Interaction Between a PD-1 Ligand and a PD-1 Polypeptide In some embodiments, the presently disclosed subject matter is also directed to an immunogenic composition comprising an effective amount of an agent that inhibits the interaction between a PD-1 ligand and a PD-1 polypeptide.

i. PD-1 Polypeptides and PD-1 Ligands

Programmed cell death protein 1, also known as PD-1, is a 288 amino acid cell surface protein molecule (SEQ ID NO:1; NCBI Reference Sequence: NP_005009.2) that in humans is encoded by the PDCD1 gene (Entrez Gene GeneID: 5133; see also Ishida et al. (1992) *EMBO J.* 11:3887; Shinohara et al. (1994) *Genomics* 23:704; U.S. Pat. No. 5,698,520). PD-1 is a member of the immunoglobulin gene superfamily, has an extracellular region containing immunoglobulin superfamily domain, a transmembrane domain, and an intracellular region including an immunoreceptor tyrosine-based inhibitory motif (ITIM; Ishida et al. (1992) *EMBO J.* 11:3887; Shinohara et al. (1994) *Genomics* 23:704). These features also define a larger family of polypeptides, called the immunoinhibitory receptors, which also includes gp49B, PIR-B, and the killer inhibitory receptors (KIRs) (Vivier and Daeron (1997) *Immunol. Today* 18:286). It is often assumed that the tyrosyl phosphorylated ITIM motif of these receptors interacts with SH2-domain containing phosphatases, which leads to inhibitory signals. A subset of these immunoinhibitory receptors bind to MHC polypeptides, for example the KIRs, and CTLA4 bind to B7-1 and B7-2. It has been proposed that there is a phylogenetic relationship between the MHC and B7 genes (Henry et al. (1999) *Immunol. Today* 20(6):285-8). Like CTLA4, PD-1 is rapidly induced on the surface of T-cells in response to anti-CD3 (Agata et al. (1996) *Int. Immunol.* 8:765). In contrast to CTLA4, however, PD-1 is also induced on the surface of B-cells (in response to anti-IgM). PD-1 is also expressed on a subset of thymocytes and myeloid cells (Agata et al. (1996) *Int. Immunol.* 8:765; Nishimura et al. (1996) *Int. Immunol.* 8:773).

Two types of human PD-1 ligands have been identified: PDL1 and PDL2. PD-1 ligands comprise a signal sequence, and an IgV domain, an IgC domain, a transmembrane domain, and a short cytoplasmic tail. Both PDL1 (SEQ ID NO:2; NCBI Reference Sequence: NP_001254635.1; Freeman et al. (2000) *J. Exp. Med.* 192:1027) and PDL2 (SEQ ID NO:3; NCBI Reference Sequence: NP_079515.2; Latchman et al. (2001) *Nat. Immunol.* 2:261) are members of the B7 family of polypeptides. Both PDL1 and PDL2 are expressed in placenta, spleen, lymph nodes, thymus, and heart. Only PDL2 is expressed in pancreas, lung and liver while only PDL1 is expressed in fetal liver. Both PD-1 ligands are upregulated on activated monocytes and dendritic cells. The fact that PD-1 binds to PDL1 and PDL2 places PD-1 in a family of inhibitory receptors with CTLA4.

Accordingly, in some embodiments of the presently disclosed subject matter, "a PD-1 polypeptide" comprises both the wild-type PD-1 corresponding to the amino acid sequence of SEQ ID NO:1 or a functional variant thereof "A PD-1 ligand" includes both "PDL1 polypeptides" and "PDL2 polypeptides." "A PDL1 polypeptide" comprises both the wild-type PDL1 corresponding to the amino acid sequence of SEQ ID NO:2 or a functional variant thereof "A PDL2 polypeptide" comprises both the wild-type PDL2 corresponding to the amino acid sequence of SEQ ID NO:3 or a functional variant thereof.

"Functional variants" of a PD-1 polypeptide, a PDL1 polypeptide, and/or a PDL2 polypeptide include functional fragments, functional mutant proteins, and/or functional fusion proteins. A functional variant of a selected polypeptide refers to an isolated and/or recombinant protein or polypeptide which has at least one property, activity and/or functional characteristic of the selected polypeptide (e.g., a PD-1 polypeptide, a PDL1 polypeptide, and/or a PDL2 polypeptide). As used herein, the term "activity," when used with respect to a polypeptide, e.g., a PD-1 polypeptide or a PD-1 ligand (i.e., PDL1 polypeptide or PDL2 polypeptide) includes activities which are inherent in the structure of the wild-type protein.

For example, with respect to PD-1, the term "activity" includes the ability of a PD-1 polypeptide to modulate an inhibitory signal in an activated immune cell, e.g., by engaging a natural PD-1 ligand on an antigen presenting cell. PD-1 transmits an inhibitory signal to an immune cell in a manner similar to CTLA4. Modulation of an inhibitory signal in an immune cell results in modulation of proliferation of, and/or cytokine secretion by, an immune cell. Thus, the term "PD-1 activity" includes the ability of a PD-1 polypeptide to bind its natural ligand(s), the ability to modulate immune cell costimulatory or inhibitory signals, and the ability to modulate the immune response.

Similarly, with respect to PD-1 ligands (e.g., PDL1 polypeptides or functional variants thereof and PDL2 polypeptides or functional variants thereof), the term "activity" includes the ability to modulate immune cell costimulation (e.g. by modulating a costimulatory signal in an activated immune cell) or to modulate inhibition by modulating an inhibitory signal in an immune cell (e.g., by engaging a natural receptor on an immune cell). Those of skill in the art will recognize that when an activating form of the PD-1 ligand binds to a costimulatory receptor, a costimulatory signal is generated in the immune cell. When an activating form of the PD-1 ligand binds to an inhibitory receptor, an inhibitory signal is generated in the immune cell. Modulation of a costimulatory signal results in modulation of effector function of an immune cell. Thus, the term "PD-1 ligand activity" includes the ability of a PD-1 ligand to bind its natural receptor(s) (e.g. PD-1), the ability to modulate immune cell costimulatory or inhibitory signals, and the ability to modulate the immune response.

As used herein, the term "costimulate," as used with reference to activated immune cells, includes the ability of a costimulatory polypeptide to provide a second, non-activating receptor mediated signal (a "costimulatory signal") that induces proliferation or effector function. For example, a costimulatory signal can result in cytokine secretion, e.g., in a T cell that has received a T cell-receptor-mediated signal. Immune cells that have received a cell-receptor mediated signal, e.g., via an activating receptor are referred to herein as "activated immune cells." As used herein, the term "costimulatory receptor" includes receptors which transmit a costimulatory signal to a immune cell. As used herein, the term "inhibitory receptors" includes receptors which transmit a negative signal to an immune cell (e.g., PD-1). An inhibitory signal as transduced by an inhibitory receptor can occur even if a costimulatory receptor (such as CD28) is not present on the immune cell and, thus, is not simply a function of competition between inhibitory receptors and costimulatory receptors for binding of costimulatory polypeptides (Fallarino et al. (1998) *J. Exp. Med.* 188:205). Transmission of an inhibitory signal to an immune cell can result in unresponsiveness or anergy or programmed cell death in the immune cell. Preferably transmission of an inhibitory signal operates through a mechanism that does not involve apoptosis. As used herein the term "apoptosis" includes programmed cell death which can be characterized using techniques which are known in the art. Apoptotic cell death can be characterized, e.g., by cell shrinkage, membrane blebbing and chromatin condensation culminating in cell fragmentation. Cells undergoing apoptosis also display a characteristic pattern of internucleosomal DNA cleavage.

Generally, fragments or portions of PD-1, PDL1, and/or PDL2 encompassed by the presently disclosed subject matter include those having a deletion (i.e. one or more deletions) of an amino acid (i.e., one or more amino acids) relative to the wild-type PD-1, PDL1, and/or PDL2 (such as N-terminal, C-terminal or internal deletions). Fragments or portions in which only contiguous amino acids have been deleted or in which non-contiguous amino acids have been deleted relative to wild-type PD-1, PDL1, and/or PDL2 are also envisioned. Generally, mutants or derivatives of PD-1, PDL1, and/or PDL2 encompassed by the present presently disclosed subject matter include natural or artificial variants differing by the addition, deletion and/or substitution of one or more contiguous or non-contiguous amino acid residues, or modified polypeptides in which one or more residues is modified, and mutants comprising one or more modified residues. Preferred mutants are natural or artificial variants of PD-1, PDL1, and/or PDL2 differing by the addition, deletion and/or substitution of one or more contiguous or non-contiguous amino acid residues.

Generally, a PD-1 polypeptide or functional variant thereof has an amino acid sequence which is at least about 80% identical, at least about 81% identical, at least about 82% identical, at least about 83% identical, at least about 84% identical, at least about 85% identical, at least about 86% identical, at least about 87% identical, at least about 88% identical, at least about 89% identical, at least about 90% identical, at least about 91% identical, at least about 92% identical, at least about 93% identical, at least about 94% identical, at least about 95% identical, at least about 96% identical, at least about 97% identical, at least about 98% identical, or at least about 99% identical to SEQ ID NO:1 over the length of the variant.

Generally, a PDL1 polypeptide or functional variant thereof has an amino acid sequence which is at least about 80% identical, at least about 81% identical, at least about 82% identical, at least about 83% identical, at least about 84% identical, at least about 85% identical, at least about 86% identical, at least about 87% identical, at least about 88% identical, at least about 89% identical, at least about 90% identical, at least about 91% identical, at least about 92% identical, at least about 93% identical, at least about 94% identical, at least about 95% identical, at least about 96% identical, at least about 97% identical, at least about 98% identical, or at least about 99% identical to SEQ ID NO:2 over the length of the variant.

Generally, a PDL2 polypeptide or functional variant thereof has an amino acid sequence which is at least about 80% identical, at least about 81% identical, at least about 82% identical, at least about 83% identical, at least about 84% identical, at least about 85% identical, at least about 86% identical, at least about 87% identical, at least about 88% identical, at least about 89% identical, at least about 90% identical, at least about 91% identical, at least about 92% identical, at least about 93% identical, at least about 94% identical, at least about 95% identical, at least about 96% identical, at least about 97% identical, at least about 98% identical, or at least about 99% identical to SEQ ID NO:3 over the length of the variant.

In some embodiments, the amino acid sequences of SEQ ID NO:1, SEQ ID NO:2, and SEQ ID NO:3 are used to make purified protein of a PD-1 polypeptide, a PDL1 polypeptide, and/or a PDL2 polypeptide, respectively, for example, using currently available recombinant protein production. Amino acid sequence identity can be determined using a suitable amino acid sequence alignment algorithm. PD-1 polypeptides, PDL1 polypeptides, and/or PDL2 polypeptides and functional variants thereof can be produced using well-known methods, such as recombinant expression and purification, chemical synthesis (e.g., synthetic peptides), or by combinations of biological and chemical methods, and recombinant proteins or polypeptides which are isolated. The proteins can be obtained in an isolated state of at least about 50% by weight, preferably at least about 75% by weight, and more preferably, in essentially pure form. Proteins or polypeptides referred to herein as "recombinant" are proteins or polypeptides produced by the expression of recombinant nucleic acids.

"Sequence identity" or "identity" in the context of proteins or polypeptides refers to the amino acid residues in two amino acid sequences that are the same when aligned for maximum correspondence over a specified comparison window.

Thus, "percentage of sequence identity" refers to the value determined by comparing two optimally aligned sequences over a comparison window, wherein the portion of the amino acid sequence in the comparison window may comprise additions or deletions (i.e., gaps) as compared to the reference sequence (which does not comprise additions or deletions) for optimal alignment of the two sequences. The percentage is calculated by determining the number of positions at which the identical amino acid residue occurs in both sequences to yield the number of matched positions, dividing the number of matched positions by the total number of positions in the window of comparison and multiplying the results by 100 to yield the percentage of sequence identity. Useful examples of percent sequence identities include, but are not limited to, 50%, 55%, 60%, 65%, 70%, 75%, 80%, 85%, 90%, or 95%, or any integer percentage from 50% to 100%. These identities can be determined using any of the programs described herein.

Sequence alignments and percent identity or similarity calculations may be determined using a variety of comparison methods designed to detect homologous sequences including, but not limited to, the MegAlign™ program of the LASERGENE bioinformatics computing suite (DNASTAR Inc., Madison, Wis.). Within the context of this application it will be understood that where sequence analysis software is used for analysis, that the results of the analysis will be based on the "default values" of the program referenced, unless otherwise specified. As used herein "default values" will mean any set of values or parameters that originally load with the software when first initialized. The "Clustal V method of alignment" corresponds to the alignment method labeled Clustal V (described by Higgins and Sharp (1989) *CABIOS* 5:151-153; Higgins et al. (1992) *Comput. Appl. Biosci.* 8:189-191) and found in the MegAlign™ program of the LASERGENE bioinformatics computing suite (DNASTAR Inc., Madison, Wis.).

It is well understood by one skilled in the art that many levels of sequence identity are useful in identifying proteins or polypeptides (e.g., from other species) wherein the proteins or polypeptides have the same or similar function or activity. Useful examples of percent identities include, but are not limited to, 50%, 55%, 60%, 65%, 70%, 75%, 80%, 85%, 90%, or 95%, or any integer percentage from 50% to 100%. Indeed, any integer amino acid identity from 50% to 100% may be useful in describing the present presently disclosed subject matter, such as 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%.

As described above, in some embodiments, the presently disclosed subject matter is directed to methods of use for and compositions comprising an effective amount of an agent that inhibits the interaction between a PD-1 ligand or a functional variant thereof and a PD-1 polypeptide or a functional variant thereof. As used herein, the term "interaction", when referring to an interaction between two molecules, refers to the physical contact (e.g., binding) of the molecules with one another. Generally, such an interaction results in an activity (which produces a biological effect) of one or both of said molecules. The activity may be a direct activity of one or both of the molecules, (e.g., signal transduction). Alternatively, one or both molecules in the interaction may be prevented from binding their ligand, and thus be held inactive with respect to ligand binding activity (e.g., binding its ligand and triggering or inhibiting costimulation). To inhibit such an interaction results in the disruption of the activity of one or more molecules involved in the interaction. To enhance such an interaction is to prolong or increase the likelihood of said physical contact, and prolong or increase the likelihood of said activity.

Accordingly, in some embodiments, the interaction between a PD-1 polypeptide and a PD-1 ligand prevents the PD-1 ligand from binding to a PD-1 polypeptide and, thus, inhibits delivery of an inhibitory immune signal. In one embodiment, agents which block the interaction between a PD-1 polypeptide and a PD-1 ligand can prevent inhibitory signaling. In one embodiment, agents that block the binding of a PD-1 polypeptide to a PD-1 ligand allow the PD-1 ligand to bind a PD-1 polypeptide, and provide an inhibitory signal to an immune cell, thus enhancing signaling inhibition.

ii. Antibodies

In one embodiment, the agent that inhibits the interaction between a PD-1 ligand and a PD-1 polypeptide is an anti-PD-1 ligand antibody (e.g., an anti-PDL1 polypeptide antibody and/or an anti-PDL2 polypeptide antibody).

The term "antibody," also known as an immunoglobulin (Ig), is a large Y-shaped protein produced by B cells that is used by the immune system to identify and neutralize foreign objects such as bacteria and viruses by recognizing a unique portion (epitope) of the foreign target, called an antigen. As used herein, the term "antibody" also includes an "antigen-binding portion" of an antibody (or simply "antibody portion"). The term "antigen-binding portion," as used herein, refers to one or more fragments of an antibody that retain the ability to specifically bind to an antigen (e.g., PD-1 ligand). It has been shown that the antigen-binding function of an antibody can be performed by fragments of a full-length antibody. Examples of binding fragments encompassed within the term "antigen-binding portion" of an antibody include: (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody; (v) a dAb fragment (Ward et al. (1989) *Nature* 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent polypeptides (known as single chain Fv (scFv); e.g., Bird et al. (1988) *Science* 242:423-426; Huston et al. (1988) *Proc. Natl. Acad Sci. USA* 85:5879-5883; and Osbourn et al. (1998) *Nature Biotechnology* 16:778). Such single chain antibodies are also intended to be encompassed within the term "antigen-binding portion" of an antibody. Any VH and VL sequences of specific scFv can be linked to human immunoglobulin constant region cDNA or genomic sequences, in order to generate expression vectors encoding complete IgG polypeptides or other isotypes. VH and VL can also be used in the generation of Fab, Fv or other fragments of immunoglobulins using either protein chemistry or recombinant DNA technology. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (e.g., Holliger et al. (1993) *Proc. Natl. Acad. Sci. USA* 90:6444-6448; Poljak et al. (1994) *Structure* 2:1121-1123).

Still further, an antibody or antigen-binding portion thereof may be part of larger immunoadhesion polypeptides, formed by covalent or noncovalent association of the antibody or antibody portion with one or more other proteins or peptides. Examples of such immunoadhesion polypeptides include use of the streptavidin core region to make a tetrameric scFv polypeptide (Kipriyanov et al. (1995) *Human Antibodies and Hybridomas* 6:93-101) and use of a cysteine residue, a marker peptide and a C-terminal polyhistidine tag to make bivalent and biotinylated scFv polypeptides (Kipriyanov et al. (1994) Mol. Immunol. 31:1047-1058). Antibody portions, such as Fab and F(ab')$_2$ fragments, can be prepared from whole antibodies using conventional techniques, such as papain or pepsin digestion, respectively, of whole antibodies. Moreover, antibodies, antibody portions and immunoadhesion polypeptides can be obtained using standard recombinant DNA techniques, as described herein.

Antibodies may be polyclonal or monoclonal; xenogeneic, allogeneic, or syngeneic; or modified forms thereof (e.g. humanized, chimeric, etc.). Antibodies may also be fully human. Preferably, antibodies of the presently disclosed subject matter bind specifically or substantially specifically to a PD-1 ligand or functional variant thereof. The terms "monoclonal antibodies" and "monoclonal antibody composition," as used herein, refer to a population of antibody polypeptides that contain only one species of an antigen binding site capable of immunoreacting with a particular epitope of an antigen, whereas the term "polyclonal antibodies" and "polyclonal antibody composition" refer to a population of antibody polypeptides that contain multiple species of antigen binding sites capable of interacting with a particular antigen. A monoclonal antibody composition typically displays a single binding affinity for a particular antigen with which it immunoreacts.

The term "humanized antibody", as used herein, is intended to include antibodies made by a non-human cell having variable and constant regions which have been altered to more closely resemble antibodies that would be made by a human cell. For example, by altering the non-human antibody amino acid sequence to incorporate amino acids found in human germline immunoglobulin sequences. The humanized antibodies of the presently disclosed subject matter may include amino acid residues not encoded by human germline immunoglobulin sequences (e.g., mutations introduced by random or site-specific mutagenesis in vitro or by somatic mutation in vivo), for example in the CDRs. The term "humanized antibody", as used herein, also includes antibodies in which CDR sequences derived from the germline of another mammalian species, such as a mouse, have been grafted onto human framework sequences.

An "isolated antibody", as used herein, is intended to refer to an antibody that is substantially free of other antibodies having different antigenic specificities (e.g., an isolated antibody that specifically binds a PD-1 ligand is substantially free of antibodies that specifically bind antigens other than a PD-1 ligand). Moreover, an isolated antibody may be substantially free of other cellular material and/or chemicals.

An isolated PD-1 ligand or functional variant thereof (or a nucleic acid encoding such polypeptides), can be used as an immunogen to generate antibodies that bind to the respective PD-1 ligand or functional variant thereof using standard techniques for polyclonal and monoclonal antibody preparation. A full-length PD-1 ligand can be used, or alternatively, the presently disclosed subject matter relates to antigenic peptide fragments of PD-1 ligands or functional variants thereof for use as immunogens. An antigenic peptide of a PD-1 ligand or a functional variant thereof comprises at least 8 amino acid residues and encompasses an epitope present in the respective full length molecule such that an antibody raised against the peptide forms a specific immune complex with the respective full length molecule. Preferably, the antigenic peptide comprises at least 10 amino acid residues, more preferably at least 15 amino acid residues, even more preferably at least 20 amino acid residues, and most preferably at least 30 amino acid residues. Preferred epitopes encompassed by the antigenic peptides are regions of a PD-1 ligand or a functional variant thereof that are located on the surface of the protein, e.g., hydrophilic regions. A standard hydrophobicity analysis of the polypeptide molecule can be performed to identify hydrophilic regions. Highly preferred epitopes encompassed by the antigenic peptides are the regions of the polypeptide molecule which are in the extracellular domain, and therefore are involved in binding. In one embodiment such epitopes can be specific for a given polypeptide molecule from one species, such as mouse or human (i.e., an antigenic peptide that spans a region of the polypeptide molecule that is not conserved across species is used as immunogen; such non conserved residues can be determined using an alignment such as that provided herein).

In a preferred embodiment, an antibody binds to a PD-1 ligand and blocks the interaction between the PD-1 ligand and a PD-1 polypeptide.

An immunogen comprising a PD-1 ligand or a functional variant thereof typically is used to prepare antibodies by immunizing a suitable subject, (e.g., rabbit, goat, mouse or other mammal) with the immunogen. An appropriate immunogenic preparation can contain, for example, a recombinantly expressed or chemically synthesized molecule or fragment thereof to which the immune response is to be generated. The preparation can further include an adjuvant, such as Freund's complete or incomplete adjuvant, or similar immunostimulatory agent Immunization of a suitable subject with an immunogenic preparation induces a polyclonal antibody response to the antigenic peptide contained therein.

Polyclonal antibodies can be prepared as described above by immunizing a suitable subject with a polypeptide immunogen. The polypeptide antibody titer in the immunized subject can be monitored over time by standard techniques, such as with an enzyme linked immunosorbent assay (ELISA) using immobilized polypeptide. If desired, the antibody directed against the antigen can be isolated from the mammal (e.g., from the blood) and further purified by well known techniques, such as protein A chromatography to obtain the IgG fraction. At an appropriate time after immunization, e.g., when the antibody titers are highest, antibody-producing cells can be obtained from the subject and used to prepare monoclonal antibodies by standard techniques, such as the hybridoma technique originally described by Kohler and Milstein (1975) *Nature* 256:495-497; Brown et al. (1981) *J. Immunol.* 127:539-46; Brown et al. (1980)*J. Biol. Chem.* 255:4980-83; Yeh et al. (1976) *Proc. Natl. Acad. Sci.* 76:2927-31; and Yeh et al. (1982) *Int. J. Cancer* 29:269-75), a human B cell hybridoma technique (Kozbor et al. (1983) *Immunol. Today* 4:72), the EBV-hybridoma technique (Cole et al. (1985) *Monoclonal Antibodies and Cancer Therapy*, Alan R. Liss, Inc., pp. 77-96) or trioma techniques. The technology for producing monoclonal antibody hybridomas is well known (see generally Kenneth, R. H. in *Monoclonal Antibodies: A New Dimension In Biological Analyses*, Plenum Publishing Corp., New York, N.Y. (1980); Lerner (1981) *Yale J. Biol. Med.* 54:387-402; Gefter et al. (1977) *Somatic Cell Genet.* 3:231-36). Briefly, an immortal cell line (typically a myeloma) is fused to lymphocytes (typically splenocytes) from a mammal immunized with an immunogen as described above, and the culture supernatants of the resulting hybridoma cells are screened to identify a hybridoma producing a monoclonal antibody that binds to the polypeptide antigen, preferably specifically.

Any of the many well known protocols used for fusing lymphocytes and immortalized cell lines can be applied for the purpose of generating an anti-PD-1 ligand monoclonal antibody (e.g., Galfre, G. et al. (1977) Nature 266:55052; Kenneth, R. H. in Monoclonal Antibodies: A New Dimension In Biological Analyses, Plenum Publishing Corp., New York, N.Y. (1980); Lerner (1981) Yale J. Biol. Med. 54:387-402; Gefter et al. (1977) Somatic Cell Genet. 3:231-36). Moreover, the ordinary skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present presently disclosed subject matter with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O—Ag14 myeloma lines. These myeloma lines are available from the American Type Culture Collection (ATCC), 10801 University Boulevard, Manassas, Va. 20110-2209 Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the presently disclosed subject matter are detected by screening the hybridoma culture supernatants for antibodies that bind a given polypeptide, e.g., using a standard ELISA assay.

As an alternative to preparing monoclonal antibody-secreting hybridomas, a monoclonal specific for one of the above described polypeptides antibody can be identified and isolated by screening a recombinant combinatorial immunoglobulin library (e.g., an antibody phage display library) with the appropriate polypeptide to thereby isolate immunoglobulin library members that bind the polypeptide. Kits for generating and screening phage display libraries are commercially available (e.g., the *Pharmacia Recombinant Phage Antibody System*, Catalog No. 27-9400-01; and the Stratagene SurfZAP™ Phage Display Kit, Catalog No. 240612). Additionally, examples of methods and reagents particularly amenable for use in generating and screening an antibody display library can be found in, for example, U.S. Pat. No. 5,223,409; PCT Patent App. Pub. No. WO 92/18619; PCT Patent App. Pub. No. WO 91/17271; PCT Patent App. Pub. No. 92/20791; PCT Patent App. Pub. No. WO 92/15679; PCT Patent App. Pub. No. WO 93/01288; PCT Patent App. Pub. No. WO 92/01047; PCT Patent App. Pub. No. WO 92/09690; PCT Patent App. Pub. No. WO 90/02809; Fuchs et al. (1991) *Biotechnology* (NY) 9:1369-1372; Hay et al. (1992) *Hum. Antibod. Hybridomas* 3:81-85; Huse et al. (1989) *Science* 246:1275-1281; Griffiths et al. (1993) *EMBO J.* 12:725-734; Hawkins et al. (1992) *J. Mol. Biol.* 226:889-896; Clarkson et al. (1991) *Nature* 352:624-628; Gram et al. (1992) *Proc. Natl. Acad. Sci. USA* 89:3576-3580; Garrard et al. (1991) *Biotechnology* (NY) 9:1373-1377; Hoogenboom et al. (1991) *Nucleic Acids Res.* 19:4133-4137; Barbas et al. (1991) *Proc. Natl. Acad. Sci. USA* 88:7978-7982; and McCafferty et al. (1990) *Nature* 348:552-554.

Additionally, recombinant anti-PD-1, anti-PD-1 ligand or anti-B7 polypeptide antibodies, such as chimeric and humanized monoclonal antibodies, comprising both human and non-human portions, which can be made using standard recombinant DNA techniques, are within the scope of the presently disclosed subject matter. Such chimeric and humanized monoclonal antibodies can be produced by recombinant DNA techniques known in the art, for example using methods described in PCT Patent App. Pub. No. PCT/US86/02269; European Patent App. No. 184,187; European Patent App. No. 171,496; European Patent App. No. 173,494; PCT Application WO 86/01533; U.S. Pat. No. 4,816,567; European Patent App. No. 125,023; Better et al. (1988) *Science* 240:1041-1043; Liu et al. (1987) *Proc. Natl. Acad. Sci. USA* 84:3439-3443; Liu et al. (1987)*J. Immunol.* 139:3521-3526; Sun et al. (1987) *Proc. Natl. Acad. Sci.* 84:214-218; Nishimura et al. (1987) *Cancer Res.* 47:999-1005; Wood et al. (1985) *Nature* 314:446-449; and Shaw et al. (1988) *J. Natl. Cancer Inst.* 80:1553-1559); Morrison, S. L. (1985) *Science* 229:1202-1207; Oi et ah (1986) *Biotechniques* 4:214; U.S. Pat. No. 5,225,539; Jones et al. (1986) *Nature* 321:552-525; Verhoeyan et al. (1988) *Science* 239:1534; and Beidler et al. (1988) *J. Immunol.* 141:4053-4060.

In addition, humanized antibodies can be made according to standard protocols such as those disclosed in U.S. Pat. No. 5,565,332. In another embodiment, antibody chains or specific binding pair members can be produced by recombination between vectors comprising nucleic acid molecules encoding a fusion of a polypeptide chain of a specific binding pair member and a component of a replicable generic display package and vectors containing nucleic acid molecules encoding a second polypeptide chain of a single binding pair member using techniques known in the art, e.g., as described in U.S. Pat. Nos. 5,565,332, 5,871,907, or 5,733,743. The use of intracellular antibodies to inhibit protein function in a cell is also known in the art (e.g., Carlson (1988) *Mol. Cell. Biol.* 8:2638-2646; Biocca et al. (1990) *EMBO J.* 9:101-108; Werge et al. (1990) *FEBS Lett.* 274:193-198; Carlson (1993) *Proc. Natl. Acad. Sci. USA* 90:7427-7428; Marasco et al. (1993) *Proc. Natl. Acad. Sci. USA* 90:7889-7893; Biocca et al. (1994) *Biotechnology* (NY) 12:396-399; Chen et al. (1994) *Hum. Gene Ther.*

5:595-601; Duan et al. (1994) *Proc. Natl. Acad. Sci. USA* 91:5075-5079; Chen et ah (1994) *Proc. Natl. Acad. Sci. USA* 91:5932-5936; Beerli et al. (1994) *J. Biol. Chem.* 269: 23931-23936; Beerli et al. (1994) *Biochem. Biophys. Res. Commun.* 204:666-672; Mhashilkar et al. (1995) *EMBO J.* 14:1542-1551; Richardson et al. (1995) *Proc. Natl. Acad. Sci. USA* 92:3137-3141; PCT Publication No. WO 94/02610; and PCT Publication No. WO 95/03832).

Additionally, fully human antibodies could be made against a PD-1 ligand or a functional variant thereof. Fully human antibodies can be made in mice that are transgenic for human immunoglobulin genes, e.g. according to Hogan, et al., "Manipulating the Mouse Embryo: A Laboratory Manual," Cold Spring Harbor Laboratory. Briefly, transgenic mice are immunized with purified PD-1 ligand or functional variant thereof. Spleen cells are harvested and fused to myeloma cells to produce hybridomas. Hybridomas are selected based on their ability to produce antibodies which bind to PD-1 ligand or a functional variant thereof. Fully human antibodies would reduce the immunogenicity of such antibodies in a human.

In one embodiment, an antibody for use in the instant presently disclosed subject matter is a bispecific antibody. A bispecific antibody has binding sites for two different antigens within a single antibody polypeptide. Antigen binding may be simultaneous or sequential. Triomas and hybrid hybridomas are two examples of cell lines that can secrete bispecific antibodies. Examples of bispecific antibodies produced by a hybrid hybridoma or a trioma are disclosed in U.S. Pat. No. 4,474,893. Bispecific antibodies have been constructed by chemical means (Staerz et al. (1985) *Nature* 314:628, and Perez et al. (1985) *Nature* 316:354) and hybridoma technology (Staerz and Bevan (1986) *Proc. Natl. Acad. Sci. USA,* 83:1453, and Staerz and Bevan (1986) *Immunol. Today* 7:241). Bispecific antibodies are also described in U.S. Pat. No. 5,959,084. Fragments of bispecific antibodies are described in U.S. Pat. No. 5,798,229.

Bispecific agents can also be generated by making heterohybridomas by fusing hybridomas or other cells making different antibodies, followed by identification of clones producing and co-assembling both antibodies. They can also be generated by chemical or genetic conjugation of complete immunoglobulin chains or portions thereof such as Fab and Fv sequences. The antibody component can bind to PD-1 ligand or a functional variant thereof. In one embodiment, the bispecific antibody could specifically bind to both PD-1 ligand or a functional variant thereof and a PD-1 polypeptide or a functional variant thereof.

Yet another aspect of the presently disclosed subject matter pertains to antibodies that are obtainable by a process comprising, immunizing an animal with an immunogenic PD-1 ligand or a functional variant thereof, or an immunogenic portion thereof unique to the PD-1 ligand, and then isolating from the animal antibodies that specifically bind to the polypeptide.

iii. Small Molecules

In one embodiment, the agent that inhibits the interaction between a PD-1 ligand and a PD-1 polypeptide is a small molecule. Accordingly, the presently disclosed subject matter also encompasses small molecules that can modulate interactions, e.g., the interaction between PD-1 ligand and a PD-1 polypeptide, or functional variants thereof. The small molecules of the present presently disclosed subject matter can be obtained using any of the numerous approaches in combinatorial library methods known in the art, including: spatially addressable parallel solid phase or solution phase libraries; synthetic library methods requiring deconvolution; the 'one-bead one-compound' library method; and synthetic library methods using affinity chromatography selection. (Lam (1997) *Anticancer Drug Des.* 12:145).

Examples of methods for the synthesis of molecular libraries can be found in the art, for example in: DeWitt et al. (1993) *Proc. Natl. Acad. Sci. USA* 90:6909; Erb et al. (1994) *Proc. Natl. Acad. Sci. USA* 91:11422; Zuckermann et al. (1994) *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994)*J. Med. Chem.* 37:1233.

Libraries of compounds can be presented in solution (e.g., Houghten (1992) *Biotechniques* 13:412-421), or on beads (Lam (1991) *Nature* 354:82-84), chips (Fodor (1993) *Nature* 364:555-556), bacteria (U.S. Pat. No. 5,223,409), spores (U.S. Pat. No. 5,223,409), plasmids (Cull et al. (1992) *Proc. Natl. Acad. Sci. USA* 89:1865-1869) or on phage (Scott and Smith (1990) *Science* 249:386-390); Devlin (1990) *Science* 249:404-406; Cwirla et al. (1990) *Proc. Natl. Acad. Sci. USA* 87:6378-6382; Felici (1991)*J. Mol. Biol.* 222:301-310; U.S. Pat. No. 5,223,409). Compounds can be screened in cell based or non-cell based assays. Compounds can be screened in pools (e.g. multiple compounds in each testing sample) or as individual compounds.

In one embodiment, the small molecule binds to the binding site involved in the PD-1 ligand/PD-1 polypeptide interaction, or interactions between functional variants thereof.

iv. Peptides

In one embodiment, the agent that inhibits the interaction between a PD-1 ligand and a PD-1 polypeptide, or interactions between functional variants thereof, is a peptide. Accordingly, in another aspect of this presently disclosed subject matter, peptides or peptide mimetics can be used to antagonize the interaction between a PD-1 polypeptide and a PD-1 ligand, or functional variants thereof. In one embodiment, functional variants of PD-1 polypeptides or PD-1 ligands which function as a modulating agent for the respective full length protein, can be identified by screening combinatorial libraries of mutants, e.g., truncation mutants, for antagonist activity. In one embodiment, a variegated library of PD-1 polypeptides or PD-1 ligands functional variants is generated by combinatorial mutagenesis at the nucleic acid level and is encoded by a variegated gene library. A variegated library of PD-1 polypeptides or PD-1 ligand functional variants can be produced, for instance, by enzymatically ligating a mixture of synthetic oligonucleotides into gene sequences such that a degenerate set of potential polypeptide sequences is expressible as individual polypeptides containing the set of polypeptide sequences therein. There are a variety of methods which can be used to produce libraries of polypeptide variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential polypeptide sequences. Methods for synthesizing degenerate oligonucleotides are known in the art (e.g., Narang (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477.

In addition, libraries of fragments of a polypeptide coding sequence can be used to generate a variegated population of polypeptide fragments for screening and subsequent selection of variants of a given polypeptide. In one embodiment, a library of coding sequence fragments can be generated by treating a double stranded PCR fragment of a polypeptide coding sequence with a nuclease under conditions wherein nicking occurs only about once per polypeptide, denaturing the double stranded DNA, renaturing the DNA to form double stranded DNA which can include sense/antisense pairs from different nicked products, removing single stranded portions from reformed duplexes by treatment with Si nuclease, and ligating the resulting fragment library into an expression vector. By this method, an expression library can be derived which encodes N-terminal, C-terminal and internal fragments of various sizes of the polypeptide.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of polypeptides. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify functional variants of PD-1 polypeptides and/or PD-1 ligands (Arkin and Youvan (1992) *Proc. Natl. Acad. Sci. USA* 89:7811-7815; Delagrave et al. (1993) *Protein Eng.* 6(3):327-331). In one embodiment, cell based assays can be exploited to analyze a variegated polypeptide library. For example, a library of expression vectors can be transfected into a cell line which ordinarily synthesizes a PD-1 polypeptide, a PD-1 ligand, or functional variants thereof. The transfected cells are then cultured such that the full length polypeptide and a particular mutant polypeptide are produced and the effect of expression of the mutant on the full length polypeptide activity in cell supernatants can be detected, e.g., by any of a number of functional assays. Plasmid DNA can then be recovered from the cells which score for inhibition, or alternatively, potentiation of full length polypeptide activity, and the individual clones further characterized.

Systematic substitution of one or more amino acids of a polypeptide amino acid sequence with a D-amino acid of the same type (e.g., D-lysine in place of L-lysine) can be used to generate more stable peptides. In addition, constrained peptides comprising a polypeptide amino acid sequence of interest or a substantially identical sequence variation can be generated by methods known in the art (Rizo and Gierasch (1992) *Annu. Rev. Biochem.* 61:387); for example, by adding internal cysteine residues capable of forming intramolecular disulfide bridges which cyclize the peptide.

The amino acid sequences disclosed herein will enable those of skill in the art to produce polypeptides corresponding peptide sequences and sequence variants thereof. Such polypeptides can be produced in prokaryotic or eukaryotic host cells by expression of polynucleotides encoding the peptide sequence, frequently as part of a larger polypeptide. Alternatively, such peptides can be synthesized by chemical methods. Methods for expression of heterologous proteins in recombinant hosts, chemical synthesis of polypeptides, and in vitro translation are well known in the art and are described further in Maniatis et al. *Molecular Cloning: A Laboratory Manual* (1989), 2nd Ed., Cold Spring Harbor, N.Y.; Berger and Kimmel, Methods in Enzymology, Volume 152, Guide to Molecular Cloning Techniques (1987), Academic Press, Inc., San Diego, Calif.; Merrifield, J. (1969) *J. Am. Chem. Soc.* 91:501; Chaiken I. M. (1981) *CRC Crit. Rev. Biochem.* 11: 255; Kaiser et al. (1989) *Science* 243:187; Merrifield (1986) *Science* 232:342; Kent (1988) *Annu. Rev. Biochem.* 57:957; and Offord (1980) Semisynthetic Proteins, Wiley Publishing).

In one embodiment, the peptide has an amino acid sequence identical or similar to a PD-1 ligand polypeptide or functional variant thereof. In one embodiment, the peptide competes with the PD-1 ligand or functional variant thereof for binding to a PD-1 polypeptide or functional variant thereof.

Peptides can be produced, typically by direct chemical synthesis, and used e.g., as antagonists of the interaction between a PD-1 polypeptide and PD-1 ligand or functional variants thereof. Peptides can be produced as modified peptides, with nonpeptide moieties attached by covalent linkage to the N-terminus and/or C-terminus. In certain preferred embodiments, either the carboxy-terminus or the amino-terminus, or both, are chemically modified. The most common modifications of the terminal amino and carboxyl groups are acetylation and amidation, respectively. Amino-terminal modifications such as acylation (e.g., acetylation) or alkylation (e.g., methylation) and carboxy-terminal-modifications such as amidation, as well as other terminal modifications, including cyclization, can be incorporated into various embodiments of the presently disclosed subject matter. Certain amino-terminal and/or carboxy-terminal modifications and/or peptide extensions to the core sequence can provide advantageous physical, chemical, biochemical, and pharmacological properties, such as: enhanced stability, increased potency and/or efficacy, resistance to serum proteases, desirable pharmacokinetic properties, and others. Peptides disclosed herein can be used therapeutically to treat disease, e.g., by altering costimulation in a subject.

Peptidomimetics (Fauchere (1986) *Adv. Drug Res.* 15:29; Veber and Freidinger (1985) TINS p. 392; and Evans et al. (1987) *J. Med. Chem.* 30:1229) are usually developed with the aid of computerized molecular modeling. Peptide mimetics that are structurally similar to therapeutically useful peptides can be used to produce an equivalent therapeutic or prophylactic effect. Generally, peptidomimetics are structurally similar to a paradigm polypeptide (i.e., a polypeptide that has a biological or pharmacological activity), such as a human PD-1 polypeptide, a PD-1 ligand, or functional variants thereof, but have one or more peptide linkages optionally replaced by a linkage selected from the group consisting of: —CH2NH—, —CH2S—, —CH2—CH2—, —CH═CH— (cis and trans), —COCH2—, —CH(OH)CH2—, and —CH2SO—, by methods known in the art and further described in the following references: Spatola, A. F. in "*Chemistry and Biochemistry of Amino Acids, Peptides, and Proteins*" Weinstein, B., ed., Marcel Dekker, New York, p. 267 (1983); Spatola, A. F., Vega Data (March 1983), Vol. 1, Issue 3, "Peptide Backbone Modifications" (general review); Morley (1980) *Trends Pharm. Sci.* pp. 463-468 (general review); Hudson et al. (1979) *Int. J. Pept. Prot. Res.* 14:177-185 (—CH2NH—, CH2CH2—); Spatola et al. (1986) *Life Sci.* 38:1243-1249 (CH2-S); Hann (1982) *J. Chem. Soc. Perkin Trans. I.* 307-314 (—CH—CH—, cis and trans); Almquist et al. (190) *J. Med. Chem.* 23:1392-1398 (—COCH2—); Jennings-White et al. (1982) *Tetrahedron Lett.* 23:2533 (—COCH2—); European Patent App. No. EP 45665 (—CH(OH)CH2—); Holladay et al. (1983) *Tetrahedron Lett.* (1983) 24:4401-4404 (—C(OH)CH2—);

and Hruby (1982) *Life Sci.* (1982) 31:189-199 (CH2-S). A particularly preferred non-peptide linkage is —CH2NH—. Such peptide mimetics may have significant advantages over polypeptide embodiments, including, for example: more economical production, greater chemical stability, enhanced pharmacological properties (half-life, absorption, potency, efficacy, etc.), altered specificity (e.g., a broad-spectrum of biological activities), reduced antigenicity, and others. Labeling of peptidomimetics usually involves covalent attachment of one or more labels, directly or through a spacer (e.g., an amide group), to non-interfering position(s) on the peptidomimetic that are predicted by quantitative structure-activity data and/or molecular modeling. Such non-interfering positions generally are positions that do not form direct contacts with the macropolypeptides(s) to which the peptidomimetic binds to produce the therapeutic effect. Derivitization (e.g., labeling) of peptidomimetics should not substantially interfere with the desired biological or pharmacological activity of the peptidomimetic.

v. Fusion Proteins

In one embodiment, the agent that inhibits the interaction between a PD-1 ligand and a PD-1 polypeptide is a fusion protein. Accordingly, a "chimeric protein" or "fusion protein" comprises a PD-1 polypeptide or PD-1 ligand or functional variants thereof operatively linked to a non-PD-1 polypeptide or non-PD-1 ligand. A "non-PD-1 polypeptide or non-PD-1 ligand" refers to a polypeptide having an amino acid sequence corresponding to a protein which is not substantially homologous to the respective PD-1 polypeptide or PD-1 ligand or functional variants thereof, e.g., a protein which is different from the PD-1 polypeptide or PD-1 ligand or functional variants thereof, and which is derived from the same or a different organism. In a preferred embodiment, the fusion protein comprises at least one biologically active portion of a PD-1 polypeptide or PD-1 ligand or functional variants thereof, e.g., an extracellular domain. Within the fusion protein, the term "operatively linked" is intended to indicate that the amino acid sequences for a PD-1 polypeptide or PD-1 ligand or functional variants thereof and the amino acid sequences for the non-PD-1 polypeptide or non-PD-1 ligand or functional variants thereof are fused in-frame to each other in such a way as to preserve functions exhibited when expressed independently of the fusion. The non-PD-1 polypeptide or non-PD-1 ligand or functional variants thereof can be fused to the N-terminus or C-terminus of the sequences for the PD-1 polypeptide or PD-1 ligand or functional variants thereof, respectively.

Such a fusion protein can be produced by recombinant expression of a nucleotide sequence encoding the first peptide and a nucleotide sequence encoding the second peptide. The second peptide may optionally correspond to a moiety that alters the solubility, affinity, stability or valency of the first peptide, for example, an immunoglobulin constant region. Preferably, the first peptide consists of a portion of the PD-1 polypeptide or PD-1 ligand or functional variants thereof that is sufficient to modulate costimulation or inhibition of activated immune cells. In another preferred embodiment, the first peptide consists of a portion of a biologically active molecule (e.g the extracellular portion of the polypeptide or the ligand binding portion). The second peptide can include an immunoglobulin constant region, for example, a human Cγ1 domain or Cγ4 domain (e.g., the hinge, CH2 and CH3 regions of human IgCγ1, or human IgCγ4, see e.g., U.S. Pat. Nos. 5,116,964; 5,580,756; 5,844,095 and the like). Such constant regions may retain regions which mediate effector function (e.g. Fc receptor binding) or may be altered to reduce effector function. A resulting fusion protein may have altered solubility, binding affinity, stability and/or valency (i.e., the number of binding sites available per polypeptide) as compared to the independently expressed first peptide, and may increase the efficiency of protein purification. Fusion proteins and peptides produced by recombinant techniques can be secreted and isolated from a mixture of cells and medium containing the protein or peptide. Alternatively, the protein or peptide can be retained cytoplasmically and the cells harvested, lysed and the protein isolated. A cell culture typically includes host cells, media and other byproducts. Suitable media for cell culture are well known in the art. Protein and peptides can be isolated from cell culture media, host cells, or both using techniques known in the art for purifying proteins and peptides. Techniques for transfecting host cells and purifying proteins and peptides are known in the art.

Particularly preferred Ig fusion proteins include the extracellular domain portion or variable region-like domain of a human PD-1 polypeptide or PD-1 ligand or functional variants thereof coupled to an immunoglobulin constant region (e.g., the Fc region). The immunoglobulin constant region may contain genetic modifications which reduce or eliminate effector activity inherent in the immunoglobulin structure. For example, DNA encoding the extracellular portion of a human PD-1 polypeptide or PD-1 ligand or functional variants thereof can be joined to DNA encoding the hinge, CH2 and CH3 regions of human IgGγ1 and/or IgGγ4 modified by site directed mutagenesis, e.g., as taught in PCT Patent App. Pub. No. WO 97/28267.

Preferably, a fusion protein of the presently disclosed subject matter is produced by standard recombinant DNA techniques. For example, DNA fragments coding for the different polypeptide sequences are ligated together in-frame in accordance with conventional techniques, for example employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (e.g., *Current Protocols in Molecular Biology*, eds. Ausubel et al. John Wiley & Sons: 1992). A polypeptide encoding nucleic acid can be cloned into such an expression vector such that the fusion moiety is linked in-frame to the encoding sequences for a human PD-1 polypeptide or PD-1 ligand or functional variants thereof.

In another embodiment, the fusion protein contains a heterologous signal sequence at its N-terminus. In certain host cells (e.g., mammalian host cells), expression and/or secretion of a polypeptide can be increased through use of a heterologous signal sequence.

In a preferred embodiment, the fusion protein binds to a PD-1 polypeptide or PD-1 ligand or functional variant thereof and blocks the interaction of a PD-1 polypeptide with a PD-1 ligand, or the interaction between functional variants thereof.

The fusion proteins of the presently disclosed subject matter can be used as immunogens to produce antibodies in a subject. Such antibodies may be used to purify the respective natural polypeptides from which the fusion proteins were generated, or in screening assays to identify polypeptides which inhibit the interaction of a PD-1 polypeptide with a PD-1 ligand, or the interaction between functional variants thereof.

C. Pharmaceutically Acceptable Carriers and Formulations

Immunogenic compositions of the presently disclosed subject matter may comprise one or more pneumococcal polysaccharide antigens; an effective amount of an agent that inhibits the interaction between a PD-1 ligand and a PD-1 polypeptide; and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active agents, use thereof in the compositions is contemplated. Supplementary active agents can also be incorporated into the compositions.

A pharmaceutical composition of the presently disclosed subject matter is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition should be sterile and should be fluid to the extent that easy syringeability exists. It must be stable under the conditions of manufacture and storage and should be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it is preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active agents (e.g., one or more pneumococcal polysaccharide antigens and an effective amount of an agent that inhibits the interaction between a PD-1 ligand and a PD-1 polypeptide) in the required amount in an appropriate solvent with one or a combination of ingredients enumerated above, as required, followed by filtered sterilization. Generally, dispersions are prepared by incorporating the active agents into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active agents can be incorporated with excipients and used in the form of tablets, troches, or capsules. Oral compositions can also be prepared using a fluid carrier for use as a mouthwash, wherein the agents in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or agents of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the agents are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active agents are formulated into ointments, salves, gels, or creams as generally known in the art.

The agents can also be prepared in the form of suppositories (e.g., with conventional suppository bases such as cocoa butter and other glycerides) or retention enemas for rectal delivery.

In one embodiment, modulatory agents are prepared with carriers that will protect the agents against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations should be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active agents calculated to produce the desired therapeutic effect in association with the required pharmaceutical carrier. The specification for the dosage unit forms of the presently disclosed subject matter are dictated by, and directly dependent on, the unique characteristics of the active agents, the particular therapeutic effect to be achieved, and the limitations inherent in the art of agentsing such an active agents for the treatment of individuals.

Toxicity and therapeutic efficacy of such agents can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Agents which exhibit large therapeutic indices are preferred. While agents that exhibit toxic side effects can be used, care should be taken to design a delivery system that targets such agents to the site of affected tissue in order to minimize potential damage to uninfected cells and, thereby, reduce side effects.

The data obtained from the cell culture assays and animal studies can be used in formulating a range of dosage for use in humans. The dosage of such agents lies preferably within a range of circulating concentrations that include the ED50 with little or no toxicity. The dosage may vary within this range depending upon the dosage form employed and the route of administration utilized. For any agents used in the method of the presently disclosed subject matter, the therapeutically effective dose can be estimated initially from cell culture assays. A dose can be formulated in animal models to achieve a circulating plasma concentration range that includes the IC50 (i.e., the concentration of the test agents which achieves a half-maximal inhibition of symptoms) as determined in cell culture. Such information can be used to more accurately determine useful doses in humans. Levels in plasma can be measured, for example, by high performance liquid chromatography.

The above described modulating agents may be administered in the form of expressible nucleic acids which encode said agents. Such nucleic acids and compositions in which they are contained, are also encompassed by the present presently disclosed subject matter. For instance, the nucleic acid molecules of the presently disclosed subject matter can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *Proc. Natl. Acad. Sci. USA* 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

III. Kits or Pharmaceutical Systems

The presently disclosed agents and compositions can be assembled into kits or pharmaceutical systems for use in treating or preventing diseases, disorders, or conditions associated with a bacterial infection caused by *Streptococcus pneumoniae* in a subject in need thereof. In some embodiments, the presently disclosed subject matter is directed to a kit or pharmaceutical system for increasing protective antibody levels induced by one or more pneumococcal polysaccharide antigens in a subject in need thereof, the kit comprising: a) a pneumococcal polysaccharide vaccine comprising one or more pneumococcal polysaccharide antigens; b) an agent that inhibits the interaction between a PD-1 ligand and a PD-1 polypeptide; and c) instructions for administration of the pneumococcal polysaccharide vaccine and the agent to the subject. A kit or pharmaceutical system for treating a bacterial infection caused by *Streptococcus pneumoniae* in a subject in need thereof is also provided, the kit comprising: a) a pneumococcal polysaccharide vaccine comprising one or more pneumococcal polysaccharide antigens; b) an agent that inhibits the interaction between a PD-1 ligand and a PD-1 polypeptide; and c) instructions for administration of the pneumococcal polysaccharide vaccine and the agent to the subject.

In some embodiments, the presently disclosed kits or pharmaceutical systems comprise one or more containers, including, but not limited to a vial, tube, ampule, bottle and the like, for containing a pneumococcal polysaccharide vaccine comprising one or more pneumococcal polysaccharide antigens and an agent that inhibits the interaction between a PD-1 ligand and a PD-1 polypeptide. The one or more containers also can be carried within a suitable carrier, such as a box, carton, tube or the like. Such containers can be made of plastic, glass, laminated paper, metal foil, or other materials suitable for holding medicaments.

In some embodiments, the container can hold a composition that is by itself or when combined with another composition effective for treating or preventing the condition and may have a sterile access port (for example the container may be an intravenous solution bag or a vial having a stopper pierceable by a hypodermic injection needle). Alternatively, or additionally, the article of manufacture may further include a second (or third) container including a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The presently disclosed kits or pharmaceutical systems also can include associated instructions for using a pneumococcal polysaccharide vaccine comprising one or more pneumococcal polysaccharide antigens and an agent that inhibits the interaction between a PD-1 ligand and a PD-1 polypeptide for treating or preventing a disease, disorder, or condition associated with a bacterial infection caused by *Streptococcus pneumonia* in a subject in need thereof. In some embodiments, the instructions include one or more of the following: a description of the active agents; a dosage schedule and administration for treating or preventing a disease, disorder, or condition associated with a bacterial infection caused by *Streptococcus pneumonia* in a subject in need thereof; precautions; warnings; indications; counter-indications; overdosage information; adverse reactions; animal pharmacology; clinical studies; and references. The instructions can be printed directly on a container (when present), as a label applied to the container, as a separate sheet, pamphlet, card, or folder supplied in or with the container.

IV. General Definitions

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

As used herein, the term "modulate" includes up-regulation and down-regulation, e.g., enhancing or inhibiting a response. As used herein, the term "inhibit" includes the decrease, limitation, or blockage, of, for example a particular action, function, or interaction.

As used herein, the term "immune cell" refers to cells that play a role in the immune response Immune cells are of hematopoietic origin, and include lymphocytes, such as B cells and T cells; natural killer cells; myeloid cells, such as monocytes, macrophages, eosinophils, mast cells, basophils, and granulocytes.

As used herein, the term "T cell" includes CD4+T cells and CD8+T cells. The term T cell also includes both T helper 1 type T cells and T helper 2 type T cells. The term "antigen presenting cell" includes professional antigen presenting cells (e.g., B lymphocytes, monocytes, dendritic cells, Langerhans cells) as well as other antigen presenting cells (e.g., keratinocytes, endothelial cells, astrocytes, fibroblasts, oligodendrocytes).

As used herein, the term "immune response" includes T cell mediated and/or B cell mediated immune responses that are influenced by modulation of T cell costimulation. Exemplary immune responses include T cell responses, e.g., cytokine production, and cellular cytotoxicity. In addition, the term immune response includes immune responses that are indirectly affected by T cell activation, e.g., antibody production (humoral responses) and activation of cytokine responsive cells, e.g., macrophages.

As used herein, the term "costimulatory receptor" includes receptors which transmit a costimulatory signal to a immune cell, e.g., CD28. As used herein, the term "inhibitory receptors" includes receptors which transmit a negative signal to an immune cell (e.g., CTLA4 or PD-1). An inhibitory signal as transduced by an inhibitory receptor can occur even if a costimulatory receptor (such as CD28) is not present on the immune cell and, thus, is not simply a function of competition between inhibitory receptors and costimulatory receptors for binding of costimulatory polypeptides (Fallarino et al. (1998) *J. Exp. Med.* 188:205). Transmission of an inhibitory signal to an immune cell can result in unresponsiveness or anergy or programmed cell death in the immune cell. Preferably transmission of an inhibitory signal operates through a mechanism that does not involve apoptosis. As used herein the term "apoptosis" includes programmed cell death which can be characterized using techniques which are known in the art. Apoptotic cell death can be characterized, e.g., by cell shrinkage, membrane blebbing and chromatin condensation culminating in cell fragmentation. Cells undergoing apoptosis also display a characteristic pattern of internucleosomal DNA cleavage.

Depending upon the form of the PD-1 ligand polypeptide that binds to a receptor, a signal can either be transmitted (e.g., by a multivalent form of a PD-1 ligand polypeptide or a form of a PD-1 ligand polypeptide that binds to Fc receptors that results in crosslinking of receptor) or a signal can be inhibited (e.g., by a soluble, monovalent form of a PD-1 ligand polypeptide or a form of PD-1 ligand polypeptide lacking Fc receptors), for instance by competing with activating forms of PD-1 ligand polypeptides for binding to the receptor. However, there are instances in which a soluble polypeptide can be stimulatory. The effects of a modulatory agent can be easily demonstrated using routine screening assays as described herein.

As used herein, the term "costimulate," as used with reference to activated immune cells, includes the ability of a costimulatory polypeptide to provide a second, non-activating receptor mediated signal (a "costimulatory signal") that induces proliferation or effector function. For example, a costimulatory signal can result in cytokine secretion, e.g., in a T cell that has received a T cell-receptor-mediated signal. Immune cells that have received a cell-receptor mediated signal, e.g., via an activating receptor are referred to herein as "activated immune cells."

As used herein, the term "activating receptor" includes immune cell receptors that bind antigen, complexed antigen (e.g., in the context of MHC polypeptides), or bind to antibodies. Such activating receptors include T cell receptors (TCR), B cell receptors (BCR), cytokine receptors, LPS receptors, complement receptors, and Fc receptors.

T cell receptors are present on T cells and are associated with CD3 polypeptides. T cell receptors are stimulated by antigen in the context of MHC polypeptides (as well as by polyclonal T cell activating reagents). T cell activation via the TCR results in numerous changes, e.g., protein phosphorylation, membrane lipid changes, ion fluxes, cyclic nucleotide alterations, RNA transcription changes, protein synthesis changes, and cell volume changes.

B cell receptors are present on B cells. B cell antigen receptors are a complex between membrane Ig (mIg) and other transmembrane polypeptides (e.g., Igα and Id). The signal transduction function of mIg is triggered by crosslinking of receptor polypeptides by oligomeric or multimeric antigens. B cells can also be activated by anti-immunoglobulin antibodies. Upon BCR activation, numerous changes occur in B cells, including tyrosine phosphorylation.

Fc receptors are found on many cells which participate in immune responses. Fc receptors (FcRs) are cell surface receptors for the Fc portion of immunoglobulin polypeptides (Igs). Among the human FcRs that have been identified so far are those which recognize IgG (designated Fcγ R), IgE (Fcε R1), IgA (Fcα), and polymerized IgM/A (Fcμα R). FcRs are found in the following cell types: Fcε R I (mast cells), Fcε R.II (many leukocytes), Fcα R (neutrophils), and Fcμα R (glandular epithelium, hepatocytes) (Hogg (1988) *Immunol. Today* 9:185-86). The widely studied FcγRs are central in cellular immune defenses, and are responsible for stimulating the release of mediators of inflammation and hydrolytic enzymes involved in the pathogenesis of autoimmune disease (Unkeless et al. (1988) *Annu. Rev. Immunol.* 6:251-81). The FcγRs provide a crucial link between effector cells and the lymphocytes that secrete Ig, since the macrophage/monocyte, polymorphonuclear leukocyte, and natural killer (NK) cell FcγRs confer an element of specific recognition mediated by IgG. Human leukocytes have at least three different receptors for IgG: h Fcγ RI (found on monocytes/macrophages), hFcγ RII (on monocytes, neutrophils, eosinophils, platelets, possibly B cells, and the K562 cell line), and Fcγ III (on NK cells, neutrophils, eosinophils, and macrophages).

With respect to T cells, transmission of a costimulatory signal to a T cell involves a signaling pathway that is not inhibited by cyclosporine A. In addition, a costimulatory signal can induce cytokine secretion (e.g., IL-2 and/or IL-10) in a T cell and/or can prevent the induction of unresponsiveness to antigen, the induction of anergy, or the induction of cell death in the T cell.

As used herein, the term "inhibitory signal" refers to a signal transmitted via an inhibitory receptor (e.g., PD-1) for a polypeptide on a immune cell. Such a signal antagonizes a signal via an activating receptor (e.g., via a TCR, CD3, BCR, or Fc polypeptide) and can result in, e.g., inhibition of second messenger generation; an inhibition of proliferation; an inhibition of effector function in the immune cell, e.g., reduced phagocytosis, reduced antibody production, reduced cellular cytotoxicity, the failure of the immune cell to produce mediators, (such as cytokines (e.g., IL-2) and/or mediators of allergic responses); or the development of anergy.

As used herein, the term "unresponsiveness" includes refractivity of immune cells to stimulation, e.g., stimulation via an activating receptor or a cytokine. Unresponsiveness can occur, e.g., because of exposure to immunosuppressants or exposure to high doses of antigen. As used herein, the term "anergy" or "tolerance" includes refractivity to activating receptor-mediated stimulation. Such refractivity is generally antigen-specific and persists after exposure to the tolerizing antigen has ceased. For example, anergy in T cells (as opposed to unresponsiveness) is characterized by lack of cytokine production, e.g., IL-2. T cell anergy occurs when T cells are exposed to antigen and receive a first signal (a T cell receptor or CD-3 mediated signal) in the absence of a second signal (a costimulatory signal). Under these conditions, reexposure of the cells to the same antigen (even if reexposure occurs in the presence of a costimulatory polypeptide) results in failure to produce cytokines and, thus, failure to proliferate. Anergic T cells can, however, proliferate if cultured with cytokines (e.g., IL-2). For example, T cell anergy can also be observed by the lack of IL-2 production by T lymphocytes as measured by ELISA or by a proliferation assay using an indicator cell line. Alternatively, a reporter gene construct can be used. For example, anergic T cells fail to initiate IL-2 gene transcription induced by a heterologous promoter under the control of the 5' IL-2 gene enhancer or by a multimer of the AP1 sequence that can be found within the enhancer (Kang et al. (1992) *Science* 257:1134).

As used herein, a "naturally-occurring" nucleic acid polypeptide refers to an RNA or DNA polypeptide having a nucleotide sequence that occurs in nature (e.g., encodes a natural protein).

As used herein, an "antisense" nucleic acid polypeptide comprises a nucleotide sequence which is complementary to a "sense" nucleic acid encoding a protein, e.g., complementary to the coding strand of a double-stranded cDNA polypeptide, complementary to an mRNA sequence or complementary to the coding strand of a gene. Accordingly, an antisense nucleic acid polypeptide can hydrogen bond to a sense nucleic acid polypeptide.

As used herein, the term "coding region" refers to regions of a nucleotide sequence comprising codons which are translated into amino acid residues, whereas the term "noncoding region" refers to regions of a nucleotide sequence that are not translated into amino acids (e.g., 5' and 3' untranslated regions).

As used herein, the term "vector" refers to a nucleic acid capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" or simply "expression vectors". In general, expression vectors of utility in recombinant DNA techniques are often in the form of plasmids. In the present specification, "plasmid" and "vector" may be used interchangeably as the plasmid is the most commonly used form of vector. However, the presently disclosed subject matter is intended to include such other forms of expression vectors, such as viral vectors (e.g., replication defective retroviruses, adenoviruses and adeno-associated viruses), which serve equivalent functions.

As used herein, the term "host cell" is intended to refer to a cell into which a nucleic acid of the presently disclosed subject matter, such as a recombinant expression vector of the presently disclosed subject matter, has been introduced. The terms "host cell" and "recombinant host cell" are used interchangeably herein. It should be understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

As used herein, an "isolated protein" refers to a protein that is substantially free of other proteins, cellular material, separation medium, and culture medium when isolated from cells or produced by recombinant DNA techniques, or chemical precursors or other chemicals when chemically synthesized. An "isolated" or "purified" protein or biologically active portion thereof is substantially free of cellular material or other contaminating proteins from the cell or tissue source from which the antibody, polypeptide, peptide or fusion protein is derived, or substantially free from chemical precursors or other chemicals when chemically synthesized. The language "substantially free of cellular material" includes preparations of PD-1 ligand, PD-1 polypeptide, of functional variants thereof in which the protein is separated from cellular components of the cells from which it is isolated or recombinantly produced. In one embodiment, the language "substantially free of cellular material" includes preparations of PD-1 ligand, PD-1 polypeptide, or functional variants thereof, having less than about 30% (by dry weight) of non-PD-1 ligand or non-PD-1 polypeptide, or functional variants thereof (also referred to herein as a "contaminating protein"), more preferably less than about 20% of contaminating protein, still more preferably less than about 10% of contaminating protein, and most preferably less than about 5% contaminating protein. When antibody, polypeptide, peptide or fusion protein or biologically active portion thereof is recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of antibody, polypeptide, peptide or fusion protein in which the protein is separated from chemical precursors or other chemicals which are involved in the synthesis of the protein. In one embodiment, the language "substantially free of chemical precursors or other chemicals" includes preparations of antibody, polypeptide, peptide or fusion protein having less than about 30% (by dry weight) of chemical precursors or non-antibody, polypeptide, peptide or fusion protein chemicals, more preferably less than about 20% chemical precursors or non-antibody, polypeptide, peptide or fusion protein chemicals, still more preferably less than about 10% chemical precursors or non-antibody, polypeptide, peptide or fusion protein chemicals, and most preferably less than about 5% chemical precursors or non-antibody, polypeptide, peptide or fusion protein chemicals.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make agents of the disclosure by other methods.

Example 1

Despite its emergence as a promising therapeutic target, very little is known regarding the role the immunoinhibitory PD-1 receptor or its ligands (PD-L; B7-H1 and B7-DC) play during extracellular bacterial infections. In the current study, the role PD-1 and its ligands play in protection against respiratory challenge with invasive S. pneumoniae was examined.

As described in more detail below, the data clearly support a role for PD-1 in suppressing the protective (PPS-specific) TI IgG response to S. pneumoniae infection and purified PPS immunization, but not the TD Ab response to PPS-protein conjugate. Following native PPS immunization, PPS-specific B cell proliferation (as assessed by Ki-67 staining and BrdU incorporation) and the frequency of cells undergoing IgG switching and plasmablast differentiation was significantly increased in PD-1$^{-/-}$ mice. PD-1 expression was induced on activated PPS-specific B cells and was key for suppression, as PD-1$^{-/-}$ B cells reconstituted significantly higher PPS-specific IgG responses in B cell-deficient mice relative to wildtype B cells. Finally, B7-H1$^{-/-}$ and B7-DC$^{-/-}$ mice produced wildtype PPS-specific Ab responses. However, dual B7-H1 and B7-DC mAb blockade, similar to single PD-1 mAb blockade, significantly increased PPS-specific IgG responses in wildtype mice. Without being bound by theory, it is believed that these results provide support for redundant overlapping roles for B7-H1 and B7-DC in PD-1-mediated suppression of polysaccharide-specific Ab responses.

In summary, the results highlight a critical role for B cell-expressed PD-1 in suppressing humoral immune responses essential for protection against pneumococcal infections and provide support for new therapeutic opportunities to improve vaccines against encapsulated pathogens as well as other polysaccharide-based vaccines.

Methods

Mice: C57BL/6 and μMT mice were obtained from Jackson Laboratories (Bar Harbor, Me.). PD-1$^{-/-}$ (Nishimura et al. (1998) Int. Immunol. 10:1563-1572), B7DC$^{-/-}$ (Shin et al. (2005) J. Exp. Med. 201:1531-1541), and B7H1$^{-/-}$ (Dong et al. (2004) Immunity 20:327-336) mice were on a C57BL/6 background. B6.129P2-Ptrpc$^a$Igh$^{tm1Mnz/J}$ (V$_H$B1-8$^{hi}$ transgenic) mice were from Jackson Laboratories. Mice were housed under specific pathogen free conditions, with the exception of infection challenge experiments. Mice were used at 2-4 months of age and were age-matched for experiments (within 1-2 weeks). All studies and procedures were approved by the Wake Forest University Animal Care and Use Committee.

Infections, Immunizations, and In Vivo mAb Blockade: Mice were infected with serotype 3 WU2 strain S. pneumoniae and monitored every 12 hrs for signs of distress as previously described (Haas et al. (2014) J. Infectious Diseases 209:87-97; Haas et al. (2002) Immunity 17:713-723).

In serum transfer experiments, nMT mice challenged with 200 CFU WU2 i.p. received 10 µL of pooled serum (i.p.) from either wild type or PD-1$^{-/-}$ mice harvested 14d post i.n. infection with 10$^6$ CFU WU2. Lung (1 mL PBS homogenate) and blood CFU were determined by plating serial dilutions on 5% TSA-II sheep red blood agar plates (BBL) coated with 4 µg/mL gentamicin and incubated overnight at 37° C.

Mice were immunized i.p. or s.c. with diluted, purified serotype 3 pneumococcal polysaccharide (PPS3) (ATCC; Merck, Whitehouse Station, N.J.) or vaccine-grade PNEUMOVAX23 (PPV23; Merck, Whitehouse Station, N.J.) containing either 0.1 µg (referred to as "0.1 µg dose") or 1 µg (referred to as "1 µg dose") of each of 23 serotypes of PPS or PREVNAR-13 (Pfizer, formerly Wyeth Pharmaceuticals, New York, N.Y.) containing 0.1 µg of each of 13 serotypes of PPS, as previously described (Haas et al. (2014) J. Infectious Diseases 209:87-97). TNP$_{65}$-FICOLL (Biosearch) was administered i.p. (25 µg). PD-1 mAb blockade was performed by administering RMP1-14 or rat IgG2a (eBioscience) i.p. on d1 (200 µg), d3 (100 µg), and d5 (100 µg) post immunization as previously described (Haas et al. (2011) J. Immunol. 187:5183-5195). For ligand blockade experiments, 200 µg B7-H1 (10F.9G2; BioLegend and BioXcell), B7-DC (TY25; BioLegend and BioXcell), or rat IgG control mAbs (BioXcell or eBioscience) was given i.p. on d0, 2, and 4 post immunization.

ELISAs and ELISPOTs: ELISAs were as previously described (Haas (2011) J. Immunol. 187:5183-5195; Haas et al. (2014) J. Infectious Diseases 209:87-97). Serum samples were diluted in TBS containing 1% BSA (TBS-BSA) and incubated with 10 µg/mL cell wall polysaccharide (CWPS, Statens Serum Institut, Denmark) to adsorb non-capsular polysaccharide Abs. PPS3 (ATCC, Manassas, Va.) and PPV23-specific Ab levels were determined by adding diluted serum samples to Maxisorp plates coated with 5 µg/mL native PPS3 or PPV23 in PBS and blocked with TBS-BSA. AP-conjugated polyclonal goat anti-mouse IgM, IgG, IgG3, and IgA Abs (Southern Biotechnology Associates) and pNPP (Sigma, St. Louis, Mo.) were used to detect PPS-specific Ab. For lung Ig levels, lungs were perfused by slowly injecting 5 mL of PBS into the right ventricle of the heart prior to harvest and homogenization in 1 mL PBS. ELISAs were performed using serum dilutions shown to yield OD$_{405\ nm}$ readings that fall within a linear range. ELISA values are reported as relative absorbance units (AU; OD$_{405\ nm}$ reading for serum samples minus OD$_{405nm}$ reading from wells with serum omitted). Endpoint titer PPS3-specific ELISAs were performed using 3-fold serial serum dilutions, with titers reported as the reciprocal dilution yielding OD values that were 2.5-fold over background (serum-omitted) OD$_{405\ nm}$ values. ELISPOTs were performed as previously described (Haas et al. (2014) J. Infectious Diseases 209:87-97).

Flow Cytometry: Single cell suspensions (2×10$^7$/mL) were washed with PBS containing 2% newborn calf serum and then pre-blocked in PBS containing 10 mg/mL CWPS and 0.5 µg/mL Fc block (eBioscience), followed by staining with 25 µg/mL biotinylated PPS3 (PPS3$_{bio}$) at room temperature as previously described (Haas et al. (2014) J. Infectious Diseases 209:87-97). Cells were then washed with PBS containing 2% newborn calf serum and stained with streptavidin-FITC, and a combination of the following mAbs conjugated to different fluorochromes: CD5 (53-7.3), B220 (RA3-6B2), CD86 (GL-1), PD-1 (J43), CD11b (M1/70) (Biolegend); CD19 (1D3, eBioscience); CD138 (281-2, BD Biosciences); and IgG3 (Southern Biotechnology Associates). For Ki-67 staining, extracellular marker and Ag staining was first performed, followed by intracellular staining (Fix/Perm kit in conjunction with SOLA15; eBioscience). Cells were fixed and analyzed using a FACSCantoII cytometer (Becton Dickinson) with FSC-A/FSC-H doublet exclusion. Dump channels for CD11b$^{hi}$ myeloid cells and dump channels for autofluorescence signals (minus fluorochrome) were used to eliminate non-specific signals. Streptavidin-FITC-only staining by B cells served as a negative gating control. Dual Ag staining experiments using PPS3$_{bio}$ plus streptavidin-FITC and ALEXA488-labeled TNP-Ficoll (a neutral sugar) showed PPS3$^+$ B cells selectively bound PPS3 and not TNP-Ficoll. Two million events were collected for Ag-specific B cell analysis. Positive and negative cell populations were determined using non-reactive isotype-matched Ab staining of PPS-binding cells from immune mice. Data was analyzed using FlowJo analysis software (Treestar).

BrdU Staining and Flow Cytometry: Bromodeoxyuridine (BrdU, Sigma, 0.8 mg/mL) was delivered to mice in drinking water as previously described (Haas et al. (2006) J. Immunol. 177: 3063-3073). Single cell suspensions (2×10$^7$/mL) were fixed with 0.5% paraformaldehyde in PBS (pH 7.4), permeabilized with 3N HCl containing 0.5% TWEEN 20, and neutralized with 0.1 M disodium tetraborate. The cells were pre-blocked with unlabeled mIgG1 (20 µg/mL) and intracellular staining performed with mouse anti-BrdU-PE (Bu20A, 4 mg/mL). Cells were washed and blocked in PBS containing 10 µg/mL CWPS and 0.5 µg/mL Fc block, and then stained with 20 µg/mL PPS3$_{bio}$. Cells were washed and stained with streptavidin-FITC and CD19 mAb and analyzed as described above.

Adoptive Transfer Experiments: Splenic B cells were purified using magnetic beads (Dynal) against Thy1.2, DX5, Gr1, F4/80, and 33D1 as previously described (Haas (2011) J. Immunol. 187:5183-5195). Purified B cells (4×10$^7$/mouse) were injected i.p. into µMT mice. Two days later, recipient mice were immunized i.p. with PPV23 containing 0.1 mg of each PPS. Sera were diluted 1:100 for IgM and 1:10 for IgG PPV23-specific detection. Total serum IgM and IgG levels were determined using mouse Ig standards to generate standard curves with linear regression analysis applied to determine Ab concentrations. Peritoneal B-1b cells were isolated from V$_H$B1-8 Tg mice as previously described (Haas (2011) J. Immunol. 187:5183-5195).

Statistical Analysis: Data are shown as means±SEM with differences assessed using Student's t test. Differences in overall survival or survival curves were assessed using the Fisher's Exact Test or the Log Rank test, respectively.

Results

PD-1$^{-/-}$ Mice Exhibited Increased Survival Following Secondary, but not Primary, S. pneumoniae Infection:

To examine the role of PD-1 during acute S. pneumoniae respiratory infection, PD-1$^{-/-}$ and wild type mice were infected intranasally (i.n.) or intraperitoneally (i.p.) with WU2, a highly virulent invasive serotype 3 strain. PD-1$^{-/-}$ and wild type mice displayed similar susceptibility to S. pneumoniae, regardless of dose or route (10$^5$, 10$^6$, or 10$^7$ CFU i.n., and 10$^1$ and 10$^2$ CFU i.p.; FIGS. 1A, 1C). Consistent with this, lung bacterial burdens were comparable between PD-1$^{-/-}$ and wild type mice 3 days post high dose (10$^7$ CFU) i.n. challenge (FIG. 1B) and 10$^6$ CFU i.n. challenge (data not shown). Thus, naïve PD-1$^{-/-}$ and wild type mice display similar susceptibility to primary S. pneumoniae respiratory and systemic infections.

A complicating fatal infection that follows pneumococcal pneumonia is bacteremia. It was therefore tested whether PD-1 influences the outcome of a secondary systemic infection following a primary respiratory infection. Survivors of the $10^6$ WU2 i.n. challenge were infected with a lethal systemic dose ($10^4$ CFU WU2 i.p.; >100 times the $LD_{50}$ ((Haas et al. (2005) *Immunity* 23:7-18) three weeks following the primary respiratory infection. As shown in FIG. 1D, all wild type mice succumbed to secondary (systemic) infection within 36 hours post challenge. Remarkably, PD-1$^{-/-}$ mice exhibited significantly delayed morbidity (48-60 hrs) and significantly reduced mortality relative to wild type mice (p=0.00005). In contrast, all nave PD-1$^{-/-}$ mice succumb to a primary systemic infection 36 hours post-challenge (FIG. 1C), similar to naïve wild type mice and wild type mice previously challenged with a sub-lethal respiratory infection. Thus, PD-1 deficiency did not affect the outcome of primary pneumococcal infection, but provided a significant survival advantage during secondary infection.

PD-1 Deficiency Resulted in Significantly Increased Anti-Capsular IgG Levels Produced in Response to *S. pneumoniae* Infection: Protection against acute systemic pneumococcal infection is largely conferred by pneumococcal-specific Abs, with IgG providing the highest level of protection in mouse studies (Briles et al. (1981) *Nature* 294:88-90). To assess whether adaptive humoral responses to primary infection were altered by PD-1 deficiency, Ab levels specific PPS3, the major component of the thick WU2 pneumococcal capsule, was assessed 14 days post i.n. infection with $10^6$ CFU. PPS3-specific serum IgM, IgG, and IgA levels were increased in wild type and PD-1$^{-/-}$ mice following infection (FIG. 1E). However, PD-1$^{-/-}$ mice produced significantly higher PPS3-specific serum IgG levels (3.4-fold higher IgG titers; p=0.01) relative to wild type mice in response to infection (FIGS. 1E-F). Analysis of perfused lung homogenate Ig levels derived from serum transudation or local synthesis revealed similar findings, with PD-1$^{-/-}$ mice exhibiting significantly higher PPS3-specific lung IgG, but not IgM or IgA, levels compared to wild type mice (FIG. 1G, p=0.02).

To examine whether increased capsule-specific IgG in PD-1$^{-/-}$ mice following sublethal respiratory infection could explain increased protection against subsequent systemic infection (FIG. 1D), the protective capacity of serum harvested from PD-1$^{-/-}$ and wild type mice 14d post infection was assessed in µEMT mice challenged with a lethal systemic infection. µEMT mice that had received sera from PD-1$^{-/-}$ mice had significantly lower bacteremia at 48 hrs (FIG. 1H; p=0.04) and delayed time to death relative to wild type serum recipient mice (FIG. 1I, p=0.026). Thus, PD-1 deficiency significantly increased the level of protective capsule-specific IgG elicited in response to *S. pneumoniae* respiratory infection.

PD-1 Deficiency and PD-1 mAb Blockade Resulted in Significantly Increased IgG Responses to Native PPS, but not Protein-Conjugated PPS: PD-1$^{-/-}$ mice also generated significantly increased PPS3-specific IgG responses following i.p. immunization with purified PPS3 or the PPV23 vaccine (FIGS. 2A-B). Subcutaneous immunization, one of the approved routes of administration for the PPV23 vaccine in humans, elicited 9-fold higher PPS3-specific IgG titers in PD-1$^{-/-}$ mice relative to wild type mice (FIG. 2C; p=0.008). PD-1$^{-/-}$ mice generated significantly higher PPV23-specific IgG levels following both 0.1 µg and 1 µg PPS-equivalent PPV23 doses, with the mean d14 titer increased 2.6-fold (FIG. 2D, p=0.03). Notably, PPS doses outside this range are often tolerizing (Yin et al. (1989) *J. Biol. Response Mod.* 8:190-205). Differences in IgG were largely due to significantly increased PPS-specific IgG3 levels in PD-1$^{-/-}$ mice (FIGS. 2A-B), as significant increases in PPS3-specific IgG1, IgG2b, and IgG2c levels in immune wild type or PD-1$^{-/-}$ mice relative to day 0 values were not detected (data not shown). IgM responses were normal to moderately increased in PD-1$^{-/-}$ mice. Thus, PD-1-deficiency yields significantly higher PPS3-specific IgG responses to both purified PPS3 and PPS3 associated with live *S. pneumoniae*.

Ab responses against structurally unrelated PPS were next assessed. As shown in FIG. 2F, PD-1$^{-/-}$ and wild type mice generated similar IgM responses against PPS1, -6A, and -23F. Wild type mice produced increased IgG over d0 values in response to the zwitterionic PPS1, which behaves as both a TI-2 and TD Ag (Kalka-Moll et al. (2002)*J. Immunol.* 169:6149-6153), but did not produce appreciable IgG responses against PPS-6A and -23F relative to pre-immune levels. In comparison, PD-1$^{-/-}$ mice generated significantly higher IgG levels in response to each of these PPSs, with the exception of the high (1 µg) PPS1 dose (FIG. 2F). The lack of increased PPS1-specific IgG levels in PD-1$^{-/-}$ mice could be due to the opposing role PD-1 plays in promoting TD Ab responses (Good-Jacobson et al. (2010) *Nature Immunol.* 11:535-542). Therefore, the extent to which PD-1 regulates Ab responses to PPS3 conjugated to the CRM$_{197}$ protein (Prevnar-13 vaccine) was examined. As shown in FIG. 2E, PPS3-specific IgM responses to Prevnar-13 were similar, while IgG responses were slightly reduced in PD-1$^{-/-}$ mice relative to wild type mice. Thus, PD-1 plays a significant role in suppressing IgG responses to multiple clinically relevant native PPS. However, conversion of native PPS to a TD Ag abolishes PD-1-mediated suppression of PPS-specific IgG responses.

Because PD-1$^{-/-}$ mice may have pre-existing phenotypic alterations that could contribute to increased PPS-specific IgG responses, the effects of blocking PD-1 from interacting with its ligands in normal mice was assessed. PD-1 mAb blockade between d1 and d5 post-immunization significantly increased PPS3-specific IgG responses in wild type mice (FIGS. 2G-H). This effect was observed with both 0.1 µg (FIG. 2G) and 1 µg (FIG. 2H) PPS3 doses (the optimal dose range for inducing PPS3-specific Ab responses). PD-1 blockade increased mean IgG titers over control mice by 3.5-fold (FIG. 2H; p=0.008). PPS3-specific ASCs were significantly increased in both spleen (p=0.02) and bone marrow (p=0.03) of PPS3-immune mice that had received PD-1 mAb blockade (FIG. 2I). Thus, PD-1 inhibits PPS-specific Ab responses by suppressing the generation and/or maintenance of splenic and bone marrow ASC.

Figure 4:
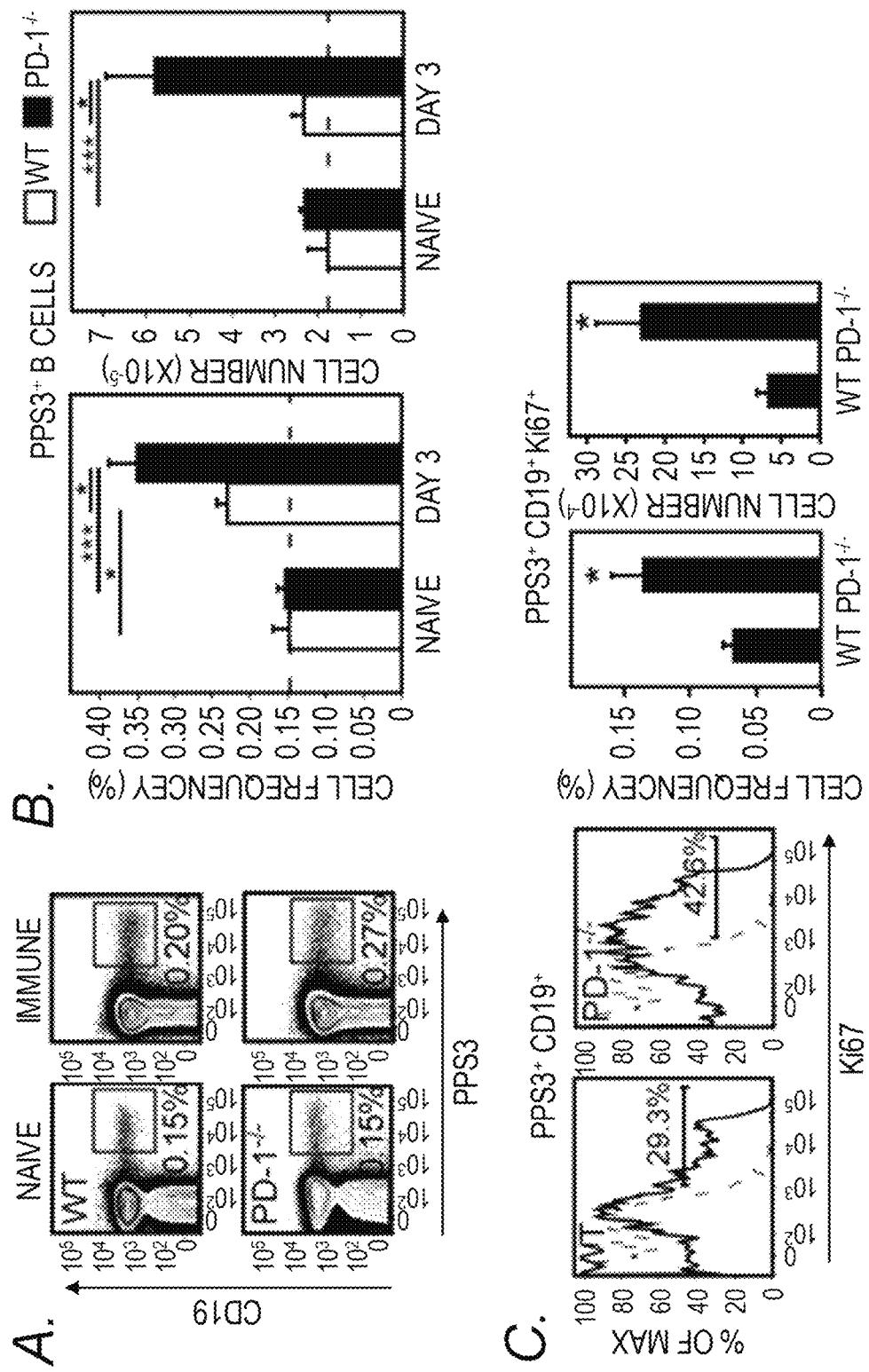
Figure 4:
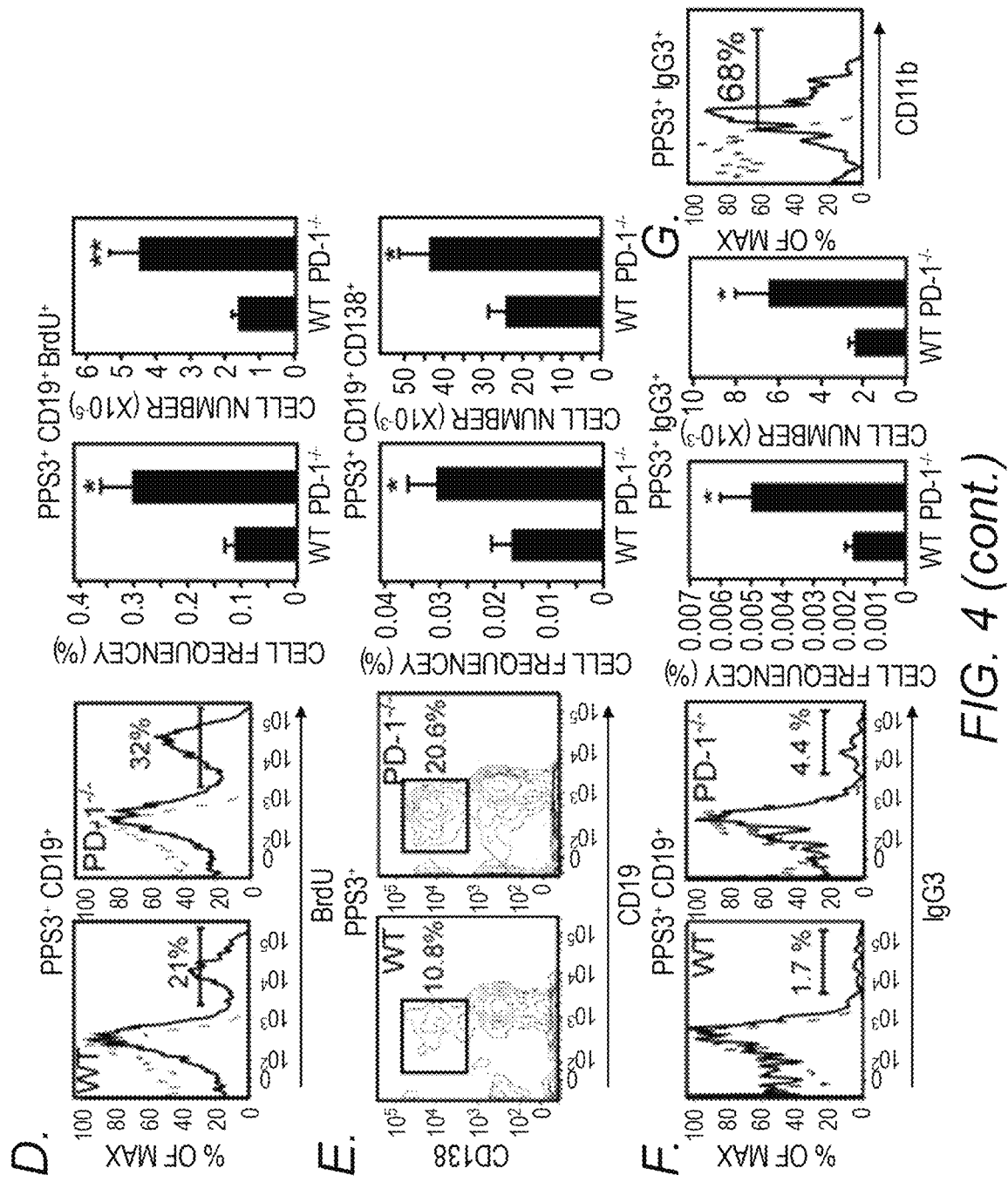
Figure 5:
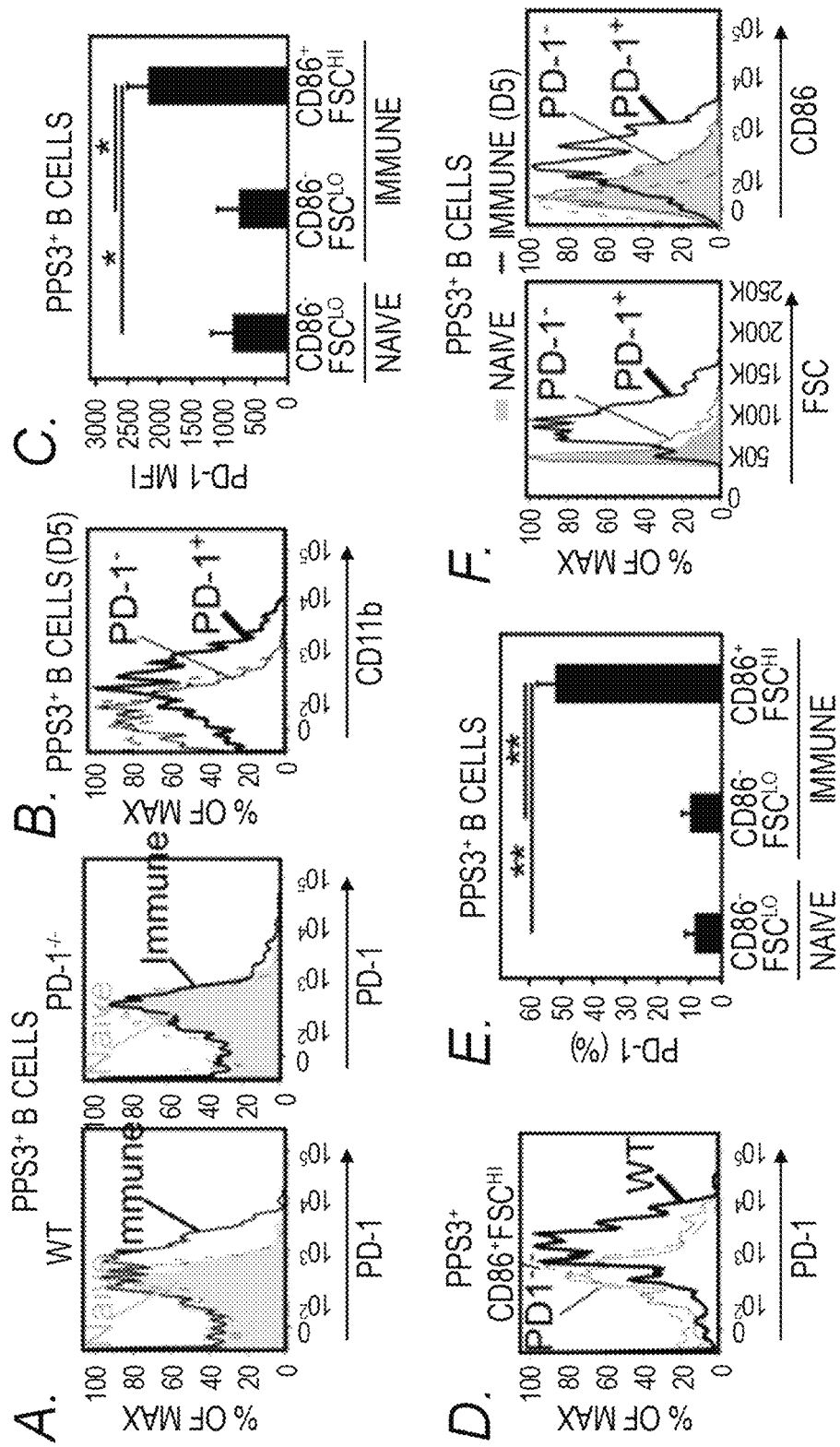
Figure 5:
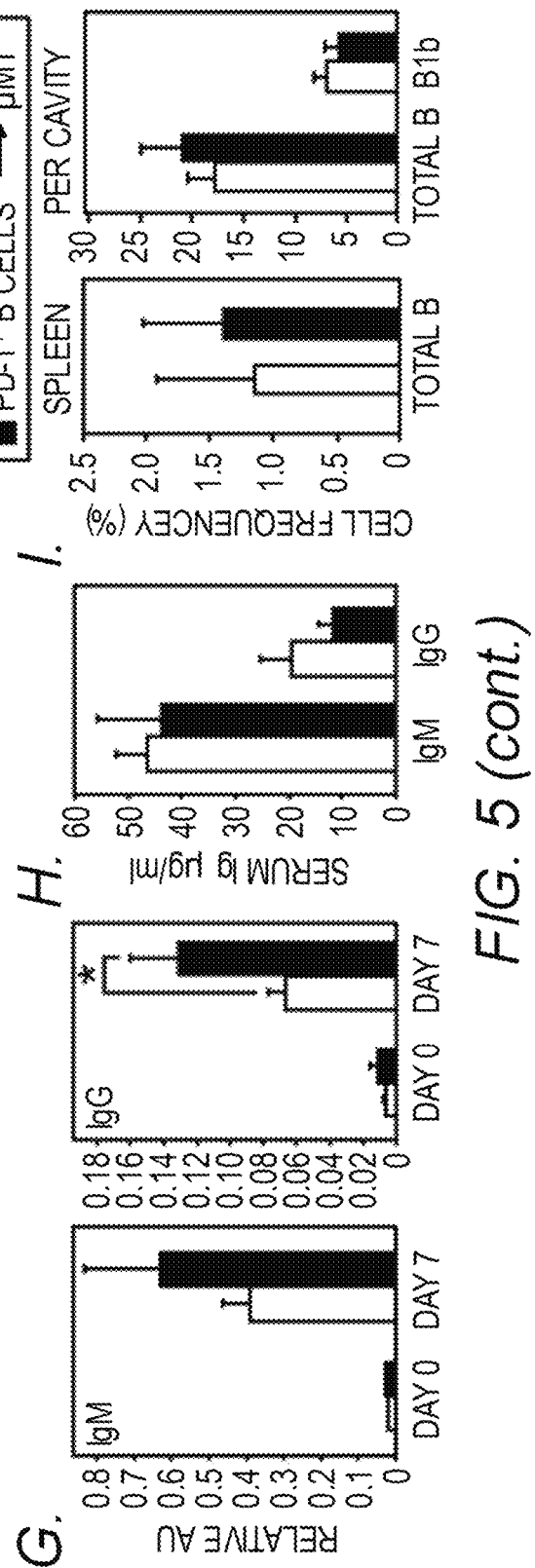

PD-1 Suppresses PPS3-Specific B Cell Proliferation, Isotype Switching, and Plasmablast Differentiation: Alterations in the numbers or frequencies of total B cells or B-1b cells in the spleens or peritoneal cavities of PD-1$^{-/-}$ mice compared to wild type mice were not found, although peritoneal B-2 cells were elevated (FIG. 3A). Moreover, PD-1$^{-/-}$ B cells proliferated normally in response to BCR stimulation in vitro (FIG. 3B). Therefore, the effects PD-1-deficiency had on PPS3-specific B cell responses using flow cytometry were examined, as previously described (Haas et al. (2014) *J. Infectious Diseases* 209:87-). PPS3-specific B cell frequencies and numbers were similar between naïve wild type and PD-1$^{-/-}$ mice (FIGS. 4A-B). Thus, increased Ab levels in PD-1$^{-/-}$ mice were not explained by increased PPS3-specific B cell precursor frequencies. Three days post immunization, a small (1.5-fold) increase in PPS3-specific B cell frequencies occurred in wild type mice (FIG. 4A) as previously reported (Haas et al. (2014) *J. Infectious Diseases* 209:87-97). However, PPS3-specific B cell frequencies and numbers were increased 2 to 2.5-fold in PD-1$^{-/-}$ mice (FIGS. 4A-B; p=0.038 and p=0.017, respectively). PPS3-specific Ki-67$^+$ B cell frequencies and numbers in PD-1$^{-/-}$ mice were also significantly higher (~2-fold) than in wild type mice at this time point (FIG. 4C; p=0.02 and p=0.02, respectively). In contrast, differences in the frequencies of non-Ag-specific B cells that were Ki-67$^+$ (wild type, 6.7±0.5% vs. PD-1$^{-/-}$, 6.4±0.1%) were not detected. Consistent with these findings, the frequencies and number of PPS3-specific BrdU$^+$ B cells following a 5-day pulse beginning at the time of PPS3 immunization were significantly higher (>2-fold) in PD-1$^{-/-}$ mice than wild type mice (FIG. 4D; p=0.02 and p=0.01, respectively). These differences were selective for Ag-specific cells, as non-Ag-specific BrdU$^+$ B cell frequencies were similar between wild type and PD-1$^{-/-}$ mice (wild type: 18.4±2.3% vs. PD-1$^{-/-}$: 20.2±2.4%). Thus, in the absence of PD-1, PPS3-specific B cell clonal expansion was increased following immunization.

PD-1$^{-/-}$ mice exhibited significantly increased frequencies and numbers of CD138$^+$CD19$^+$ PPS3$^+$ splenic plasmablasts 5 days post immunization relative to wild type mice (FIG. 4E; p=0.048 and p=0.035, respectively). Moreover, the frequency and number of IgG3$^+$ class-switched PPS3-specific B cells was significantly higher (~2.5-fold) in PD-1$^{-/-}$ mice compared to wild type mice at this time point (FIG. 4F; p=0.048). Notably, a major fraction of PPS3-specific IgG3$^+$ B cells in PD-1$^{-/-}$ mice expressed CD11b (FIG. 4G), suggesting that PD-1-deficiency may affect IgG3 switching in the B-1b cell population known to participate in PPS3-specific Ab responses (Haas et al. (2014) *J. Infect. Dis.* 209:87-97; Haas et al. (2005) *Immunity* 23:7-18). Thus, in the absence of PD-1, PPS3-specific B cell division and the frequency of class-switched IgG3$^+$ cells were increased.

B Cell-Specific PD-1 Expression Suppressed PPS-Specific Ab Responses: To assess the potential mechanism by which PD-1 suppresses PPS-specific B cell expansion and IgG production, it was first examined whether PD-1 was expressed by PPS3-specific B cells. Naïve PPS3-specific B cells lacked PD-1 expression. However, a fraction (~25%) of PPS3-specific B cells expressed PD-1 following immunization (FIG. 5A). Frequencies of PD-1$^+$ PPS3-non-binding cells were not altered by immunization (not shown). As expected, B cells from immune PD-1$^{-/-}$ mice remained negative. A fraction of PPS3-specific CD11b$^+$ (B-1) B cells expressed PD-1 (FIG. 5B), although not all PD-1-expressing B cells were CD11b$^+$. Activated (FSC$^{hi}$CD86$^+$) PPS3-specific B cells exhibited a 3-fold increase in PD-1 expression (MFI) levels relative to non-activated (FSC$^{lo}$TD86$^-$) PPS3-specific B cells in both immune (p=0.02) and nave mice (p=0.02; FIG. 5C). Approximately 50% of activated PPS3-specific B cells expressed PD-1 at levels over background staining (isotype control and PD-1$^{-/-}$ activated B cell staining; FIG. 5D) whereas PD-1 expression by non-activated PPS3-specific B cells was similar between immune and naïve mice (FIGS. 5D-E). Consistent with this, PD-1$^+$ PPS3$^+$ B cells exhibited increased size (FSC) and CD86 expression (FIG. 5F), whereas PD-1$^{neg}$ PPS3$^+$ B cells from immune mice closely resembled PPS3$^+$ B cells from naïve mice. These data support that PD-1 expression is induced on activated PPS3-specific B cells in immune mice.

Selective up-regulation of PD-1 on Ag-specific B cells suggests a potential mechanism whereby B cell-intrinsic PD-1 expression could regulate PPS-specific B cell responses. To assess this, 4×10$^7$ wild type or PD-1$^{-/-}$ spleen B cells were adoptively transferred into B cell deficient (nMT) mice, since high numbers (1×10$^7$) of splenic B cells reconstitute B-1b cells and PPS-specific Ab responses (Haas (2005) *Immunity* 23:7-18. Recipients were immunized with PPV23 two days post transfer. Mice reconstituted with PD-1$^{-/-}$ B cells produced significantly higher PPV23-specific IgG levels relative to recipients of wild type B cells (FIG. 5G). PPV23-specific IgM responses were not significantly different (FIG. 5G). Notably, total (non-specific) reconstituted serum IgM and IgG levels at this time point were not significantly different between recipient groups (FIG. 5H), demonstrating that there was a selective increase in PPV23-specific IgG responses in PD-1$^{-/-}$ B cell-recipient mice. Finally, splenic B cell and peritoneal total B cell and B-1b cell recovery were similar between recipient groups (FIG. 5I), indicating that differential B cell reconstitution was unlikely to have caused the increased PPS-specific IgG responses observed in PD-1$^{-/-}$ B cell recipient mice. Thus, B cell-expressed PD-1 plays a key role in suppressing PPS-specific IgG responses.

Figure 6:
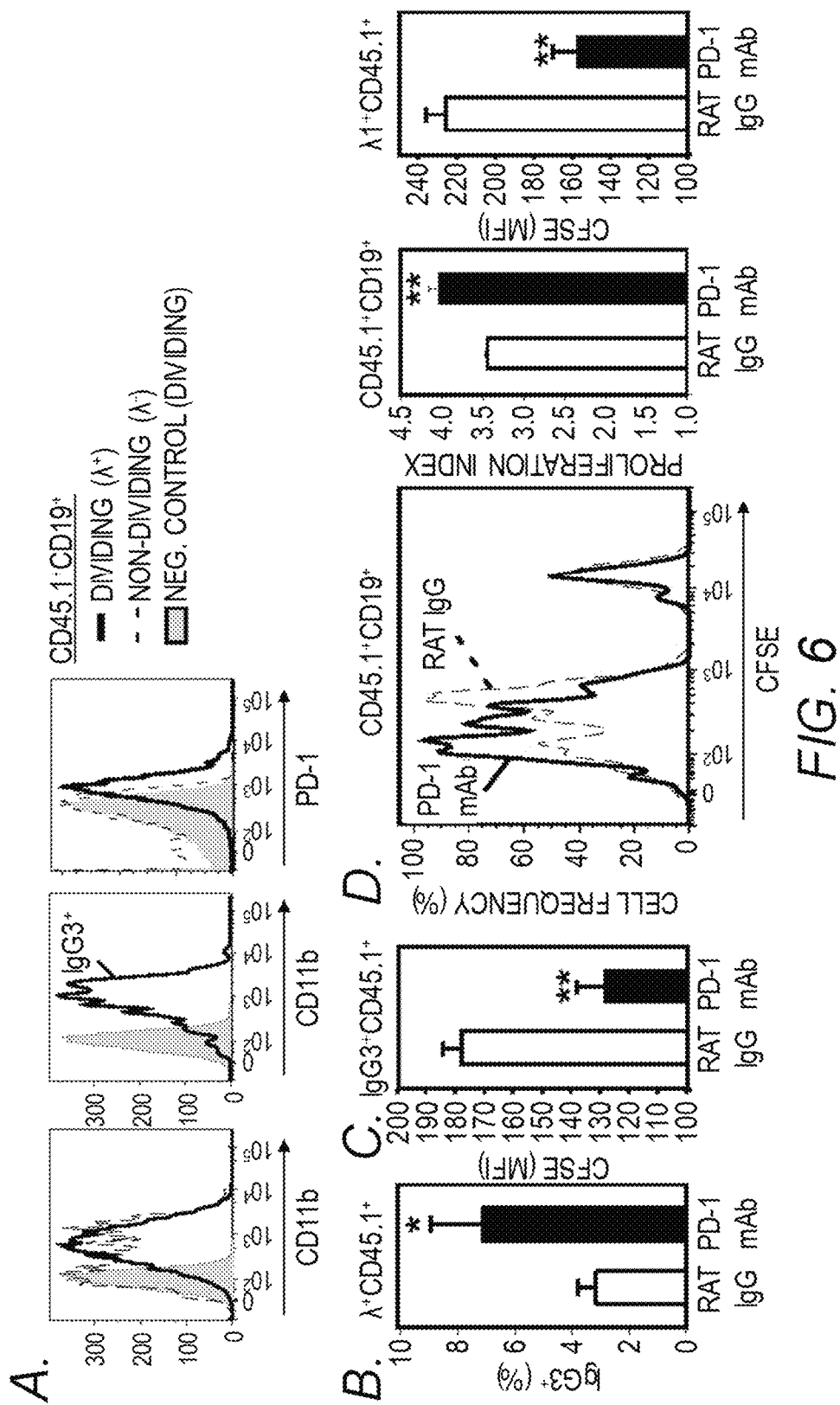

Unfortunately, detection of wild type PPS-specific B cells in reconstituted mice is not a feasible strategy to assess the effects of B cell-intrinsic PD-1 expression on Ag-specific B cell proliferation during in vivo responses. To assess this, CFSE-labeled allotype-marked (CD45.1$^+$) peritoneal B-1b cells from B1-8$^{high}$ IgH knock-in mice were adoptively transferred into the peritoneal cavities of CD45.2$^+$ PD-1$^{-/-}$ mice. The recipient mice were immunized with NP$_{40}$-Ficoll and treated with either a PD-1 blocking mAb (RMP1-14) or an isotype control mAb. Nearly all NP-specific (λ$^+$CD45.1$^+$) CD19$^+$ B cells isolated from the peritoneal cavities of both groups of mice had undergone extensive division by 3 days post-immunization and expressed CD11b and PD-1 (FIG. 6A). In contrast, non-specific (2) CD45.1$^+$ B cells were non-dividing, CD11b$^{+/-}$, and lacked PD-1 expression. Interestingly, NP-specific peritoneal B-1b cells in mice treated with the PD-1 blocking mAb showed significantly increased (~2.5-fold) frequencies of IgG3$^+$ cells (FIG. 6B) and these IgG3$^+$ cells had lost significantly more CFSE than those in mice receiving control mAb (FIG. 6C). Although differences in IgG3$^+$ frequencies were not observed in transgenic B cells recovered from spleens, significantly increased division was observed in spleens from PD-1$^{-/-}$ mice treated with the PD-1 mAb relative to control mAb (FIG. 6D). Thus, B cell-intrinsic PD-1 expression suppresses NP-specific B cell proliferation and the generation and/or proliferation of IgG$^+$ class-switched B-1b cells during in vivo responses to NP-Ficoll.

Figure 7:
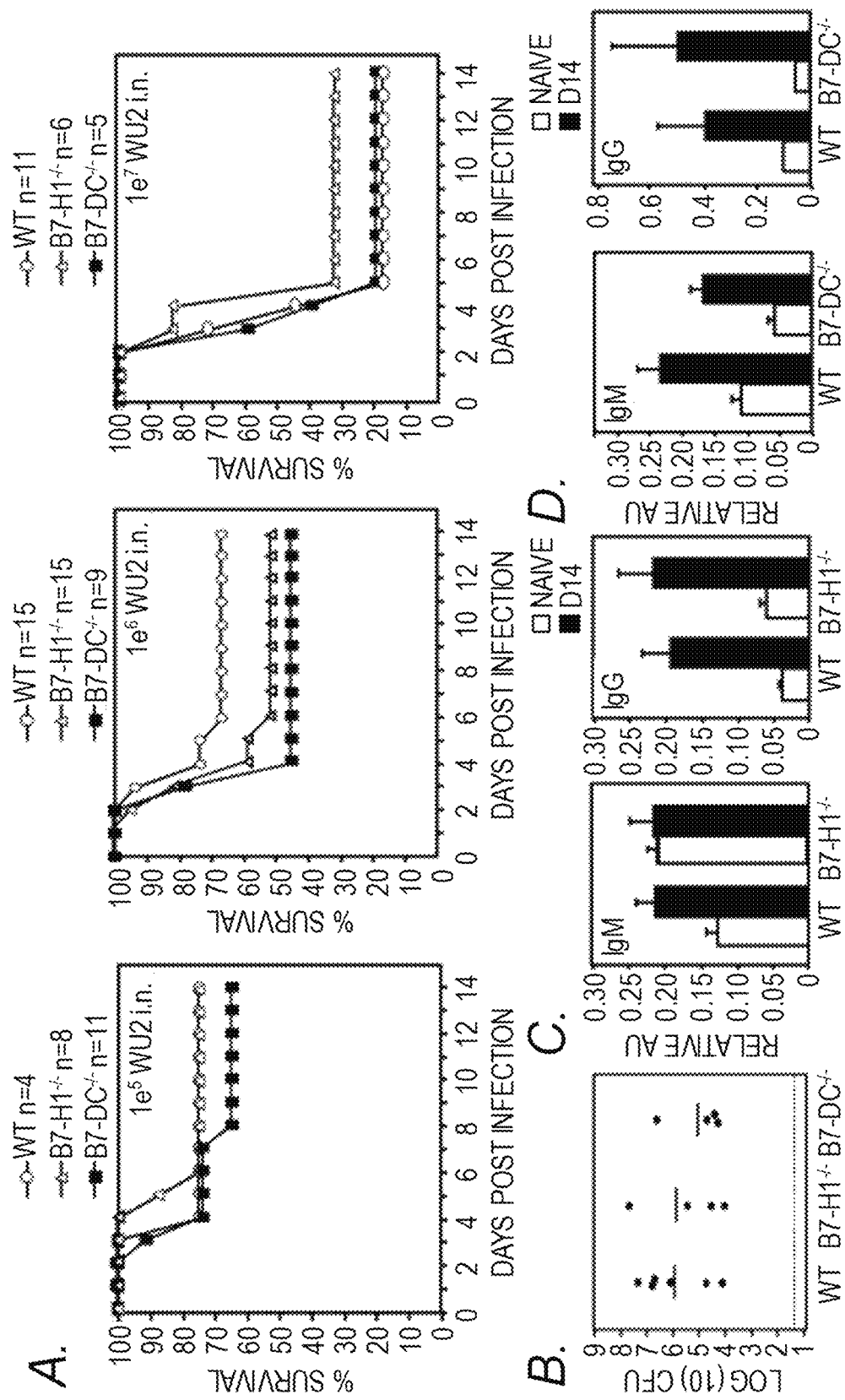
Figure 8:
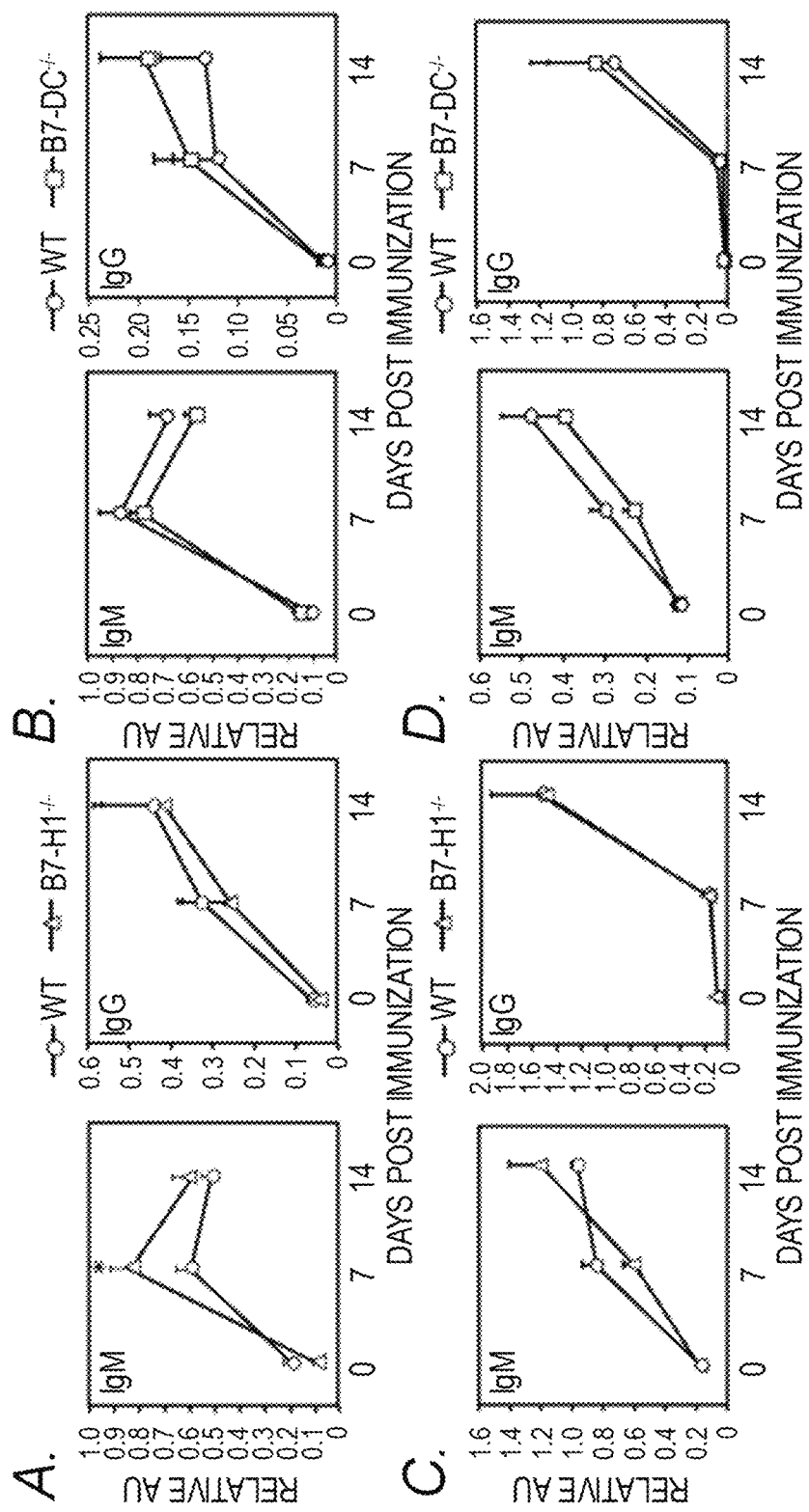
Figure 8:
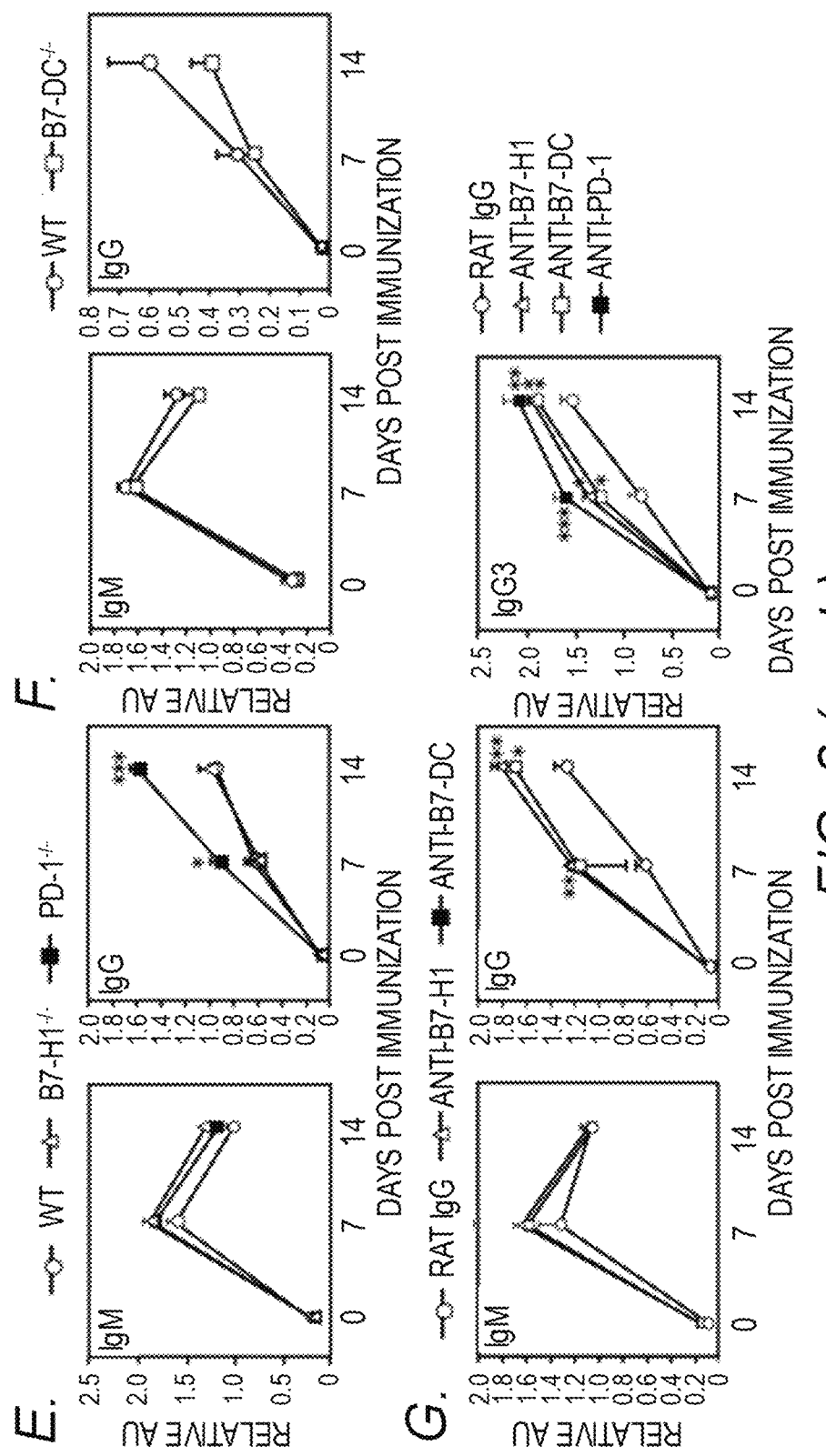
Figure 8:
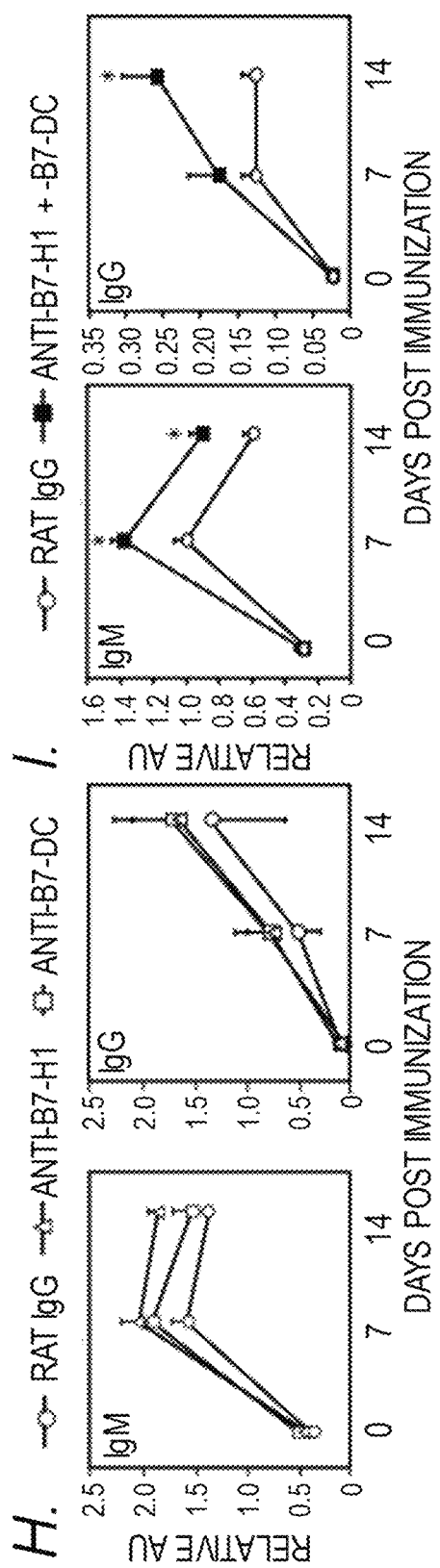

PD-1 Suppressed IgG Responses to PPS and Other TI-2 Ags Through Combined Interactions with B7-H1 and B7-DC: B7-H1 and B7-DC have been shown to have overlapping or distinct functions, depending on the model system under study (Keir et al. (2008) *Ann. Rev. Immunol.* 26:677-704). The role of PD-1 ligands, B7-H1 and B7-DC, in PD-1-mediated regulation of protective Ab responses to *S. pneumoniae* was assessed. As observed with PD-1$^{-/-}$ mice (FIGS. 1A-B), B7-H1$^{-/-}$ and B7-DC$^{-/-}$ mice exhibited similar susceptibilities and lung bacteria burdens following virulent *S. pneumoniae* respiratory infection compared to wild type mice (FIGS. 7A-B). However, in contrast to PD-1$^{-/-}$ mice which showed significantly increased PPS3-specific IgG relative to wild type mice following pneumococcal respiratory infection (FIGS. 1E-G), B7-H1$^{-/-}$ and B7-DC$^{-/-}$ mice produced IgG levels that were similar to wild type mice (FIGS. 7C-D). In addition, PPS3-specific IgG levels following PPV23 immunization were not significantly different between B7-H1$^{-/-}$ or B7-DC$^{-/-}$ mice and wild type mice (FIGS. 8A-B). B7-H1$^{-/-}$ and B7-DC$^{-/-}$ mice also produced normal Ab responses to the PPS3-conjugate vaccine (FIGS. 8C-D). Thus, in contrast to results with PD-1$^{-/-}$ mice, B7-H1$^{-/-}$ and B7-DC$^{-/-}$ mice do not exhibit altered PPS-specific humoral responses to S. pneumoniae infection or PPS immunization.

PD-1$^{-/-}$ mice also generated significantly higher IgG responses to the synthetic TI-2 Ag, TNP-Ficoll (FIG. 8E), as reported for responses to DNP-Ficoll (Nishimura et al. (1998) Int. Immunol. 10:1563-1572). PD-1$^{-/-}$ mice produced significantly higher levels of TNP-specific IgG1, IgG2b, IgG2c, IgG3, and IgA (data not shown). In contrast, TNP-specific IgM and IgG responses to TNP-Ficoll were unaltered by B7-H1 or B7-DC deficiency (FIGS. 8E-F), with the exception of IgG2c, which was selectively increased in B7-H1$^{-/-}$ mice (data not shown). Levels of TNP-specific IgG3, which is the predominant IgG isotype produced in response to this and other TI-2 Ags, were also normal in B7-H1$^{-/-}$ or B7-DC$^{-/-}$ mice. Thus, individual B7-H1 or B7-DC deficiency had little effect on total IgM or IgG responses to PPS (FIGS. 8A-F (PPS3); PPS-1, -6A, and -23F; data not shown) or a synthetic TI-2 Ag, TNP-Ficoll.

Given the possibility that B7-H1$^{-/-}$ and/or B7-DC$^{-/-}$ mice have other defects that negatively affect TI-2 Ab responses, the effects of B7-H1 and B7-DC mAb blockade in wild type mice were examined. B7-H1 and B7-DC blockade each significantly increased IgG, but not IgM responses, to TNP-Ficoll relative to rat IgG control-treated mice (FIG. 8G). Consistent with this, B7-H1 and B7-DC mAb blockade each significantly increased TNP-specific IgG3 (FIG. 8G). However, PD-1 blockade produced the greatest increase in TNP-specific IgG3 levels. IgG2b, IgG2c, and IgG1 (but not IgA) TNP-specific levels were also increased in mice receiving B7-H1 and B7-DC mAb blockade (data not shown). Thus, B7-H1 and B7-DC mAb blockade in wild type mice, in contrast to B7-H1 and B7-DC deficiency, significantly increased IgG responses to TNP-Ficoll. However, PD-1 mAb blockade produced greater increases than single blockade alone, suggesting potential overlapping functions for B7-H1 and B7-DC in carrying out PD-1-mediated suppression of IgG responses.

Figure 2:
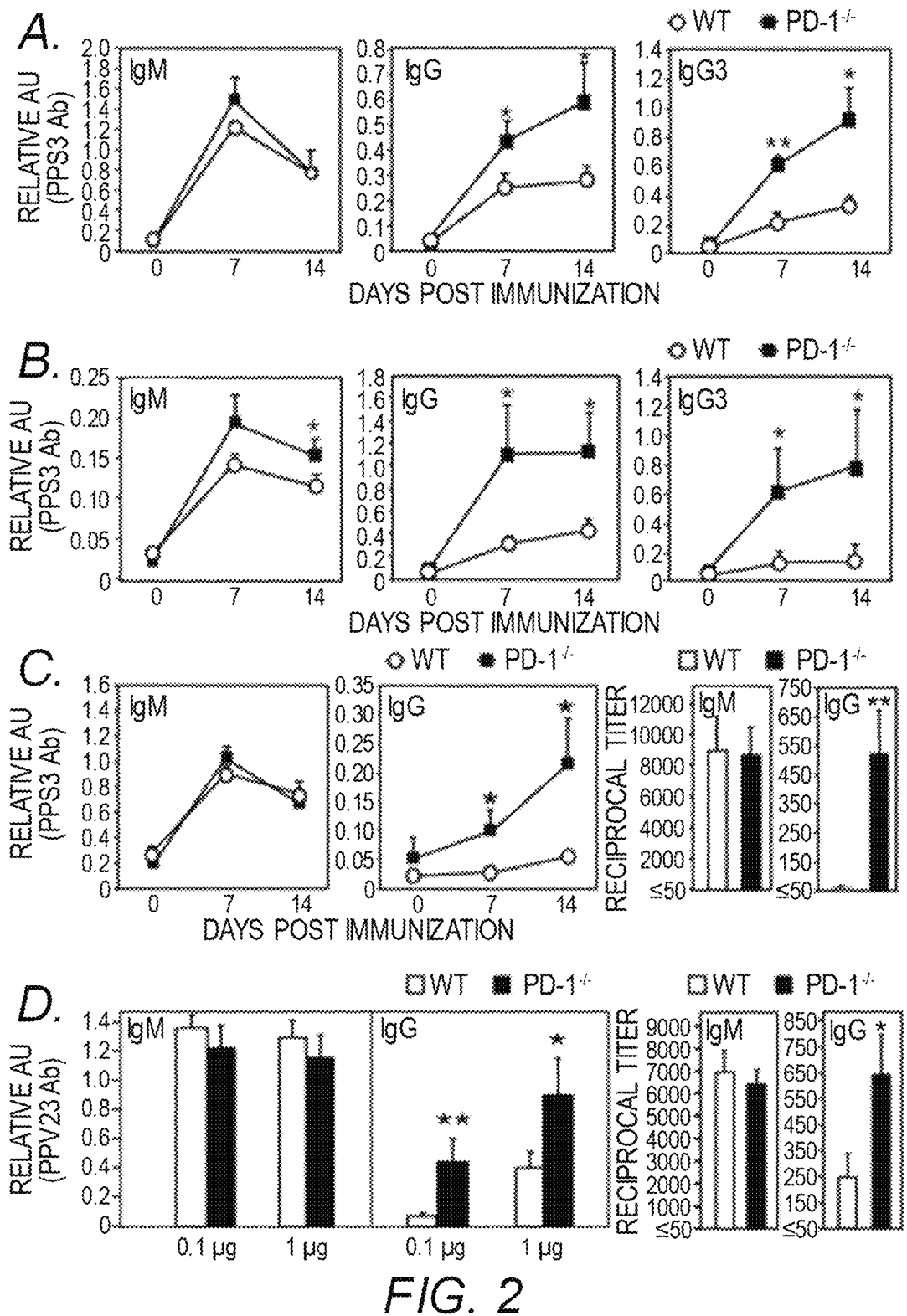
Figure 2:
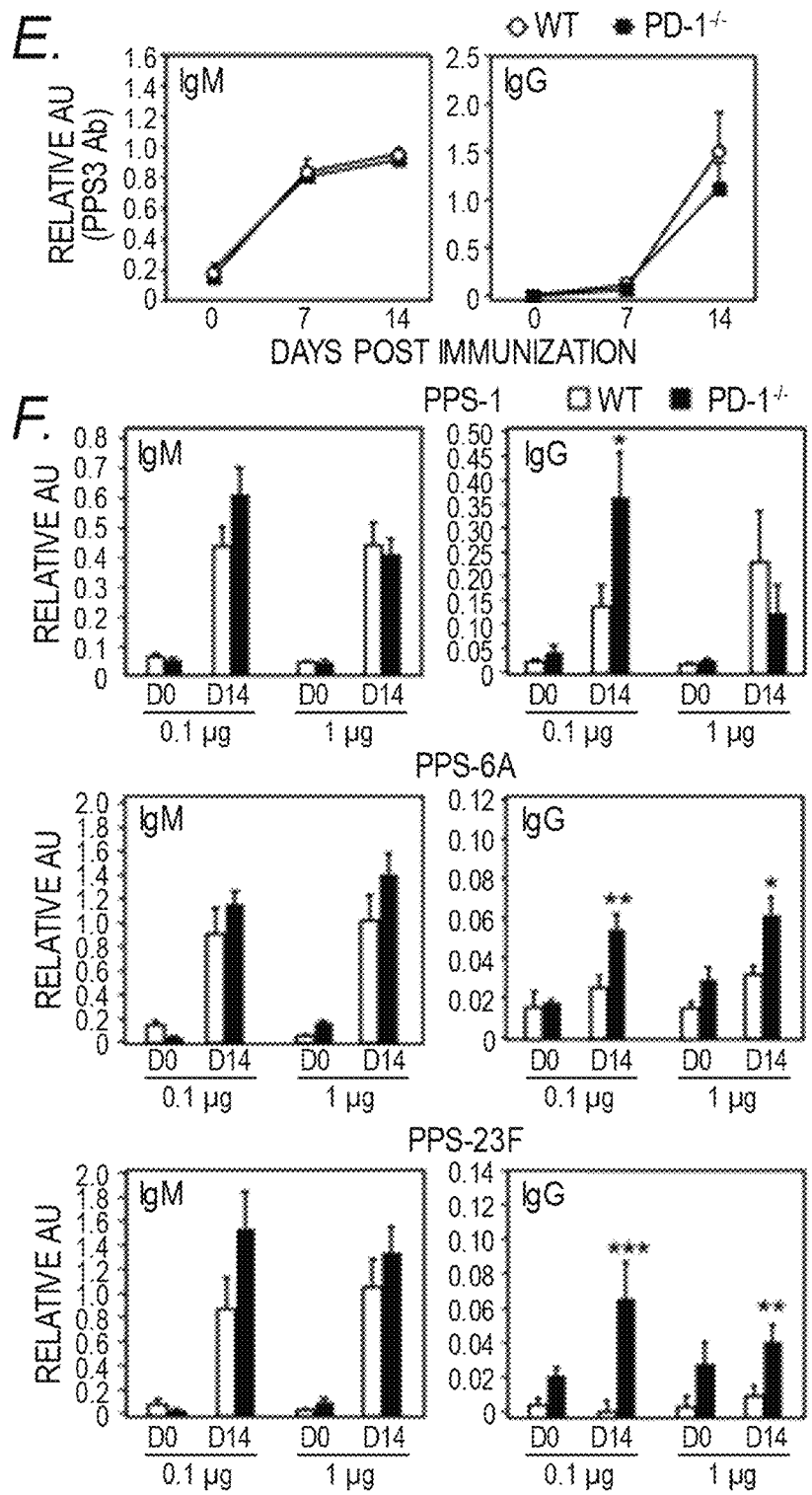
Figure 2:
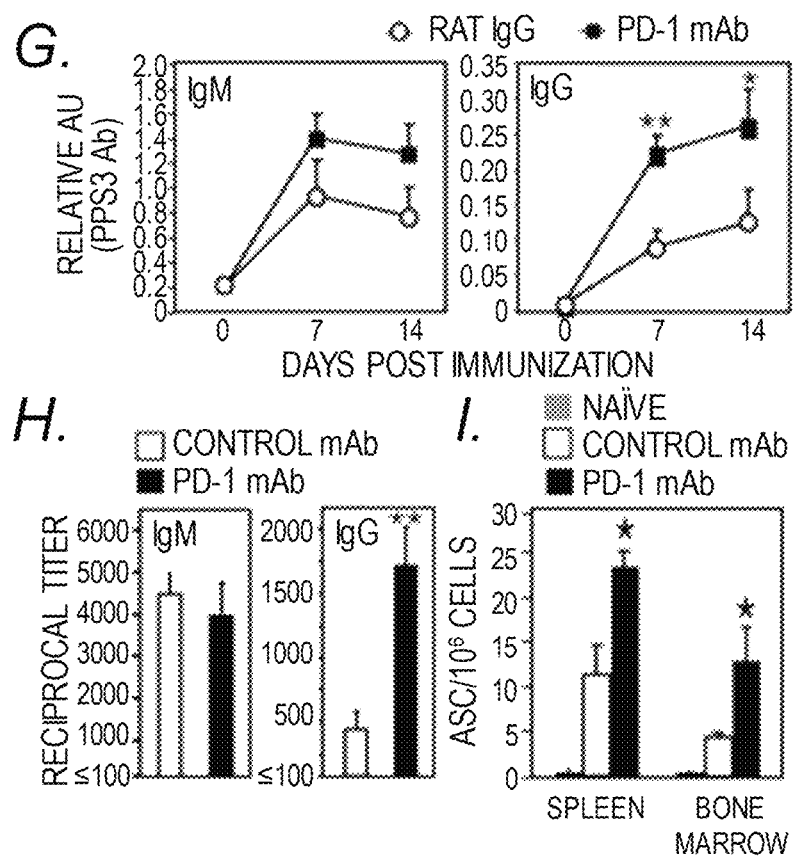

Single B7-H1 or B7-DC mAb blockade moderately increased PPS3-specific IgG responses relative control mice (FIG. 8H), although B7-H1, but not B7-DC, blockade significantly increased PPS3-specific IgM levels, similar to what was observed in B7-H1$^{-/-}$ mice (FIG. 8A). To test the combined roles of B7-H1 and B7-DC in PD-1-mediated suppression of PPS Ab responses, B7-H1 and B7-DC blocking mAbs were co-administered to wild type mice following PPV23 immunization. As shown in FIG. 8I, dual blockade significantly increased PPS3-specific IgM and IgG levels (p=0.036) comparable to what was observed with PD-1 mAb blockade and PD-1 deficiency (FIG. 2). Collectively, these results demonstrate B7-H1 and B7-DC have overlapping functions in carrying out PD-1-mediated suppression of PPS Ab responses.

Figure 9:
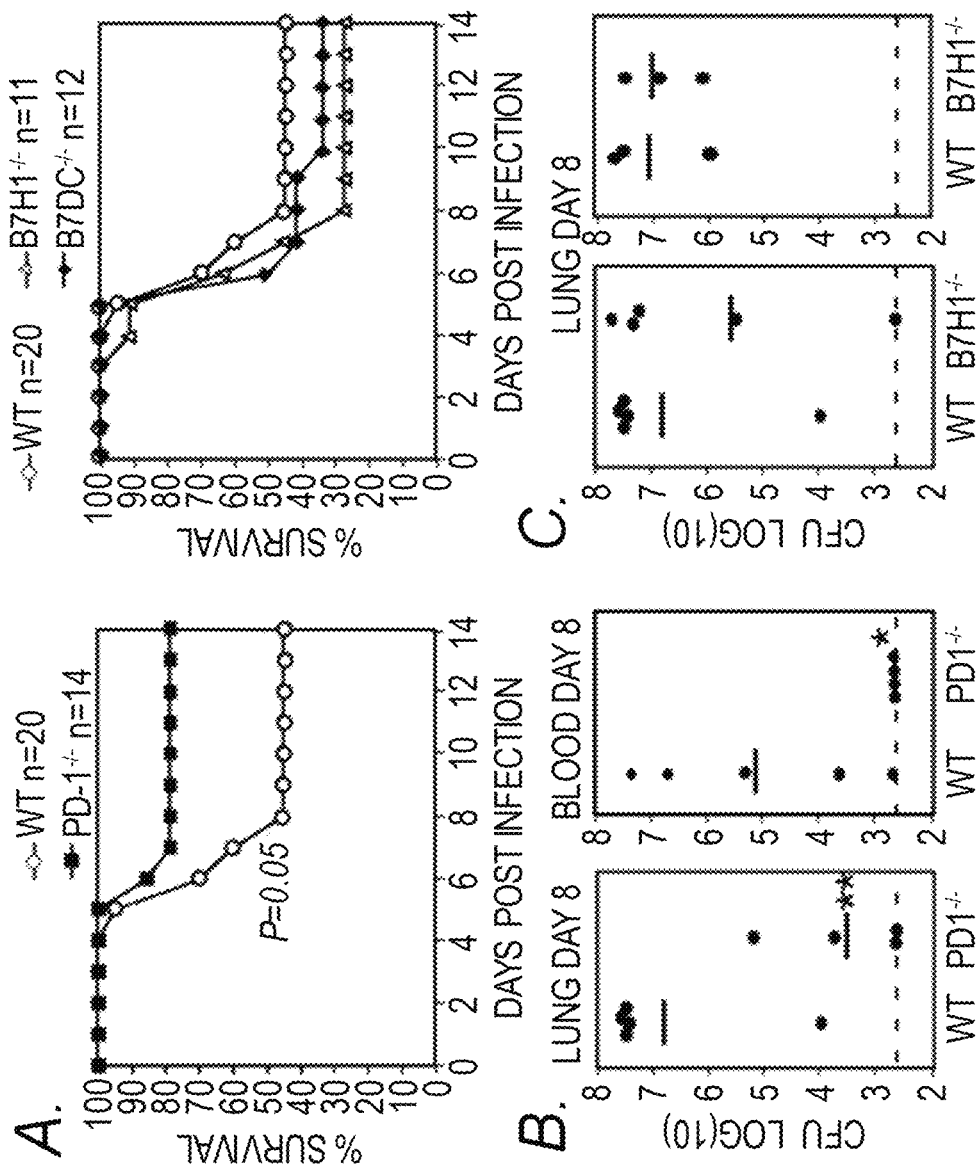
Figure 9:
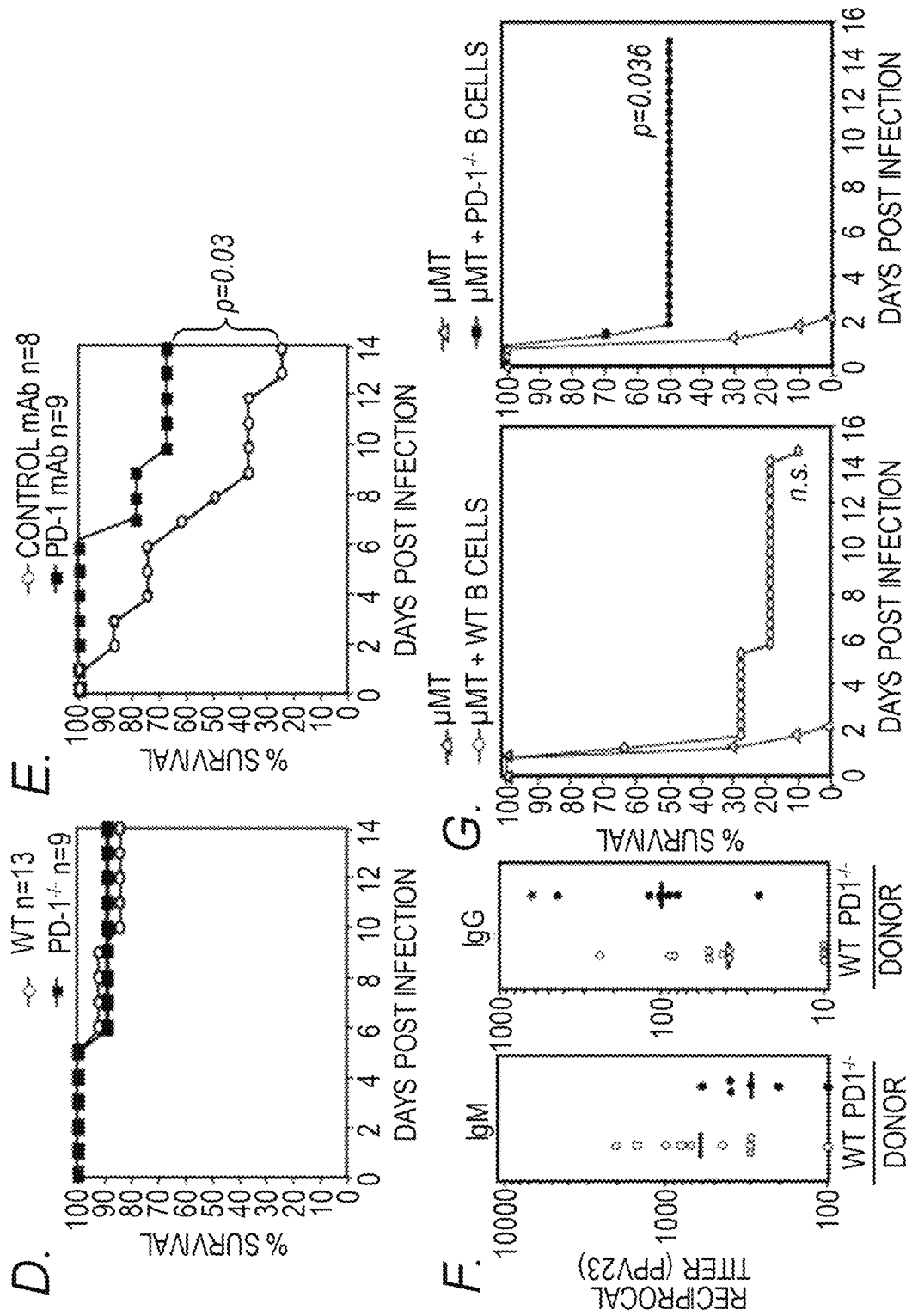

PD-1 Deficiency and mAb Blockade in Wild Type Mice Suppresses Protective Humoral Immune Responses to S. pneumoniae: Based on studies in mice, IgG Abs raised against the S. pneumoniae capsule and cell wall constituents provide superior protection relative to IgM Abs (Briles et al. (1981) J. Exp. Med. 153:694-705). Therefore, the physiological relevance of PD-1-mediated suppression of capsule-specific IgG responses was examined by challenging immune wild type and PD-1$^{-/-}$ mice with a lethal i.n. dose (1×10$^7$ CFU) of WU2 28 days following immunization. PPV23-immunized wild type mice were offered moderate protection (~40% survival) whereas immune PD-1$^{-/-}$ mice had significantly increased survival (~80%; FIG. 9A). Consistent with these results, PD-1$^{-/-}$ mice had significantly lower bacterial counts in the lung and blood (bacteremia) (FIG. 9B, p=0.01 and p=0.04, respectively). In contrast, survival and bacterial counts in immune B7-H1$^{-/-}$ and B7-DC$^{-/-}$ mice were similar to wild type mice (FIG. 9A, C). Thus, despite the similar sensitivities of naïve PD-1$^{-/-}$, B7-H1$^{-/-}$, B7-DC$^{-/-}$, and wild type mice to this infection (FIGS. 1A-C, 7A-B), immunization provided a selective advantage to PD-1$^{-/-}$ mice, likely owing to increased PPS3-specific IgG in these mice. No differences in survival were observed between wild type and PD-1$^{-/-}$ mice that had been immunized with Prevnar-13 (FIG. 9D), which elicits normal PPS Ab responses in these mice (FIG. 2E). Finally, wild type mice receiving transient PD-1 mAb blockade following PPV23 immunization demonstrated significantly increased survival relative to control mAb-treated mice following respiratory challenge (FIG. 9E, p=0.03). Thus, PD-1-mediated suppression of PPS-specific humoral immunity impairs vaccine-mediated protection against lethal pneumococcal respiratory infections.

B Cell-Intrinsic PD-1 Expression Regulates Protection Against S. pneumoniae Infection: To assess whether PD-1 expression on B cells directly regulates protection against S. pneumoniae infection, wild type or PD-1$^{-/-}$ B cells were transferred into B cell-deficient mice. Recipients were then immunized and challenged with a lethal S. pneumoniae infection. As observed in earlier experiments (FIG. 5G), μMT mice reconstituted with PD-1$^{-/-}$ B cells produced significantly higher IgG (~2.5-fold higher titers on d7), but not IgM levels in response to PPV23 (FIG. 9F; p=0.04). Importantly, PPV23-immunized μMT mice reconstituted with PD-1$^{-/-}$ B cells were offered significant protection against systemic S. pneumoniae infection (50% survival) relative to non-reconstituted mice (0% survival; FIG. 9G). In contrast, overall survival in μMT mice reconstituted with wild type B cells did not significantly differ from non-reconstituted μMT mice (9% versus 0%; FIG. 9G). Thus, B cells from PD-1$^{-/-}$, but not wild type, mice afforded B cell-deficient mice with significant protection against systemic pneumococcal infection.

Discussion

Herein, it is shown that the PD-1:PD-L regulatory axis suppresses protection against respiratory and invasive S. pneumoniae infections by regulating the protective adaptive humoral immune response to one of the most potent virulence factors of S. pneumoniae the capsular polysaccharide (Moxon and Kroll (1990) Curr. Top. Microbiol. Immunol. 150:65-85). For the first time, the current study provides definitive evidence that PD-1 expression on B cells has profound physiological consequences for the regulation of immunity to infection. Specifically, the current data demonstrates that PD-1 suppresses B cell clonal expansion and IgG production in response to native and bacterial-associated PPS, but not protein-conjugated PPS, revealing a unique role for the PD-1:PD-L axis in selectively suppressing TI responses to pathogens. The data further indicate that B7-H1 and B7-DC both contribute to PD-1-mediated suppression. Finally, the results showing that PD-1 blockade following PPS immunization significantly increases protection against lethal S. pneumoniae infection has important implications for future strategies aimed at enhancing protection against life-threatening encapsulated bacterial infections.

Interestingly, PD-1 or PD-L deficiency had little effect on lung bacterial burdens or survival following an acute respiratory or systemic infection with a highly invasive S. pneumoniae serotype 3 strain (Briles et al. (1992) Infect. Immun. 60:111-116; Haas et al. (2014) J. Infectious Diseases 209:

87-97)—a serotype associated with one of the highest fatality rates in humans (Garau and Calbo (2007) *Clin. Infect. Dis.* 45:52-54; Weinberger et al. (2010) *Clin. Infect. Dis.* 51: 692-699). In contrast to the current results, naïve PD-1$^{-/-}$ mice are more resistant to peritoneal polymicrobial sepsis (Huang et al. (2009) *Proc. Nat. Acad. Sci. U.S.A.* 106: 6303-6308) and *Listeria monocytogenes* challenge (Yao et al. (2009) *Blood* 113:5811-5818) due to the role PD-1 plays in suppressing innate cells, yet are more susceptible to *Mycobacteria tuberculosis* respiratory infection due its role in controlling excessive inflammatory responses which may be largely promoted by CD4$^+$ T cells (Barber et al. (2011) *J. Immunol.* 186:1598-1607; Lazar-Molnar et al. (2010) *Proc. Nat. Acad. Sci. U.S.A.* 107:13402-13407). The lack of effect PD-1 and PD-L deficiency have on primary pneumococcal respiratory challenge in the current study may reflect dual roles for the PD-1:PD-L pathway in suppressing innate cell clearance mechanisms while limiting inflammation or alternatively, a limited role for the PD-1:PD-L pathway in regulating innate responses to a rapidly progressing lethal pneumococcal infection.

Nonetheless, PD-1 suppressed the generation of a protective humoral response during acute respiratory pneumococcal infection. Although Ab responses were generated too slowly to impact the outcome of primary infection with highly virulent pneumococci, this suppression was physiologically relevant since 1) sera from *S. pneumoniae*-infected PD-1$^{-/-}$ mice was superior in reducing bacteremia and delaying time to death in *S. pneumoniae*-challenged µEMT mice compared to sera from wild type mice and 2) PD-1$^{-/-}$ mice that survived a low lethal dose respiratory infection were offered significant protection against subsequent lethal systemic pneumococcal infection, in contrast to wild type mice. These findings are likely explained by the significantly increased levels of capsule-specific serum IgG in PD-1$^{-/-}$ mice, which enable optimal clearance of heavily-encapsulated bacteria by promoting FcγR-mediated uptake, complement activation, and phagocyte activation and survival (Tian et al. (2009) *Infect. Immun.* 77:1502-1513; Weber et al. (2012) *Infect. Immun.* 80:1314-1322). Indeed, multiple studies in mice have demonstrated the importance of IgG in eliciting protection against pneumococcus (Briles et al. (1981) *Nature* 294:88-90; Haas et al. (2002) *Immunity* 17:713-723; Haas et al. (2009) *J. Immunol.* 183:3661-3671; McLay et al. (2002) *J. Immunol.* 168:3437-3443; Tian et al. (2009) *Infect. Immun.* 77:1502-1513; Weber et al. (2012) *Infect. Immun.* 80:1314-1322). Importantly, PD-1 deficiency and transient PD-1 mAb blockade in wild type mice following immunization both yielded significantly increased PPS-specific IgG levels and protection against lethal *S. pneumoniae* challenge. Adoptive transfer experiments revealed that these effects were dependent on B cell-expressed PD-1. Thus, the PD-1:PD-L pathway plays a central role in suppressing highly protective IgG responses against the pneumococcal capsule, and may similarly regulate immunity to other polysaccharide-bearing pathogens.

It is believed that the current study provides the first definitive evidence of a physiological role for PD-1 expression on B cells in vivo. Other studies have shown PD-1-mediated effects on B cell responses in vivo (Haas (2011) *J. Immunol.* 187:5183-5195; Good-Jacobson et al. (2010) *Nature Immunol.* 11:535-542; Titanji et al. (2010) *J. Clin. Invest.* 120:3878-3890; Kawamoto et al. (2012) *Science* 336:485-489). However, to date only T cell-intrinsic PD-1 signaling has been shown to regulate B cell responses (Good-Jacobson et al. (2010) *Nature Immunol.* 11:535-542; Kawamoto et al. (2012) *Science* 336:485-489). PPS3 induced PD-1 expression on PPS3-specific B cells, some of which belonged to the B-1b cell subset, similar to that observed for hapten-specific B-1b cells from mice and non-human primates following immunization with NP- or TNP-Ficoll (Yammani and Haas (2013) *J. Immunol.* 190: 3100-3108). Indeed, PD-1 may be a global suppressor of T cell independent responses, as PD-1 also suppresses Ab responses to haptenated Ficoll (Nishimura et al. (1998) *Int. Immunol.* 10:1563-1572; Haas (2011) *J. Immunol.* 187:5183-5195), a T cell independent antigen that differs from PPS3 in several key respects (in contrast to PPS3 and many other types of PPS, it lacks co-associated bacterial contaminants that influence humoral responses (Sen et al. (2005) *J. Immunol.* 175:3084-3091), lacks charge, lacks tolerogenic potential, can be adjuvanted by TLR agonists (Kovarik et al. (2001) *Immunology* 102:67-76), and localizes to different accessory cells (Humphrey (1981) *Eur. J. Immunol.* 11:212-220; Harms et al. (1996) *Infect. Immun.* 64:4220-4225).

Importantly, the current results indicate that PD-1 functions to significantly limit PPS3-specific B cell proliferation and the generation of IgG$^+$ cells. Since proliferation and isotype switching are tightly linked processes (Deenick et al. (1999) *J. Immunol.* 163:4707-4714; Rush et al. (2005) *Proc. Natl. Acad. Sci. U.S.A.* 102:13242-13247), it is not surprising that PD-1 had the most significant effects on PPS-specific IgG production. Notably, there was a trend for increased PPS3-specific IgA (albeit not significant) in PD-1$^{-/-}$ mice, and PD-1 deficiency and mAb blockade significantly increased IgA levels in response to TNP-Ficoll. Therefore, without wishing to be bound to any one particular theory, it is proposed that PD-1 primarily regulates isotype switching by suppressing the ability of Ag-specific B cells to divide, although it remains possible that PD-1 also influences the production of (or responsiveness to) switch factors. The current study did not detect splenomegaly or increased splenic or peritoneal total B cell or B-1b cell numbers in PD-1$^{-/-}$ mice, nor were altered BCR-induced in vitro proliferation in splenic B cells from PD-1$^{-/-}$ mice observed as originally reported by Nishimura et al. ((1998) *Int. Immunol.* 10:1563-1572). These discrepancies could be due to differences in the composition of gut flora between colonies, as other studies have elegantly demonstrated that altered flora can alter B cell function in PD-1$^{-/-}$ mice and that antibiotic therapy can normalize their activation phenotype (Kawamoto et al. (2012) *Science* 336:485-489; Maruya et al. (2013) *Gut Microbes* 4:165-171). Consistent with the above results, PD-1$^{-/-}$ and wild type spleen B cells reconstituted similar numbers of B-1b cells in B cell-deficient mice. Thus, the current findings are not explained by altered B-1b cell numbers or B cell hyperactivity in PD-1$^{-/-}$ mice. This is further supported by the similar effects PD-1 blocking antibodies had on Ag-specific B-1b cell proliferation, IgG3 switching, and IgG production by wild type and $V_H$B1-8 Tg B cells. A large fraction of IgG3-switched cells in PD-1$^{-/-}$ mice were CD11b$^+$, consistent with the key role B-1b cells play in the IgG3 response to PPS3 (Haas et al. (2014) *J. Infectious Diseases* 209:87-97; Haas et al. (2005) *Immunity* 23:7-18). This finding and the results of the $V_H$B1-8 Tg B-1b cell transfer experiments shown herein support the role PD-1 plays in suppressing the ability of B-1b cells to divide and undergo isotype switching. However, it is important to note that the current data do not discount a role for PD-1 in regulating the ability of other B cell subsets to participate in PPS-specific Ab responses. Indeed, PD-1, along with additional activation markers (FSC$^{hi}$CD86$^+$), were expressed by both CD11b$^+$ and CD11b$^-$ PPS3-specific B cells, and in vitro division of both conventional B cells and B-1b cells can be suppressed by PD-1 engagement (Haas (2011) *J. Immunol.* 187:5183-5195), and in vitro studies support a role for PD-1 in diminishing BCR-induced activation and proliferation (Haas (2011) *J. Immunol.* 187:5183-5195; Nishimura et al. (1998) *Int. Immunol.* 10:1563-1572; Zhong et al. (2004) *Int. Immunol.* 16:1181-1188). The selective sensitivities distinct B cell subsets may have to PD-1-mediated regulation remain to be established. Moreover, whether PD-1 signaling on B cells influences PPS-specific Ab diversity, Ab affinity, or additional B cell functions that are independent of proliferation remains to be determined.

Interestingly, use of a PPS-protein conjugate abolished the effect PD-1 deficiency had on PPS-specific Ab responses and survival during pneumococcal infection. PD-1 has been shown to promote TD antibody responses through interactions between PD-1$^+$ T$_{FH}$ cells and B7-DC$^+$ germinal center B cells (Good-Jacobson et al. (2010) *Nature Immunol.* 11:535-542). Moreover, CD40 ligation overcomes PD-1-mediated suppression of BCR-induced proliferation in vitro (Haas (2011) *J. Immunol.* 187:5183-5195). Thus, it is conceivable that T cell help via CD40L overcomes B cell-intrinsic, PD-1-mediated suppression during these responses. Normal Ab responses to the PPS-conjugate vaccine in PD-1$^{-/-}$ mice may reflect a balance between PD-1 suppression of the TI-2 Ab response through B cell-intrinsic expression and support of the TD response through T$_{FH}$ cell-intrinsic expression. Collectively, these studies highlight the complex nature of the PD-1:PD-L pathway in regulating humoral immunity.

In contrast to many studies which support a dominant role for PD-1:B7-H1 interactions in mediating T cell suppression, the current study shows that both B7-H1 and B7-DC are important for suppression of B cell responses to *S. pneumoniae*. Unlike single ligand blockade or genetic deficiency, which had no effect (PPS) or modestly increased IgG responses (TNP-Ficoll), simultaneous B7-H1 and B7-DC blockade in wild type mice yielded significant increases in PPS-specific IgG responses comparable to those observed with PD-1 mAb blockade and in PD-1$^{-/-}$ mice. The interaction between PD-1-expressing Ag-specific B cells and B7-H1- and/or B7-DC-expressing cells ultimately controls the extent of Ag-specific B cell proliferation and switching. While B7-H1 expression is ubiquitous, B7-DC expression is largely limited to dendritic cells, macrophages, B-1a cells, and activated and memory B cells (Brown et al. (2010) *Curr. Opin. Immunol.* 22:397-401; Keir et al. (2008) *Ann. Rev. Immunol.* 26:677-704; Okazaki et al. (2013) *Nature Immunol.* 14:1212-1218; Wang and Chen (2011) *Curr. Top. Microbiol. Immunol.* 344:245-267; Tomayko et al. (2010) *J. Immunol.* 185:7146-7150). An intriguing possibility is that homotypic B cell-B cell interactions among Ag-activated B cells stimulate PD-1:PD-L interactions and thereby suppress PPS-specific B cell proliferation. Identification of the PD-L-expressing cells controlling TI-2 Ag-specific B cell activity may offer further insight into PD-1-mediated regulation of B cell function as well as additional signals regulating TI-2 Ab responses.

In conclusion, the current results demonstrate B cell-intrinsic PD-1 expression suppresses the protective humoral immune response to the capsule of *S. pneumoniae*. The selective suppression of TI-2 Ab responses by PD-1 interactions with B7-H1 and B7-DC points to a novel role for PD-1 in regulating Ag-specific B cell responses to carbohydrate Ags. As cell surface self-Ag bearing repetitive epitopes may initiate TI Ab responses, the PD-1:PD-L pathway may represent a key regulatory checkpoint for limiting the initiation of autoimmunity by innate-like B cells, such as B-1b and marginal zone B cells, known to produce Abs in the absence of cognate T cell interactions. Identifying strategies to transiently overcome this regulatory checkpoint to augment protective B cell responses to polysaccharide-bearing pathogens may be key to improving vaccine efficacy and therapeutic interventions for infectious diseases.

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A single immunogenic composition comprising a pharmaceutically acceptable carrier and an effective amount of one or more isolated or purified pneumococcal capsular polysaccharide antigens in combination with an effective amount of an antibody agent that inhibits the interaction between a PD-1 ligand and a PD-1 polypeptide, wherein the antibody agent is an anti-PD1 ligand antibody and wherein the PD-1 polypeptide comprises the amino acid sequence of SEQ ID NO: 1.

2. A kit comprising:
(a) a composition comprising a pneumococcal capsular polysaccharide vaccine comprising one or more isolated or purified pneumococcal capsular polysaccharide antigens in combination with an antibody agent that inhibits the interaction between a PD-1 ligand and a PD-1 polypeptide, wherein the antibody agent is an anti-PD1 ligand antibody and wherein the PD-1 polypeptide comprises the amino acid sequence of SEQ ID NO: 1; and (b) instructions for administration of the composition (a) to a mammalian subject in need thereof.

3. The immunogenic composition of claim 1, wherein the one or more pneumococcal capsular polysaccharide antigens are from one or more different serotypes of *Streptococcus pneumoniae*.

4. The immunogenic composition of claim 3, wherein the one or more different serotypes of *Streptococcus pneumoniae* are selected from the group consisting of serotypes 1, 2, 3, 4, 5, 6A, 6B, 7F, 8, 9N, 9V, 10A, 11A, 12F, 14, 15B, 17F, 18C, 19A, 19F, 20, 22F, 23F and 33F.

5. The immunogenic composition of claim 1, wherein the PD-1 ligand is PDL1 comprising the amino acid sequence of SEQ ID NO: 2.

6. The immunogenic composition of claim 1, wherein the PD-1 ligand is PDL2 comprising the amino acid sequence of SEQ ID NO: 3.

7. The immunogenic composition of claim 1, wherein the one or more pneumococcal capsular polysaccharide antigens are conjugated to a carrier protein.

8. The immunogenic composition of claim 1, wherein the immunogenic composition further comprises an adjuvant.

9. A method of increasing protective antibody levels to one or more pneumococcal capsular polysaccharide antigens in a mammalian subject in need thereof, the method comprising administering to the subject an effective amount of the immunogenic composition of claim 1, wherein the protective antibody levels are increased compared to a corresponding mammalian subject not administered the one or more isolated pneumococcal capsular polysaccharide antigens and/or the agent that inhibits the interaction between the PD-1 ligand and the PD-1 polypeptide.

10. The method of claim 9, wherein the one or more pneumococcal capsular polysaccharide antigens are from one or more different serotypes of *Streptococcus pneumoniae*.

11. The method of claim 10, wherein the one or more different serotypes of *Streptococcus pneumoniae* are selected from the group consisting of serotypes 1, 2, 3, 4, 5, 6A, 6B, 7F, 8, 9N, 9V, 10A, 11A, 12F, 14, 15B, 17F, 18C, 19A, 19F, 20, 22F, 23F and 33F.

12. The method of claim 9, wherein the PD-1 ligand is PDL1 comprising the amino acid sequence of SEQ ID NO: 2.

13. The method of claim 9, wherein the PD-1 ligand is PDL2 comprising the amino acid sequence of SEQ ID NO: 3.

14. A method of ameliorating one or more symptoms of a pneumococcal infection in a mammalian subject in need thereof, the method comprising administering to the subject an effective amount of the immunogenic composition of claim 1.

* * * * *

UNITED STATES PATENT AND TRADEMARK OFFICE
CERTIFICATE OF CORRECTION

| | | |
|---|---|---|
| PATENT NO. | : 11,708,411 B2 | Page 1 of 3 |
| APPLICATION NO. | : 15/106071 | |
| DATED | : July 25, 2023 | |
| INVENTOR(S) | : Haas et al. | |

It is certified that error appears in the above-identified patent and that said Letters Patent is hereby corrected as shown below:

On the Title Page

(56) References Cited, FOREIGN PATENT DOCUMENTS: Please correct "EP 9171496 B1 5/1993" to read --EP 0171496 B1 5/1993--

(56) References Cited, FOREIGN PATENT DOCUMENTS, Page 2, Column 1, Line 10: Please correct "EP 9378881 B1 6/1993" to read --EP 0378881 B1 6/1993--

In the Specification

Column 1, Lines 19-24: Please delete the paragraph under the heading "FEDERALLY SPONSORED RESEARCH OR DEVELOPMENT" and replace with the following:
STATEMENT OF GOVERNMENT SUPPORT
This invention was made with government support under AI095800 awarded by the National Institutes of Health. The government has certain rights in the invention.

Column 6, Line 59: Please correct "(FSC$^{lo}$TD86$^-$)" to read --(FSC$^{lo}$CD86$^-$)--

Column 6, Line 66: Please correct "(FSC$^{lo}$TD86$^-$)" to read --(FSC$^{lo}$CD86$^-$)--

Column 6, Line 67: Please correct "(FSC$^{lo}$TD86$^+$)" to read --(FSC$^{hi}$CD86$^+$)--

Column 7, Line 7: Please correct "µEMT" to read --µMT--

Column 7, Line 13: Please correct "µEMT" to read --µMT--

Column 7, Line 15: Please correct "µEMT" to read --µMT--

Column 7, Line 25: Please correct "0.1 mg" to read --0.1 µg--

Signed and Sealed this
Twelfth Day of September, 2023

Katherine Kelly Vidal
*Director of the United States Patent and Trademark Office*

CERTIFICATE OF CORRECTION (continued)
U.S. Pat. No. 11,708,411 B2

Column 7, Line 42: Please correct "affinity 2," to read --affinity λ,--

Column 7, Line 59: Please correct "B7-DC (B)" to read --B7-DC$^{-/-}$ (B)--

Column 10, Line 61: Please correct "Prevnar 13®" to read --Prevnar 13®--

Column 15, Line 55: Please correct "1 ng" to read --1μg--

Column 15, Line 61: Please correct "750 μg" to read --750 ng--

Column 18, Line 12: Please correct "EPO427347" to read --EP0427347--

Column 18, Line 15: Please correct "EPO471177" to read --EP0471177--

Column 19, Line 5: Please correct "SLAB" to read --SIAB--

Column 20, Line 65: Please correct "ALHYDROGELAL" to read --ALHYDROGEL--

Column 32, Line 45: Please correct "Oi et ah" to read --Oi et al.--

Column 35, Line 9: Please correct "Si nuclease" to read --S1 nuclease--

Column 36, Line 61: Please correct "(CH2-S)" to read --(—CH2-S)--

Column 37, Line 1: Please correct "(CH2-S)" to read --(—CH2-S)--

Column 45, Line 15: Please correct "Id" to read --Igβ--

Column 49, Line 1: Please correct "nMT" to read --μMT--

Column 49, Line 57: Please correct "10 mg/mL" to read --10 μg/mL--

Column 50, Line 39: Please correct "0.1 mg" to read --~0.1 μg--

Column 51, Line 45: Please correct "μEMT" to read --μMT--

Column 51, Line 46: Please correct "μEMT" to read --μMT--

Column 53, Line 1: Please correct "2 to 2.5-fold" to read --~2 to 2.5-fold--

Column 53, Line 48: Please correct "a 3-fold" to read --a ~3-fold--

Column 53, Line 49: Please correct "(FSC$^{lo}$TD86$^-$)" to read --(FSC$^{lo}$CD86$^-$)--

Column 53, Line 67: Please correct "(nMT)" to read --(μMT)--

CERTIFICATE OF CORRECTION (continued)
U.S. Pat. No. 11,708,411 B2

Column 54, Line 32: Please correct "(2)" to read --($\lambda^-$)--

Column 57, Line 30: Please correct "µEMT" to read --µMT--